United States Patent
Shi et al.

(10) Patent No.: US 12,202,891 B2
(45) Date of Patent: *Jan. 21, 2025

(54) ANTIBODY CAPABLE OF BINDING TO THYMIC STROMAL LYMPHOPOIETIN AND USE THEREOF

(71) Applicants: JIANGSU HENGRUI MEDICINE CO., LTD., Lianyungang (CN); SHANGHAI HENGRUI PHARMACEUTICAL CO., LTD., Shanghai (CN)

(72) Inventors: Jinping Shi, Shanghai (CN); Hua Ying, Shanghai (CN); Tingting Li, Shanghai (CN); Yifang Wang, Shanghai (CN); Guimei Yang, Shanghai (CN); Hu Ge, Shanghai (CN); Weikang Tao, Shanghai (CN)

(73) Assignees: JIANGSU HENGRUI MEDICINE CO., LTD.; SHANGHAI HENGRUI PHARMACEUTICAL CO., LTD.

( * ) Notice: Subject to any disclaimer, the term of this patent is extended or adjusted under 35 U.S.C. 154(b) by 0 days.

This patent is subject to a terminal disclaimer.

(21) Appl. No.: 18/607,180

(22) Filed: Mar. 15, 2024

(65) Prior Publication Data

US 2024/0254215 A1    Aug. 1, 2024

Related U.S. Application Data

(63) Continuation of application No. 17/615,970, filed as application No. PCT/CN2020/094154 on Jun. 3, 2020.

(30) Foreign Application Priority Data

Jun. 4, 2019   (CN) .......................... 201910480579.9

(51) Int. Cl.
| | | |
|---|---|---|
| C07K 16/00 | (2006.01) | |
| A61P 11/06 | (2006.01) | |
| C07K 16/24 | (2006.01) | |
| C07K 16/46 | (2006.01) | |
| A61K 39/00 | (2006.01) | |

(52) U.S. Cl.
CPC .............. *C07K 16/24* (2013.01); *A61P 11/06* (2018.01); *A61K 2039/505* (2013.01); *C07K 2317/24* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

2023/0212610 A1*  7/2023  Debs ................... A61K 9/0019
                                                              424/450

FOREIGN PATENT DOCUMENTS

| CN | 101389657 A | 3/2009 |
|---|---|---|
| CN | 101605814 A | 12/2009 |
| CN | 109206514 A | 1/2019 |
| CN | 109206517 A | 1/2019 |
| WO | 2008155365 A1 | 12/2008 |
| WO | 2009035577 A1 | 3/2009 |
| WO | 2011056772 A1 | 5/2011 |
| WO | 2014031718 A1 | 2/2014 |
| WO | 2016142426 A1 | 9/2016 |
| WO | 2017004149 A1 | 1/2017 |
| WO | 2017042701 A1 | 5/2017 |
| WO | 2018191479 A1 | 10/2018 |

OTHER PUBLICATIONS

Gail M. Gauvreau, Ph.D. et al., "Effects of an Anti-TSLP Antibody on Allergen-Induced Asthmatic Responses", The New England Journal of Medicine (2014), vol. 370, No. 22, pp. 2102-2110 (9 pages).

* cited by examiner

*Primary Examiner* — Maher M Haddad
(74) *Attorney, Agent, or Firm* — GlaxoSmithKline Global Patents

(57) ABSTRACT

Disclosed are an antibody capable of binding to thymic stromal lymphopoietin and the use thereof. Disclosed are an anti-TSLP antibody, comprising a murine antibody, chimeric antibody and humanized antibody of the light chain and heavy chain variable regions of the anti-TSLP antibody and antigen-binding fragments thereof, or a pharmaceutically acceptable salt or solvent compound thereof, and the use thereof as a medicament for treating asthma, especially the use thereof in the preparation of a drug for treating TSLP-positive diseases or conditions.

9 Claims, 5 Drawing Sheets

Specification includes a Sequence Listing.

SEQUENCE LISTING

```
Sequence total quantity: 146
SEQ ID NO: 1            moltype = AA  length = 176
FEATURE                 Location/Qualifiers
REGION                  1..176
                        note = Synthetic Sequence_Amino acid sequence of his-tagged
                        human TSLP antigen (huTSLP-his)
source                  1..176
                        mol_type = protein
                        organism = synthetic construct
SEQUENCE: 1
MFPFALLYVL SVSFRKIFIL QLVGLVLTYD FTNCDFEKIK AAYLSTISKD LITYMSGTKS   60
TEFNNTVSCS NRPHCLTEIQ SLTFNPTAGC ASLAKEMFAM KTKAALAIWC PGYSETQINA  120
TQAMKKARKS KVTTNKCLEQ VSQLQGLWRR FNRPLLKQQG SSDYKDDDDK HHHHHH      176

SEQ ID NO: 2            moltype = AA  length = 398
FEATURE                 Location/Qualifiers
REGION                  1..398
                        note = Synthetic Sequence_Amino acid sequence of Fc-tagged
                        human TSLP antigen (huTSLP-Fc)
source                  1..398
                        mol_type = protein
                        organism = synthetic construct
SEQUENCE: 2
MFPFALLYVL SVSFRKIFIL QLVGLVLTYD FTNCDFEKIK AAYLSTISKD LITYMSGTKS   60
TEFNNTVSCS NRPHCLTEIQ SLTFNPTAGC ASLAKEMFAM KTKAALAIWC PGYSETQINA  120
TQAMKKARKS KVTTNKCLEQ VSQLQGLWRR FNRPLLKQQD IEGRMDEPKS SDKTHTCPPC  180
PAPELLGGPS VFLFPPKPKD TLMISRTPEV TCVVVDVSHE DPEVKFNWYV DGVEVHNAKT  240
KPREEQYNST YRVVSVLTVL HQDWLNGKEY KCKVSNKALP APIEKTISKA KGQPREPQVY  300
TLPPSRDELT KNQVSLTCLV KGFYPSDIAV EWESNGQPEN NYKTTPPVLD SDGSFFLYSK  360
LTVDKSRWQQ GNVFSCSVMH EALHNHYTQK SLSLSPGK                          398

SEQ ID NO: 3            moltype = AA  length = 168
FEATURE                 Location/Qualifiers
REGION                  1..168
                        note = Synthetic Sequence_Amino acid sequence of his-tagged
                        cyno TSLP antigen (cynoTSLP-his)
source                  1..168
                        mol_type = protein
                        organism = synthetic construct
SEQUENCE: 3
METDTLLLWV LLLWVPGSTG YDFTNCDFQK IEADYLRTIS KDLITYMSGT KSTDFNNTVS   60
CSNRPHCLTE IQSLTFNPTP RCASLAKEMF ARKTKATLAL WCPGYSETQI NATQAMKKAR  120
KSKVTTNKCL EQVSQLLGLW RRFIRTLLKQ QGSSDYKDDD DKHHHHHH               168
```

```
SEQ ID NO: 4              moltype = AA   length = 390
FEATURE                   Location/Qualifiers
REGION                    1..390
                          note = Synthetic Sequence_Amino acid sequence of Fc-tagged
                          cyno TSLP antigen (cyno TSLP-Fc)
source                    1..390
                          mol_type = protein
                          organism = synthetic construct
SEQUENCE: 4
METDTLLLWV LLLWVPGSTG YDFTNCDFQK IEADYLRTIS KDLITYMSGT KSTDFNNTVS    60
CSNRPHCLTE IQSLTFNPTP RCASLAKEMF ARKTKATLAL WCPGYSETQI NATQAMKKAR   120
KSKVTTNKCL EQVSQLLGLW RRFIRTLLKQ QDIEGRMDEP KSSDKTHTCP PCPAPELLGG   180
PSVFLFPPKP KDTLMISRTP EVTCVVVDVS HEDPEVKFNW YVDGVEVHNA KTKPREEQYN   240
STYRVVSVLT VLHQDWLNGK EYKCKVSNKA LPAPIEKTIS KAKGQPREPQ VYTLPPSRDE   300
LTKNQVSLTC LVKGFYPSDI AVEWESNGQP ENNYKTTPPV LDSDGSFFLY SKLTVDKSRW   360
QQGNVFSCSV MHEALHNHYT QKSLSLSPGK                                    390

SEQ ID NO: 5              moltype = AA   length = 446
FEATURE                   Location/Qualifiers
REGION                    1..446
                          note = Synthetic Sequence_Amino acid sequence of Fc-tagged
                          human TSLP receptor extracellular domain
                          (human-TSLPR-Fc-ECD)
source                    1..446
                          mol_type = protein
                          organism = synthetic construct
SEQUENCE: 5
GAAEGVQIQI IYFNLETVQV TWNASKYSRT NLTFHYRFNG DEAYDQCTNY LLQEGHTSGC    60
LLDAEQRDDI LYFSIRNGTH PVFTASRWMV YYLKPSSPKH VRFSWHQDAV TVTCSDLSYG   120
DLLYEVQYRS PFDTEWQSKQ ENTCNVTIEG LDAEKCYSFW VRVKAMEDVY GPDTYPSDWS   180
EVTCWQRGEI RDACAETPTP PKPKLSKDIE GRMDEPKSSD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSRDELTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                        446

SEQ ID NO: 6              moltype = AA   length = 121
FEATURE                   Location/Qualifiers
source                    1..121
                          mol_type = protein
                          organism = Mus musculus
SEQUENCE: 6
EVQLQQSGPV LVKPGASVKM SCKASGYTFT DDYMNWVKQS HGKSLEWIGI ISPYNGGTSY    60
NQKFKGKATL TVDKSSSTAY MELNSLTSED SAVYYCARED YDYDGYAMDH WGQGTSVTVS   120
S                                                                   121

SEQ ID NO: 7              moltype = AA   length = 105
FEATURE                   Location/Qualifiers
source                    1..105
                          mol_type = protein
                          organism = Mus musculus
SEQUENCE: 7
QIVLSQSPAI LSASPGEKVT MTCRASSSVS YMHWYQQKPG SSPKPWIYAT SNLASGVPAR    60
FSGSGSGTSY SLTISRVEAE DAATYYCQQW SSNRTFGGGT KLEIK                   105

SEQ ID NO: 8              moltype = AA   length = 120
FEATURE                   Location/Qualifiers
source                    1..120
                          mol_type = protein
                          organism = Mus musculus
SEQUENCE: 8
QAYLQQSGAE LVRPGASVKM SCKASGFAFT TYNMHWVKHT PGQGLEWIGA IYPGNGETSY    60
NQKFKDRATL TVDKSSRTAY MQLSSLTSED SAVYFCARED DYGEGYFDVW GAGTTVTVSS   120

SEQ ID NO: 9              moltype = AA   length = 111
FEATURE                   Location/Qualifiers
source                    1..111
                          mol_type = protein
                          organism = Mus musculus
SEQUENCE: 9
DIVLTQSPAS LAVSLGQRAT ISCRASESVD NSGLSFMHWY QQKPGQPPRL LLYRASNLGS    60
GIPARFSGSG SGTDFTLTLN PVETDDVATY YCQQINTDPL TFGAGTKLEL K            111

SEQ ID NO: 10             moltype = AA   length = 119
FEATURE                   Location/Qualifiers
source                    1..119
                          mol_type = protein
                          organism = Mus musculus
```

```
SEQUENCE: 10
QVQLQQSGAE LVRPGTSVKV SCKASGYAFT NYLIEWVKQR PGQGLEWIGV IDPGNGDTNY    60
NENFKGKATL TADKSSSTAY IELSRLTSED SAVYFCARED NTGTAFDYWG QGTTLTVSS    119

SEQ ID NO: 11           moltype = AA   length = 107
FEATURE                 Location/Qualifiers
source                  1..107
                        mol_type = protein
                        organism = Mus musculus
SEQUENCE: 11
SIVMTQTPKF LLVSAGDRVT ISCKASQSVS SDVTWYQQKP GQSPKLLIYY VSNHYTGVPD    60
RFTGSGYGTD FTFTISSVQA EDLAVYFCQQ HHRFPLTFGA GTKLELK                 107

SEQ ID NO: 12           moltype = AA   length = 117
FEATURE                 Location/Qualifiers
source                  1..117
                        mol_type = protein
                        organism = Mus musculus
SEQUENCE: 12
QVQLQQSGPQ LVRPGASVKI SCKASGYSFT TYWMHWVKQR PGQGLEWIGM IDPSDSETTL    60
IQKFKDKATL TVDKSSSTAY MQLSSPTSED SAVYYCARTL DGYYDYWGQG TTLTVSS      117

SEQ ID NO: 13           moltype = AA   length = 107
FEATURE                 Location/Qualifiers
source                  1..107
                        mol_type = protein
                        organism = Mus musculus
SEQUENCE: 13
DIQMTQSPAS LSASVGETVT ITCRASENIY SYLAWYQQKQ GKSPQLLVYF AKTLAEGVPS    60
RFSGSVSGTQ FSLKINSLQP EDFGSYYCQH HYGTPWTFGG GTKLEIK                 107

SEQ ID NO: 14           moltype = AA   length = 5
FEATURE                 Location/Qualifiers
source                  1..5
                        mol_type = protein
                        organism = Mus musculus
SEQUENCE: 14
DDYMN                                                                5

SEQ ID NO: 15           moltype = AA   length = 17
FEATURE                 Location/Qualifiers
source                  1..17
                        mol_type = protein
                        organism = Mus musculus
SEQUENCE: 15
IISPYNGGTS YNQKFKG                                                  17

SEQ ID NO: 16           moltype = AA   length = 12
FEATURE                 Location/Qualifiers
source                  1..12
                        mol_type = protein
                        organism = Mus musculus
SEQUENCE: 16
EDYDYDGYAM DH                                                       12

SEQ ID NO: 17           moltype = AA   length = 10
FEATURE                 Location/Qualifiers
source                  1..10
                        mol_type = protein
                        organism = Mus musculus
SEQUENCE: 17
RASSSVSYMH                                                          10

SEQ ID NO: 18           moltype = AA   length = 7
FEATURE                 Location/Qualifiers
source                  1..7
                        mol_type = protein
                        organism = Mus musculus
SEQUENCE: 18
ATSNLAS                                                              7

SEQ ID NO: 19           moltype = AA   length = 8
FEATURE                 Location/Qualifiers
source                  1..8
                        mol_type = protein
                        organism = Mus musculus
SEQUENCE: 19
QQWSSNRT                                                             8
```

```
SEQ ID NO: 20           moltype = AA   length = 5
FEATURE                 Location/Qualifiers
source                  1..5
                        mol_type = protein
                        organism = Mus musculus
SEQUENCE: 20
TYNMH                                                                     5

SEQ ID NO: 21           moltype = AA   length = 17
FEATURE                 Location/Qualifiers
source                  1..17
                        mol_type = protein
                        organism = Mus musculus
SEQUENCE: 21
AIYPGNGETS YNQKFKD                                                       17

SEQ ID NO: 22           moltype = AA   length = 11
FEATURE                 Location/Qualifiers
source                  1..11
                        mol_type = protein
                        organism = Mus musculus
SEQUENCE: 22
EDDYGEGYFD V                                                             11

SEQ ID NO: 23           moltype = AA   length = 15
FEATURE                 Location/Qualifiers
source                  1..15
                        mol_type = protein
                        organism = Mus musculus
SEQUENCE: 23
RASESVDNSG LSFMH                                                         15

SEQ ID NO: 24           moltype = AA   length = 7
FEATURE                 Location/Qualifiers
source                  1..7
                        mol_type = protein
                        organism = Mus musculus
SEQUENCE: 24
RASNLGS                                                                   7

SEQ ID NO: 25           moltype = AA   length = 9
FEATURE                 Location/Qualifiers
source                  1..9
                        mol_type = protein
                        organism = Mus musculus
SEQUENCE: 25
QQINTDPLT                                                                 9

SEQ ID NO: 26           moltype = AA   length = 5
FEATURE                 Location/Qualifiers
source                  1..5
                        mol_type = protein
                        organism = Mus musculus
SEQUENCE: 26
NYLIE                                                                     5

SEQ ID NO: 27           moltype = AA   length = 17
FEATURE                 Location/Qualifiers
source                  1..17
                        mol_type = protein
                        organism = Mus musculus
SEQUENCE: 27
VIDPGNGDTN YNENFKG                                                       17

SEQ ID NO: 28           moltype = AA   length = 10
FEATURE                 Location/Qualifiers
source                  1..10
                        mol_type = protein
                        organism = Mus musculus
SEQUENCE: 28
EDNTGTAFDY                                                               10

SEQ ID NO: 29           moltype = AA   length = 11
FEATURE                 Location/Qualifiers
source                  1..11
                        mol_type = protein
                        organism = Mus musculus
SEQUENCE: 29
KASQSVSSDV T                                                             11
```

```
SEQ ID NO: 30            moltype = AA  length = 7
FEATURE                  Location/Qualifiers
source                   1..7
                         mol_type = protein
                         organism = Mus musculus
SEQUENCE: 30
YVSNHYT                                                                    7

SEQ ID NO: 31            moltype = AA  length = 9
FEATURE                  Location/Qualifiers
source                   1..9
                         mol_type = protein
                         organism = Mus musculus
SEQUENCE: 31
QQHHRFPLT                                                                  9

SEQ ID NO: 32            moltype = AA  length = 5
FEATURE                  Location/Qualifiers
source                   1..5
                         mol_type = protein
                         organism = Mus musculus
SEQUENCE: 32
TYWMH                                                                      5

SEQ ID NO: 33            moltype = AA  length = 17
FEATURE                  Location/Qualifiers
source                   1..17
                         mol_type = protein
                         organism = Mus musculus
SEQUENCE: 33
MIDPSDSETT LIQKFKD                                                        17

SEQ ID NO: 34            moltype = AA  length = 8
FEATURE                  Location/Qualifiers
source                   1..8
                         mol_type = protein
                         organism = Mus musculus
SEQUENCE: 34
TLDGYYDY                                                                   8

SEQ ID NO: 35            moltype = AA  length = 11
FEATURE                  Location/Qualifiers
source                   1..11
                         mol_type = protein
                         organism = Mus musculus
SEQUENCE: 35
RASENIYSYL A                                                              11

SEQ ID NO: 36            moltype = AA  length = 7
FEATURE                  Location/Qualifiers
source                   1..7
                         mol_type = protein
                         organism = Mus musculus
SEQUENCE: 36
FAKTLAE                                                                    7

SEQ ID NO: 37            moltype = AA  length = 9
FEATURE                  Location/Qualifiers
source                   1..9
                         mol_type = protein
                         organism = Mus musculus
SEQUENCE: 37
QHHYGTPWT                                                                  9

SEQ ID NO: 38            moltype = AA  length = 105
FEATURE                  Location/Qualifiers
REGION                   1..105
                         note = Synthetic Sequence_hu3 VL-CDR grafted
source                   1..105
                         mol_type = protein
                         organism = synthetic construct
SEQUENCE: 38
EIVLTQSPAT LSLSPGERAT LSCRASSSVS YMHWYQQKPG QAPRLLIYAT SNLASGIPAR          60
FSGSGSGTDF TLTISRLEPE DFAVYYCQQW SSNRTFGGGT KVEIK                         105

SEQ ID NO: 39            moltype = AA  length = 105
FEATURE                  Location/Qualifiers
REGION                   1..105
```

```
                        note = Synthetic Sequence_hu3VL2
source                  1..105
                        mol_type = protein
                        organism = synthetic construct
SEQUENCE: 39
EIVLTQSPAT LSLSPGERAT LSCRASSSVS YMHWYQQKPG QAPRPLIYAT SNLASGIPAR     60
FSGSGSGTDY TLTISRLEPE DFAVYYCQQW SSNRTFGGGT KVEIK                   105

SEQ ID NO: 40           moltype = AA  length = 105
FEATURE                 Location/Qualifiers
REGION                  1..105
                        note = Synthetic Sequence_hu3VL3
source                  1..105
                        mol_type = protein
                        organism = synthetic construct
SEQUENCE: 40
EIVLTQSPAT LSLSPGERAT LSCRASSSVS YMHWYQQKPG QAPRPWIYAT SNLASGVPAR     60
FSGSGSGTDY TLTISRLEPE DFAVYYCQQW SSNRTFGGGT KVEIK                   105

SEQ ID NO: 41           moltype = AA  length = 105
FEATURE                 Location/Qualifiers
REGION                  1..105
                        note = Synthetic Sequence_hu3VL4
source                  1..105
                        mol_type = protein
                        organism = synthetic construct
SEQUENCE: 41
EIVLTQSPAT LSLSPGERAT LSCRASSSVS YMHWYQQKPG QAPRPWIYAT SNLASGVPAR     60
FSGSGSGTSY TLTISRLEPE DFAVYYCQQW SSNRTFGGGT KVEIK                   105

SEQ ID NO: 42           moltype = AA  length = 121
FEATURE                 Location/Qualifiers
REGION                  1..121
                        note = Synthetic Sequence_hu3VH1
source                  1..121
                        mol_type = protein
                        organism = synthetic construct
SEQUENCE: 42
EVQLVQSGAE VKKPGASVKV SCKASGYTFT DDYMNWVRQA PGQRLEWMGI ISPYNGGTSY     60
NQKFKGRVTI TRDTSASTAY MELSSLRSED TAVYYCARED YDYDGYAMDH WGQGTTVTVS    120
S                                                                   121

SEQ ID NO: 43           moltype = AA  length = 121
FEATURE                 Location/Qualifiers
REGION                  1..121
                        note = Synthetic Sequence_hu3VH2
source                  1..121
                        mol_type = protein
                        organism = synthetic construct
SEQUENCE: 43
EVQLVQSGAE VKKPGASVKV SCKASGYTFT DDYMNWVRQA PGQRLEWMGI ISPYNGGTSY     60
NQKFKGRVTL TVDKSASTAY MELSSLRSED TAVYYCARED YDYDGYAMDH WGQGTTVTVS    120
S                                                                   121

SEQ ID NO: 44           moltype = AA  length = 121
FEATURE                 Location/Qualifiers
REGION                  1..121
                        note = Synthetic Sequence_hu3VH3
source                  1..121
                        mol_type = protein
                        organism = synthetic construct
SEQUENCE: 44
EVQLVQSGAE VKKPGASVKV SCKASGYTFT DDYMNWVKQA PGQRLEWIGI ISPYNGGTSY     60
NQKFKGRATL TVDKSASTAY MELSSLRSED TAVYYCARED YDYDGYAMDH WGQGTTVTVS    120
S                                                                   121

SEQ ID NO: 45           moltype = AA  length = 12
FEATURE                 Location/Qualifiers
REGION                  1..12
                        note = Synthetic Sequence_hu3 HCDR3-H110Y
source                  1..12
                        mol_type = protein
                        organism = synthetic construct
SEQUENCE: 45
EDYDYDGYAM DY                                                        12

SEQ ID NO: 46           moltype = AA  length = 8
FEATURE                 Location/Qualifiers
REGION                  1..8
```

```
                            note = Synthetic Sequence_hu3LCDR3-N93D
source                      1..8
                            mol_type = protein
                            organism = synthetic construct
SEQUENCE: 46
QQWSSDRT                                                                       8

SEQ ID NO: 47               moltype = AA   length = 12
FEATURE                     Location/Qualifiers
REGION                      1..12
                            note = Synthetic Sequence_hu3 HCDR3 (general formula)
SITE                        12
                            note = misc_feature - Xaa can be any naturally occurring
                             amino acid
source                      1..12
                            mol_type = protein
                            organism = synthetic construct
SEQUENCE: 47
EDYDYDGYAM DX                                                                 12

SEQ ID NO: 48               moltype = AA   length = 8
FEATURE                     Location/Qualifiers
REGION                      1..8
                            note = Synthetic Sequence_hu3 LCDR (general formula 1)
SITE                        6
                            note = misc_feature - Xaa can be any naturally occurring
                             amino acid
source                      1..8
                            mol_type = protein
                            organism = synthetic construct
SEQUENCE: 48
QQWSSXRT                                                                       8

SEQ ID NO: 49               moltype = AA   length = 105
FEATURE                     Location/Qualifiers
REGION                      1..105
                            note = Synthetic Sequence_Light chain variable sequence of
                             hu3-11
source                      1..105
                            mol_type = protein
                            organism = synthetic construct
SEQUENCE: 49
EIVLTQSPAT LSLSPGERAT LSCRASSSVS YMHWYQQKPG QAPRPWIYAT SNLASGVPAR              60
FSGSGSGTSY TLTISRLEPE DFAVYYCQQW SSDRTFGGGT KVEIK                             105

SEQ ID NO: 50               moltype = AA   length = 121
FEATURE                     Location/Qualifiers
REGION                      1..121
                            note = Synthetic Sequence_Heavy chain variable sequence of
                             hu3-11
source                      1..121
                            mol_type = protein
                            organism = synthetic construct
SEQUENCE: 50
EVQLVQSGAE VKKPGASVKV SCKASGYTFT DDYMNWVRQA PGQRLEWMGI ISPYNGGTSY              60
NQKFKGRVTL TVDKSASTAY MELSSLRSED TAVYYCARED YDYDGYAMDY WGQGTTVTVS             120
S                                                                            121

SEQ ID NO: 51               moltype = AA   length = 105
FEATURE                     Location/Qualifiers
REGION                      1..105
                            note = Synthetic Sequence_hu3VL5
source                      1..105
                            mol_type = protein
                            organism = synthetic construct
SEQUENCE: 51
EIVLTQSPAT LSLSPGERAT LSCRASSSVS YMHWYQQKPG QAPRPWIYAT SNLASGVPAR              60
FSGSGSGTSY TLTISRLEPE DFAVYYCQQS DNVRGFGGGT KVEIK                             105

SEQ ID NO: 52               moltype = AA   length = 105
FEATURE                     Location/Qualifiers
REGION                      1..105
                            note = Synthetic Sequence_hu3VL6
source                      1..105
                            mol_type = protein
                            organism = synthetic construct
SEQUENCE: 52
EIVLTQSPAT LSLSPGERAT LSCRASSSVS YMHWYQQKPG QAPRPWIYAT SNLASGVPAR              60
FSGSGSGTSY TLTISRLEPE DFAVYYCQQS DSGREFGGGT KVEIK                             105
```

```
SEQ ID NO: 53              moltype = AA  length = 8
FEATURE                    Location/Qualifiers
REGION                     1..8
                           note = Synthetic Sequence_hu3 LCDR3-V1
source                     1..8
                           mol_type = protein
                           organism = synthetic construct
SEQUENCE: 53
QQSDNVRG                                                                  8

SEQ ID NO: 54              moltype = AA  length = 8
FEATURE                    Location/Qualifiers
REGION                     1..8
                           note = Synthetic Sequence_hu3 LCDR3-V2
source                     1..8
                           mol_type = protein
                           organism = synthetic construct
SEQUENCE: 54
QQSDSGRE                                                                  8

SEQ ID NO: 55              moltype = AA  length = 8
FEATURE                    Location/Qualifiers
REGION                     1..8
                           note = Synthetic Sequence_hu3 LCDR3 (general formula 2)
REGION                     5..6
                           note = misc_feature - Xaa can be any naturally occurring
                            amino acid
SITE                       8
                           note = misc_feature - Xaa can be any naturally occurring
                            amino acid
source                     1..8
                           mol_type = protein
                           organism = synthetic construct
SEQUENCE: 55
QQSDXXRX                                                                  8

SEQ ID NO: 56              moltype = AA  length = 111
FEATURE                    Location/Qualifiers
REGION                     1..111
                           note = Synthetic Sequence_hu119-VL CDR grafted(IGKV4-1*01)
source                     1..111
                           mol_type = protein
                           organism = synthetic construct
SEQUENCE: 56
DIVMTQSPDS LAVSLGERAT INCRASESVD NSGLSFMHWY QQKPGQPPKL LIYRASNLGS          60
GVPDRFSGSG SGTDFTLTIS SLQAEDVAVY YCQQINTDPL TFGQGTKLEI K                 111

SEQ ID NO: 57              moltype = AA  length = 111
FEATURE                    Location/Qualifiers
REGION                     1..111
                           note = Synthetic Sequence_hu119VL2
source                     1..111
                           mol_type = protein
                           organism = synthetic construct
SEQUENCE: 57
DIVLTQSPDS LAVSLGERAT INCRASESVD NSGLSFMHWY QQKPGQPPKL LIYRASNLGS          60
GVPDRFSGSG SGTDFTLTIS SLQAEDVAVY YCQQINTDPL TFGQGTKLEI K                 111

SEQ ID NO: 58              moltype = AA  length = 111
FEATURE                    Location/Qualifiers
REGION                     1..111
                           note = Synthetic Sequence_hu119VL3
source                     1..111
                           mol_type = protein
                           organism = synthetic construct
SEQUENCE: 58
DIVMTQSPDS LAVSLGERAT INCRASESVD NSGLSFMHWY QQKPGQPPKL LLYRASNLGS          60
GIPDRFSGSG SGTDFTLTIS SLQAEDVAVY YCQQINTDPL TFGQGTKLEI K                 111

SEQ ID NO: 59              moltype = AA  length = 111
FEATURE                    Location/Qualifiers
REGION                     1..111
                           note = Synthetic Sequence_hu119VL4 (Grafted, IGKV3-11*01)
source                     1..111
                           mol_type = protein
                           organism = synthetic construct
SEQUENCE: 59
EIVLTQSPAT LSLSPGERAT LSCRASESVD NSGLSFMHWY QQKPGQAPRL LIYRASNLGS          60
```

```
GIPARFSGSG SGTDFTLTIS SLEPEDFAVY YCQQINTDPL TFGQGTKLEI K            111

SEQ ID NO: 60              moltype = AA   length = 111
FEATURE                    Location/Qualifiers
REGION                     1..111
                           note = Synthetic Sequence_hu119VL5
source                     1..111
                           mol_type = protein
                           organism = synthetic construct
SEQUENCE: 60
EIVLTQSPAT LSLSPGERAT LSCRASESVD NSGLSFMHWY QQKPGQPPRL LLYRASNLGS    60
GIPARFSGSG SGTDFTLTIS SLEPEDFAVY YCQQINTDPL TFGQGTKLEI K             111

SEQ ID NO: 61              moltype = AA   length = 111
FEATURE                    Location/Qualifiers
REGION                     1..111
                           note = Synthetic Sequence_hu119VL6
source                     1..111
                           mol_type = protein
                           organism = synthetic construct
SEQUENCE: 61
DIVLTQSPAT LSLSPGERAT LSCRASESVD NSGLSFMHWY QQKPGQPPRL LLYRASNLGS    60
GIPARFSGSG SGTDFTLTIS SLEPEDFAVY YCQQINTDPL TFGQGTKLEI K             111

SEQ ID NO: 62              moltype = AA   length = 120
FEATURE                    Location/Qualifiers
REGION                     1..120
                           note = Synthetic Sequence_hu119VH1 (Grafted)
source                     1..120
                           mol_type = protein
                           organism = synthetic construct
SEQUENCE: 62
EVQLVQSGAE VKKPGSSVKV SCKASGGTFS TYNMHWVRQA PGQGLEWMGA IYPGNGETSY    60
NQKFKDRVTI TADKSTSTAY MELSSLRSED TAVYYCARED DYGEGYFDVW GQGTTVTVSS    120

SEQ ID NO: 63              moltype = AA   length = 120
FEATURE                    Location/Qualifiers
REGION                     1..120
                           note = Synthetic Sequence_hu119VH2
source                     1..120
                           mol_type = protein
                           organism = synthetic construct
SEQUENCE: 63
EVQLVQSGAE VKKPGSSVKV SCKASGFTFS TYNMHWVRQA PGQGLEWMGA IYPGNGETSY    60
NQKFKDRVTL TVDKSTSTAY MELSSLRSED TAVYYCARED DYGEGYFDVW GQGTTVTVSS    120

SEQ ID NO: 64              moltype = AA   length = 120
FEATURE                    Location/Qualifiers
REGION                     1..120
                           note = Synthetic Sequence_hu119VH3
source                     1..120
                           mol_type = protein
                           organism = synthetic construct
SEQUENCE: 64
EVQLVQSGAE VKKPGSSVKV SCKASGFTFS TYNMHWVKHA PGQGLEWIGA IYPGNGETSY    60
NQKFKDRATL TVDKSTSTAY MELSSLRSED TAVYYCARED DYGEGYFDVW GQGTTVTVSS    120

SEQ ID NO: 65              moltype = AA   length = 120
FEATURE                    Location/Qualifiers
REGION                     1..120
                           note = Synthetic Sequence_hu119VH4
source                     1..120
                           mol_type = protein
                           organism = synthetic construct
SEQUENCE: 65
EVQLVQSGAE VKKPGSSVKV SCKASGFTFS TYNMHWVKHA PGQGLEWIGA IYPGNGETSY    60
NQKFKDRATL TVDKSTSTAY MELSSLRSED TAVYYCARED DYGEGYFDVW GQGTTVTVSS    120

SEQ ID NO: 66              moltype = AA   length = 120
FEATURE                    Location/Qualifiers
REGION                     1..120
                           note = Synthetic Sequence_hu119VH5
source                     1..120
                           mol_type = protein
                           organism = synthetic construct
SEQUENCE: 66
EVQLVQSGAE VKKPGSSVKV SCKASGGTFS TYNMHWVRQA PGQGLEWIGA IYPGNGETSY    60
NQKFKDRATL TVDKSTSTAY MELSSLRSED TAVYYCARED DYGEGYFDVW GQGTTVTVSS    120
```

| | | |
|---|---|---|
| SEQ ID NO: 67 | moltype = AA   length = 120 | |
| FEATURE | Location/Qualifiers | |
| REGION | 1..120 | |
| | note = Synthetic Sequence_hu119VH6 | |
| source | 1..120 | |
| | mol_type = protein | |
| | organism = synthetic construct | |

SEQUENCE: 67
EAQLVQSGAE VKKPGSSVKV SCKASGFTFS TYNMHWVRQA PGQGLEWIGA IYPGNGETSY   60
NQKFKDRATL TVDKSTSTAY MELSSLRSED TAVYYCARED DYGEGYFDVW GQGTTVTVSS  120

| | | |
|---|---|---|
| SEQ ID NO: 68 | moltype = AA   length = 120 | |
| FEATURE | Location/Qualifiers | |
| REGION | 1..120 | |
| | note = Synthetic Sequence_hu119VH7 | |
| source | 1..120 | |
| | mol_type = protein | |
| | organism = synthetic construct | |

SEQUENCE: 68
EVQLVQSGAE VKKPGSSVKV SCKASGGTFS TYNMHWVRQA PGQGLEWIGA IYPGNGETSY   60
NQKFKDRATL TVDKSTRTAY MELSSLRSED TAVYYCARED DYGEGYFDVW GQGTTVTVSS  120

| | | |
|---|---|---|
| SEQ ID NO: 69 | moltype = AA   length = 120 | |
| FEATURE | Location/Qualifiers | |
| REGION | 1..120 | |
| | note = Synthetic Sequence_hu119VH8 | |
| source | 1..120 | |
| | mol_type = protein | |
| | organism = synthetic construct | |

SEQUENCE: 69
EAQLVQSGAE VKKPGSSVKV SCKASGFTFS TYNMHWVRQA PGQGLEWIGA IYPGNGETSY   60
NQKFKDRATL TVDKSTRTAY MELSSLRSED TAVYYCARED DYGEGYFDVW GQGTTVTVSS  120

| | | |
|---|---|---|
| SEQ ID NO: 70 | moltype = AA   length = 15 | |
| FEATURE | Location/Qualifiers | |
| REGION | 1..15 | |
| | note = Synthetic Sequence_hu119 LCDR1-N31S | |
| source | 1..15 | |
| | mol_type = protein | |
| | organism = synthetic construct | |

SEQUENCE: 70
RASESVDSSG LSFMH                                                    15

| | | |
|---|---|---|
| SEQ ID NO: 71 | moltype = AA   length = 15 | |
| FEATURE | Location/Qualifiers | |
| REGION | 1..15 | |
| | note = Synthetic Sequence_hu119 LCDR1-N31Q | |
| source | 1..15 | |
| | mol_type = protein | |
| | organism = synthetic construct | |

SEQUENCE: 71
RASESVDQSG LSFMH                                                    15

| | | |
|---|---|---|
| SEQ ID NO: 72 | moltype = AA   length = 111 | |
| FEATURE | Location/Qualifiers | |
| REGION | 1..111 | |
| | note = Synthetic Sequence_hu119VL2-N31S | |
| source | 1..111 | |
| | mol_type = protein | |
| | organism = synthetic construct | |

SEQUENCE: 72
DIVLTQSPDS LAVSLGERAT INCRASESVD SSGLSFMHWY QQKPGQPPKL LIYRASNLGS   60
GVPDRFSGSG SGTDFTLTIS SLQAEDVAVY YCQQINTDPL TFGQGTKLEI K           111

| | | |
|---|---|---|
| SEQ ID NO: 73 | moltype = AA   length = 111 | |
| FEATURE | Location/Qualifiers | |
| REGION | 1..111 | |
| | note = Synthetic Sequence_hu119VL2-N31Q | |
| source | 1..111 | |
| | mol_type = protein | |
| | organism = synthetic construct | |

SEQUENCE: 73
DIVLTQSPDS LAVSLGERAT INCRASESVD QSGLSFMHWY QQKPGQPPKL LIYRASNLGS   60
GVPDRFSGSG SGTDFTLTIS SLQAEDVAVY YCQQINTDPL TFGQGTKLEI K           111

| | | |
|---|---|---|
| SEQ ID NO: 74 | moltype = AA   length = 111 | |
| FEATURE | Location/Qualifiers | |
| REGION | 1..111 | |
| | note = Synthetic Sequence_hu119VL6-N31S | |

```
                        source          1..111
                                        mol_type = protein
                                        organism = synthetic construct
SEQUENCE: 74
DIVLTQSPAT LSLSPGERAT LSCRASESVD SSGLSFMHWY QQKPGQPPRL LLYRASNLGS    60
GIPARFSGSG SGTDFTLTIS SLEPEDFAVY YCQQINTDPL TFGQGTKLEI K            111

SEQ ID NO: 75           moltype = AA  length = 111
FEATURE                 Location/Qualifiers
REGION                  1..111
                        note = Synthetic Sequence_hu119VL6-N31Q
source                  1..111
                        mol_type = protein
                        organism = synthetic construct
SEQUENCE: 75
DIVLTQSPAT LSLSPGERAT LSCRASESVD QSGLSFMHWY QQKPGQPPRL LLYRASNLGS    60
GIPARFSGSG SGTDFTLTIS SLEPEDFAVY YCQQINTDPL TFGQGTKLEI K            111

SEQ ID NO: 76           moltype = AA  length = 15
FEATURE                 Location/Qualifiers
REGION                  1..15
                        note = Synthetic Sequence_hu119 LCDR1-general formula
SITE                    8
                        note = misc_feature - Xaa can be any naturally occurring
                         amino acid
source                  1..15
                        mol_type = protein
                        organism = synthetic construct
SEQUENCE: 76
RASESVDXSG LSFMH                                                     15

SEQ ID NO: 77           moltype = AA  length = 107
FEATURE                 Location/Qualifiers
REGION                  1..107
                        note = Synthetic Sequence_hu179VL1 (Graft (IGKV4-1*01))
source                  1..107
                        mol_type = protein
                        organism = synthetic construct
SEQUENCE: 77
DIVMTQSPDS LAVSLGERAT INCKASQSVS SDVTWYQQKP GQPPKLLIYY VSNHYTGVPD    60
RFSGSGSGTD FTLTISSLQA EDVAVYYCQQ HHRFPLTFGQ GTKLEIK                 107

SEQ ID NO: 78           moltype = AA  length = 107
FEATURE                 Location/Qualifiers
REGION                  1..107
                        note = Synthetic Sequence_hu179VL2
source                  1..107
                        mol_type = protein
                        organism = synthetic construct
SEQUENCE: 78
DIVMTQSPDS LAVSLGERAT INCKASQSVS SDVTWYQQKP GQSPKLLIYY VSNHYTGVPD    60
RFSGSGSGTD FTLTISSLQA EDVAVYYCQQ HHRFPLTFGQ GTKLEIK                 107

SEQ ID NO: 79           moltype = AA  length = 107
FEATURE                 Location/Qualifiers
REGION                  1..107
                        note = Synthetic Sequence_hu179 VL3
source                  1..107
                        mol_type = protein
                        organism = synthetic construct
SEQUENCE: 79
DIVMTQSPDS LAVSLGERAT INCKASQSVS SDVTWYQQKP GQSPKLLIYY VSNHYTGVPD    60
RFSGSGSGTD FTFTISSLQA EDVAVYYCQQ HHRFPLTFGQ GTKLEIK                 107

SEQ ID NO: 80           moltype = AA  length = 107
FEATURE                 Location/Qualifiers
REGION                  1..107
                        note = Synthetic Sequence_hu179 VL4
source                  1..107
                        mol_type = protein
                        organism = synthetic construct
SEQUENCE: 80
SIVMTQSPDS LAVSLGERAT INCKASQSVS SDVTWYQQKP GQSPKLLIYY VSNHYTGVPD    60
RFSGSGSGTD FTLTISSLQA EDVAVYYCQQ HHRFPLTFGQ GTKLEIK                 107

SEQ ID NO: 81           moltype = AA  length = 107
FEATURE                 Location/Qualifiers
REGION                  1..107
                        note = Synthetic Sequence_hu179VL5 (Grafted(IGKV2-29*02))
```

```
source                  1..107
                        mol_type = protein
                        organism = synthetic construct
SEQUENCE: 81
DIVMTQTPLS LSVTPGQPAS ISCKASQSVS SDVTWYLQKP GQSPQLLIYY VSNHYTGVPD    60
RFSGSGSGTD FTLKISRVEA EDVGVYYCQQ HHRFPLTFGQ GTKLEIK                 107

SEQ ID NO: 82           moltype = AA  length = 107
FEATURE                 Location/Qualifiers
REGION                  1..107
                        note = Synthetic Sequence_hu179VL6
source                  1..107
                        mol_type = protein
                        organism = synthetic construct
SEQUENCE: 82
SIVMTQTPLS LSVTPGQPAS ISCKASQSVS SDVTWYLQKP GQSPQLLIYY VSNHYTGVPD    60
RFSGSGSGTD FTLKISRVEA EDVGVYYCQQ HHRFPLTFGQ GTKLEIK                 107

SEQ ID NO: 83           moltype = AA  length = 107
FEATURE                 Location/Qualifiers
REGION                  1..107
                        note = Synthetic Sequence_hu179VL7
source                  1..107
                        mol_type = protein
                        organism = synthetic construct
SEQUENCE: 83
SIVMTQTPLS LSVTPGQPAS ISCKASQSVS SDVTWYLQKP GQSPQLLIYY VSNHYTGVPD    60
RFSGSGSGTD FTFKISRVEA EDVGVYYCQQ HHRFPLTFGQ GTKLEIK                 107

SEQ ID NO: 84           moltype = AA  length = 107
FEATURE                 Location/Qualifiers
REGION                  1..107
                        note = Synthetic Sequence_hu179VL8
source                  1..107
                        mol_type = protein
                        organism = synthetic construct
SEQUENCE: 84
SIVMTQTPLS LSVTPGQPAS ISCKASQSVS SDVTWYLQKP GQSPQLLIYY VSNHYTGVPD    60
RFSGSGYGTD FTLKISRVEA EDVGVYYCQQ HHRFPLTFGQ GTKLEIK                 107

SEQ ID NO: 85           moltype = AA  length = 119
FEATURE                 Location/Qualifiers
REGION                  1..119
                        note = Synthetic Sequence_hu179VH1 (Grafted)
source                  1..119
                        mol_type = protein
                        organism = synthetic construct
SEQUENCE: 85
EVQLVQSGAE VKKPGSSVKV SCKASGGTFS NYLIEWVRQA PGQGLEWMGV IDPGNGDTNY    60
NENFKGRVTI TADKSTSTAY MELSSLRSED TAVYYCARED NTGTAFDYWG QGTTVTVSS   119

SEQ ID NO: 86           moltype = AA  length = 119
FEATURE                 Location/Qualifiers
REGION                  1..119
                        note = Synthetic Sequence_hu179VH2
source                  1..119
                        mol_type = protein
                        organism = synthetic construct
SEQUENCE: 86
EVQLVQSGAE VKKPGSSVKV SCKASGYTFS NYLIEWVRQA PGQGLEWMGV IDPGNGDTNY    60
NENFKGRVTL TADKSTSTAY MELSSLRSED TAVYYCARED NTGTAFDYWG QGTTVTVSS   119

SEQ ID NO: 87           moltype = AA  length = 119
FEATURE                 Location/Qualifiers
REGION                  1..119
                        note = Synthetic Sequence_hu179VH3
source                  1..119
                        mol_type = protein
                        organism = synthetic construct
SEQUENCE: 87
EVQLVQSGAE VKKPGSSVKV SCKASGYTFS NYLIEWVRQA PGQGLEWIGV IDPGNGDTNY    60
NENFKGRATL TADKSTSTAY IELSSLRSED TAVYYCARED NTGTAFDYWG QGTTVTVSS   119

SEQ ID NO: 88           moltype = AA  length = 119
FEATURE                 Location/Qualifiers
REGION                  1..119
                        note = Synthetic Sequence_hu179VH4
source                  1..119
                        mol_type = protein
```

```
                                organism = synthetic construct
SEQUENCE: 88
EVQLVQSGAE VKKPGSSVKV SCKASGYTFS NYLIEWVKQA PGQGLEWIGV IDPGNGDTNY      60
NENFKGKATL TADKSTSTAY IELSRLRSED TAVYYCARED NTGTAFDYWG QGTTVTVSS      119

SEQ ID NO: 89            moltype = AA   length = 119
FEATURE                  Location/Qualifiers
REGION                   1..119
                         note = Synthetic Sequence_hu179VH5
source                   1..119
                         mol_type = protein
                         organism = synthetic construct
SEQUENCE: 89
EVQLVQSGAE VKKPGSSVKV SCKASGYAFS NYLIEWVRQA PGQGLEWIGV IDPGNGDTNY      60
NENFKGRATL TADKSTSTAY MELSSLRSED TAVYYCARED NTGTAFDYWG QGTTVTVSS      119

SEQ ID NO: 90            moltype = AA   length = 119
FEATURE                  Location/Qualifiers
REGION                   1..119
                         note = Synthetic Sequence_hu179VH1- N55Q
source                   1..119
                         mol_type = protein
                         organism = synthetic construct
SEQUENCE: 90
EVQLVQSGAE VKKPGSSVKV SCKASGGTFS NYLIEWVRQA PGQGLEWMGV IDPGQGDTNY      60
NENFKGRVTI TADKSTSTAY MELSSLRSED TAVYYCARED NTGTAFDYWG QGTTVTVSS      119

SEQ ID NO: 91            moltype = AA   length = 119
FEATURE                  Location/Qualifiers
REGION                   1..119
                         note = Synthetic Sequence_hu179VH1- N55V
source                   1..119
                         mol_type = protein
                         organism = synthetic construct
SEQUENCE: 91
EVQLVQSGAE VKKPGSSVKV SCKASGGTFS NYLIEWVRQA PGQGLEWMGV IDPGVGDTNY      60
NENFKGRVTI TADKSTSTAY MELSSLRSED TAVYYCARED NTGTAFDYWG QGTTVTVSS      119

SEQ ID NO: 92            moltype = AA   length = 119
FEATURE                  Location/Qualifiers
REGION                   1..119
                         note = Synthetic Sequence_hu179VH1- G56V
source                   1..119
                         mol_type = protein
                         organism = synthetic construct
SEQUENCE: 92
EVQLVQSGAE VKKPGSSVKV SCKASGGTFS NYLIEWVRQA PGQGLEWMGV IDPGNVDTNY      60
NENFKGRVTI TADKSTSTAY MELSSLRSED TAVYYCARED NTGTAFDYWG QGTTVTVSS      119

SEQ ID NO: 93            moltype = AA   length = 17
FEATURE                  Location/Qualifiers
REGION                   1..17
                         note = Synthetic Sequence_hu179 HCDR2-N55Q
source                   1..17
                         mol_type = protein
                         organism = synthetic construct
SEQUENCE: 93
VIDPGQGDTN YNENFKG                                                     17

SEQ ID NO: 94            moltype = AA   length = 17
FEATURE                  Location/Qualifiers
REGION                   1..17
                         note = Synthetic Sequence_hu179 HCDR2-N55V
source                   1..17
                         mol_type = protein
                         organism = synthetic construct
SEQUENCE: 94
VIDPGVGDTN YNENFKG                                                     17

SEQ ID NO: 95            moltype = AA   length = 17
FEATURE                  Location/Qualifiers
REGION                   1..17
                         note = Synthetic Sequence_hu179 HCDR2-G56V
source                   1..17
                         mol_type = protein
                         organism = synthetic construct
SEQUENCE: 95
VIDPGNVDTN YNENFKG                                                     17
```

```
SEQ ID NO: 96              moltype = AA  length = 17
FEATURE                    Location/Qualifiers
REGION                     1..17
                           note = Synthetic Sequence_hu179 HCDR2 (general formula)
REGION                     6..7
                           note = misc_feature - Xaa can be any naturally occurring
                            amino acid
source                     1..17
                           mol_type = protein
                           organism = synthetic construct
SEQUENCE: 96
VIDPGXXDTN YNENFKG                                                       17

SEQ ID NO: 97              moltype = AA  length = 119
FEATURE                    Location/Qualifiers
REGION                     1..119
                           note = Synthetic Sequence_hu179VH3-N55V
source                     1..119
                           mol_type = protein
                           organism = synthetic construct
SEQUENCE: 97
EVQLVQSGAE VKKPGSSVKV SCKASGYTFS NYLIEWVRQA PGQGLEWIGV IDPGVGDTNY         60
NENFKGRATL TADKSTSTAY IELSSLRSED TAVYYCARED NTGTAFDYWG QGTTVTVSS          119

SEQ ID NO: 98              moltype = AA  length = 107
FEATURE                    Location/Qualifiers
REGION                     1..107
                           note = Synthetic Sequence_hu179VL2-Y50E
source                     1..107
                           mol_type = protein
                           organism = synthetic construct
SEQUENCE: 98
DIVMTQSPDS LAVSLGERAT INCKASQSVS SDVTWYQQKP GQSPKLLIYE VSNHYTGVPD         60
RFSGSGSGTD FTLTISSLQA EDVAVYYCQQ HHRFPLTFGQ GTKLEIK                      107

SEQ ID NO: 99              moltype = AA  length = 107
FEATURE                    Location/Qualifiers
REGION                     1..107
                           note = Synthetic Sequence_hu179VL2-S52D
source                     1..107
                           mol_type = protein
                           organism = synthetic construct
SEQUENCE: 99
DIVMTQSPDS LAVSLGERAT INCKASQSVS SDVTWYQQKP GQSPKLLIYY VDNHYTGVPD         60
RFSGSGSGTD FTLTISSLQA EDVAVYYCQQ HHRFPLTFGQ GTKLEIK                      107

SEQ ID NO: 100             moltype = AA  length = 107
FEATURE                    Location/Qualifiers
REGION                     1..107
                           note = Synthetic Sequence_hu179VL2-S52E
source                     1..107
                           mol_type = protein
                           organism = synthetic construct
SEQUENCE: 100
DIVMTQSPDS LAVSLGERAT INCKASQSVS SDVTWYQQKP GQSPKLLIYY VENHYTGVPD         60
RFSGSGSGTD FTLTISSLQA EDVAVYYCQQ HHRFPLTFGQ GTKLEIK                      107

SEQ ID NO: 101             moltype = AA  length = 107
FEATURE                    Location/Qualifiers
REGION                     1..107
                           note = Synthetic Sequence_hu179VL2-N53Q
source                     1..107
                           mol_type = protein
                           organism = synthetic construct
SEQUENCE: 101
DIVMTQSPDS LAVSLGERAT INCKASQSVS SDVTWYQQKP GQSPKLLIYY VSQHYTGVPD         60
RFSGSGSGTD FTLTISSLQA EDVAVYYCQQ HHRFPLTFGQ GTKLEIK                      107

SEQ ID NO: 102             moltype = AA  length = 107
FEATURE                    Location/Qualifiers
REGION                     1..107
                           note = Synthetic Sequence_hu179VL2-N53D
source                     1..107
                           mol_type = protein
                           organism = synthetic construct
SEQUENCE: 102
DIVMTQSPDS LAVSLGERAT INCKASQSVS SDVTWYQQKP GQSPKLLIYY VSDHYTGVPD         60
RFSGSGSGTD FTLTISSLQA EDVAVYYCQQ HHRFPLTFGQ GTKLEIK                      107
```

| | |
|---|---|
| SEQ ID NO: 103 | moltype = AA   length = 107 |
| FEATURE | Location/Qualifiers |
| REGION | 1..107 |
| | note = Synthetic Sequence_hu179VL2-N53E |
| source | 1..107 |
| | mol_type = protein |
| | organism = synthetic construct |

SEQUENCE: 103
DIVMTQSPDS LAVSLGERAT INCKASQSVS SDVTWYQQKP GQSPKLLIYY VSEHYTGVPD   60
RFSGSGSGTD FTLTISSLQA EDVAVYYCQQ HHRFPLTFGQ GTKLEIK              107

| | |
|---|---|
| SEQ ID NO: 104 | moltype = AA   length = 107 |
| FEATURE | Location/Qualifiers |
| REGION | 1..107 |
| | note = Synthetic Sequence_hu179VL2-H54Y |
| source | 1..107 |
| | mol_type = protein |
| | organism = synthetic construct |

SEQUENCE: 104
DIVMTQSPDS LAVSLGERAT INCKASQSVS SDVTWYQQKP GQSPKLLIYY VSNYYTGVPD   60
RFSGSGSGTD FTLTISSLQA EDVAVYYCQQ HHRFPLTFGQ GTKLEIK              107

| | |
|---|---|
| SEQ ID NO: 105 | moltype = AA   length = 107 |
| FEATURE | Location/Qualifiers |
| REGION | 1..107 |
| | note = Synthetic Sequence_hu179VL2-H54D |
| source | 1..107 |
| | mol_type = protein |
| | organism = synthetic construct |

SEQUENCE: 105
DIVMTQSPDS LAVSLGERAT INCKASQSVS SDVTWYQQKP GQSPKLLIYY VSNDYTGVPD   60
RFSGSGSGTD FTLTISSLQA EDVAVYYCQQ HHRFPLTFGQ GTKLEIK              107

| | |
|---|---|
| SEQ ID NO: 106 | moltype = AA   length = 107 |
| FEATURE | Location/Qualifiers |
| REGION | 1..107 |
| | note = Synthetic Sequence_hu179VL2-H54E |
| source | 1..107 |
| | mol_type = protein |
| | organism = synthetic construct |

SEQUENCE: 106
DIVMTQSPDS LAVSLGERAT INCKASQSVS SDVTWYQQKP GQSPKLLIYY VSNEYTGVPD   60
RFSGSGSGTD FTLTISSLQA EDVAVYYCQQ HHRFPLTFGQ GTKLEIK              107

| | |
|---|---|
| SEQ ID NO: 107 | moltype = AA   length = 107 |
| FEATURE | Location/Qualifiers |
| REGION | 1..107 |
| | note = Synthetic Sequence_hu179VL2-Y55E |
| source | 1..107 |
| | mol_type = protein |
| | organism = synthetic construct |

SEQUENCE: 107
DIVMTQSPDS LAVSLGERAT INCKASQSVS SDVTWYQQKP GQSPKLLIYY VSNHETGVPD   60
RFSGSGSGTD FTLTISSLQA EDVAVYYCQQ HHRFPLTFGQ GTKLEIK              107

| | |
|---|---|
| SEQ ID NO: 108 | moltype = AA   length = 7 |
| FEATURE | Location/Qualifiers |
| REGION | 1..7 |
| | note = Synthetic Sequence_hu179 LCDR2-Y50E |
| source | 1..7 |
| | mol_type = protein |
| | organism = synthetic construct |

SEQUENCE: 108
EVSNHYT                                                           7

| | |
|---|---|
| SEQ ID NO: 109 | moltype = AA   length = 7 |
| FEATURE | Location/Qualifiers |
| REGION | 1..7 |
| | note = Synthetic Sequence_hu179 LCDR2-S52D |
| source | 1..7 |
| | mol_type = protein |
| | organism = synthetic construct |

SEQUENCE: 109
YVDNHYT                                                           7

| | |
|---|---|
| SEQ ID NO: 110 | moltype = AA   length = 7 |
| FEATURE | Location/Qualifiers |
| REGION | 1..7 |
| | note = Synthetic Sequence_hu179 LCDR2-S52E |

```
source                    1..7
                          mol_type = protein
                          organism = synthetic construct
SEQUENCE: 110
YVENHYT                                                                      7

SEQ ID NO: 111            moltype = AA   length = 7
FEATURE                   Location/Qualifiers
REGION                    1..7
                          note = Synthetic Sequence_hu179LCDR2-N53Q
source                    1..7
                          mol_type = protein
                          organism = synthetic construct
SEQUENCE: 111
YVSQHYT                                                                      7

SEQ ID NO: 112            moltype = AA   length = 7
FEATURE                   Location/Qualifiers
REGION                    1..7
                          note = Synthetic Sequence_hu179 LCDR2-N53D
source                    1..7
                          mol_type = protein
                          organism = synthetic construct
SEQUENCE: 112
YVSDHYT                                                                      7

SEQ ID NO: 113            moltype = AA   length = 7
FEATURE                   Location/Qualifiers
REGION                    1..7
                          note = Synthetic Sequence_hu179 LCDR2-N53E
source                    1..7
                          mol_type = protein
                          organism = synthetic construct
SEQUENCE: 113
YVSEHYT                                                                      7

SEQ ID NO: 114            moltype = AA   length = 7
FEATURE                   Location/Qualifiers
REGION                    1..7
                          note = Synthetic Sequence_hu179 LCDR2-H54Y
source                    1..7
                          mol_type = protein
                          organism = synthetic construct
SEQUENCE: 114
YVSNYYT                                                                      7

SEQ ID NO: 115            moltype = AA   length = 7
FEATURE                   Location/Qualifiers
REGION                    1..7
                          note = Synthetic Sequence_hu179 LCDR2-H54D
source                    1..7
                          mol_type = protein
                          organism = synthetic construct
SEQUENCE: 115
YVSNDYT                                                                      7

SEQ ID NO: 116            moltype = AA   length = 7
FEATURE                   Location/Qualifiers
REGION                    1..7
                          note = Synthetic Sequence_hu179 LCDR2-H54E
source                    1..7
                          mol_type = protein
                          organism = synthetic construct
SEQUENCE: 116
YVSNEYT                                                                      7

SEQ ID NO: 117            moltype = AA   length = 7
FEATURE                   Location/Qualifiers
REGION                    1..7
                          note = Synthetic Sequence_hu179 LCDR2-Y55E
source                    1..7
                          mol_type = protein
                          organism = synthetic construct
SEQUENCE: 117
YVSNHET                                                                      7

SEQ ID NO: 118            moltype =     length =
SEQUENCE: 118
000
```

```
SEQ ID NO: 119          moltype = AA  length = 107
FEATURE                 Location/Qualifiers
REGION                  1..107
                        note = Synthetic Sequence_hu179VL8-N53E
source                  1..107
                        mol_type = protein
                        organism = synthetic construct
SEQUENCE: 119
SIVMTQTPLS LSVTPGQPAS ISCKASQSVS SDVTWYLQKP GQSPQLLIYY VSEHYTGVPD      60
RFSGSGYGTD FTLKISRVEA EDVGVYYCQQ HHRFPLTFGQ GTKLEIK                   107

SEQ ID NO: 120          moltype = AA  length = 107
FEATURE                 Location/Qualifiers
REGION                  1..107
                        note = Synthetic Sequence_hu199VL1 (Grafted)
source                  1..107
                        mol_type = protein
                        organism = synthetic construct
SEQUENCE: 120
DIQMTQSPSS LSASVGDRVT ITCRASENIY SYLAWYQQKP GKAPKLLIYF AKTLAEGVPS      60
RFSGSGSGTD FTLTISSLQP EDFATYYCQH HYGTPWTFGG GTKVEIK                   107

SEQ ID NO: 121          moltype = AA  length = 107
FEATURE                 Location/Qualifiers
REGION                  1..107
                        note = Synthetic Sequence_hu199VL2
source                  1..107
                        mol_type = protein
                        organism = synthetic construct
SEQUENCE: 121
DIQMTQSPSS LSASVGDRVT ITCRASENIY SYLAWYQQKP GKAPKLLVYF AKTLAEGVPS      60
RFSGSGSGTD FTLTISSLQP EDFATYYCQH HYGTPWTFGG GTKVEIK                   107

SEQ ID NO: 122          moltype = AA  length = 107
FEATURE                 Location/Qualifiers
REGION                  1..107
                        note = Synthetic Sequence_hu199VL3
source                  1..107
                        mol_type = protein
                        organism = synthetic construct
SEQUENCE: 122
DIQMTQSPSS LSASVGDRVT ITCRASENIY SYLAWYQQKP GKSPQLLVYF AKTLAEGVPS      60
RFSGSGSGTQ FTLTISSLQP EDFATYYCQH HYGTPWTFGG GTKVEIK                   107

SEQ ID NO: 123          moltype = AA  length = 107
FEATURE                 Location/Qualifiers
REGION                  1..107
                        note = Synthetic Sequence_hu199VL4
source                  1..107
                        mol_type = protein
                        organism = synthetic construct
SEQUENCE: 123
DIQMTQSPSS LSASVGDRVT ITCRASENIY SYLAWYQQKP GKAPKLLIYF AKTLAEGVPS      60
RFSGSVSGTD FTLTISSLQP EDFATYYCQH HYGTPWTFGG GTKVEIK                   107

SEQ ID NO: 124          moltype = AA  length = 107
FEATURE                 Location/Qualifiers
REGION                  1..107
                        note = Synthetic Sequence_hu199VL5
source                  1..107
                        mol_type = protein
                        organism = synthetic construct
SEQUENCE: 124
DIQMTQSPSS LSASVGDRVT ITCRASENIY SYLAWYQQKP GKAPKLLVYF AKTLAEGVPS      60
RFSGSVSGTD FTLTISSLQP EDFATYYCQH HYGTPWTFGG GTKVEIK                   107

SEQ ID NO: 125          moltype = AA  length = 107
FEATURE                 Location/Qualifiers
REGION                  1..107
                        note = Synthetic Sequence_hu199VL6
source                  1..107
                        mol_type = protein
                        organism = synthetic construct
SEQUENCE: 125
DIQMTQSPSS LSASVGDRVT ITCRASENIY SYLAWYQQKP GKSPQLLVYF AKTLAEGVPS      60
RFSGSVSGTQ FTLTISSLQP EDFATYYCQH HYGTPWTFGG GTKVEIK                   107

SEQ ID NO: 126          moltype = AA  length = 117
```

```
FEATURE                 Location/Qualifiers
REGION                  1..117
                        note = Synthetic Sequence_hu199VH1 (Grafted)
source                  1..117
                        mol_type = protein
                        organism = synthetic construct
SEQUENCE: 126
EVQLVQSGAE VKKPGASVKV SCKASGYTFT TYWMHWVRQA PGQGLEWMGM IDPSDSETTL    60
IQKFKDRVTM TRDTSTSTVY MELSSLRSED TAVYYCARTL DGYYDYWGQG TTVTVSS      117

SEQ ID NO: 127          moltype = AA   length = 117
FEATURE                 Location/Qualifiers
REGION                  1..117
                        note = Synthetic Sequence_hu199VH2
source                  1..117
                        mol_type = protein
                        organism = synthetic construct
SEQUENCE: 127
EVQLVQSGAE VKKPGASVKV SCKASGYTFT TYWMHWVRQA PGQGLEWMGM IDPSDSETTL    60
IQKFKDRVTM TVDKSTSTAY MELSSLRSED TAVYYCARTL DGYYDYWGQG TTVTVSS      117

SEQ ID NO: 128          moltype = AA   length = 117
FEATURE                 Location/Qualifiers
REGION                  1..117
                        note = Synthetic Sequence_hu199VH3
source                  1..117
                        mol_type = protein
                        organism = synthetic construct
SEQUENCE: 128
EVQLVQSGAE VKKPGASVKV SCKASGYTFT TYWMHWVRQA PGQGLEWMGM IDPSDSETTL    60
IQKFKDRVTL TVDKSTSTAY MELSSLRSED TAVYYCARTL DGYYDYWGQG TTVTVSS      117

SEQ ID NO: 129          moltype = AA   length = 117
FEATURE                 Location/Qualifiers
REGION                  1..117
                        note = Synthetic Sequence_hu199VH4
source                  1..117
                        mol_type = protein
                        organism = synthetic construct
SEQUENCE: 129
EVQLVQSGAE VKKPGASVKV SCKASGYTFT TYWMHWVRQA PGQGLEWIGM IDPSDSETTL    60
IQKFKDRATL TVDKSTSTAY MELSSLRSED TAVYYCARTL DGYYDYWGQG TTVTVSS      117

SEQ ID NO: 130          moltype = AA   length = 117
FEATURE                 Location/Qualifiers
REGION                  1..117
                        note = Synthetic Sequence_hu199VH5
source                  1..117
                        mol_type = protein
                        organism = synthetic construct
SEQUENCE: 130
EVQLVQSGAE VKKPGASVKV SCKASGYTFT TYWMHWVKQA PGQGLEWIGM IDPSDSETTL    60
IQKFKDKATL TVDKSTSTAY MELSSLRSED TAVYYCARTL DGYYDYWGQG TTVTVSS      117

SEQ ID NO: 131          moltype = AA   length = 117
FEATURE                 Location/Qualifiers
REGION                  1..117
                        note = Synthetic Sequence_hu199VH6
source                  1..117
                        mol_type = protein
                        organism = synthetic construct
SEQUENCE: 131
EVQLVQSGAE VKKPGASVKV SCKASGYTFT TYWMHWVKQA PGQGLEWMGM IDPSDSETTL    60
IQKFKDKVTM TVDKSTSTAY MELSSLRSED TAVYYCARTL DGYYDYWGQG TTVTVSS      117

SEQ ID NO: 132          moltype = AA   length = 117
FEATURE                 Location/Qualifiers
REGION                  1..117
                        note = Synthetic Sequence_hu199VH7
source                  1..117
                        mol_type = protein
                        organism = synthetic construct
SEQUENCE: 132
EVQLVQSGAE VKKPGASVKV SCKASGYTFT TYWMHWVKQA PGQGLEWMGM IDPSDSETTL    60
IQKFKDKVTL TVDKSTSTAY MELSSLRSED TAVYYCARTL DGYYDYWGQG TTVTVSS      117

SEQ ID NO: 133          moltype = AA   length = 330
FEATURE                 Location/Qualifiers
REGION                  1..330
```

```
                         note = Synthetic Sequence_IgG1-YTE heavy chain constant
                          region
source                   1..330
                         mol_type = protein
                         organism = synthetic construct
SEQUENCE: 133
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG 120
PSVFLFPPKP KDTLYITREP EVTCVVVDVS HEDPEVKFNW YVDGVEVHNA KTKPREEQYN 180
STYRVVSVLT VLHQDWLNGK EYKCKVSNKA LPAPIEKTIS KAKGQPREPQ VYTLPPSRDE 240
LTKNQVSLTC LVKGFYPSDI AVEWESNGQP ENNYKTTPPV LDSDGSFFLY SKLTVDKSRW 300
QQGNVFSCSV MHEALHNHYT QKSLSLSPGK                                 330

SEQ ID NO: 134           moltype = AA  length = 107
FEATURE                  Location/Qualifiers
REGION                   1..107
                         note = Synthetic Sequence_kappa light chain constant region
source                   1..107
                         mol_type = protein
                         organism = synthetic construct
SEQUENCE: 134
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC              107

SEQ ID NO: 135           moltype = AA  length = 451
FEATURE                  Location/Qualifiers
REGION                   1..451
                         note = Synthetic Sequence_hu3-13 antibody heavy chain
source                   1..451
                         mol_type = protein
                         organism = synthetic construct
SEQUENCE: 135
EVQLVQSGAE VKKPGASVKV SCKASGYTFT DDYMNWVRQA PGQRLEWMGI ISPYNGGTSY  60
NQKFKGRVTL TVDKSASTAY MELSSLRSED TAVYYCARED YDYDGYAMDY WGQGTTVTVS 120
SASTKGPSVF PLAPSSKSTS GGTAALGCLV KDYFPEPVTV SWNSGALTSG VHTFPAVLQS 180
SGLYSLSSVV TVPSSSLGTQ TYICNVNHKP SNTKVDKKVE PKSCDKTHTC PPCPAPELLG 240
GPSVFLFPPK PKDTLYITRE PEVTCVVVDV SHEDPEVKFN WYVDGVEVHN AKTKPREEQY 300
NSTYRVVSVL TVLHQDWLNG KEYKCKVSNK ALPAPIEKTI SKAKGQPREP QVYTLPPSRD 360
ELTKNQVSLT CLVKGFYPSD IAVEWESNGQ PENNYKTTPP VLDSDGSFFL YSKLTVDKSR 420
WQQGNVFSCS VMHEALHNHY TQKSLSLSPG K                               451

SEQ ID NO: 136           moltype = AA  length = 212
FEATURE                  Location/Qualifiers
REGION                   1..212
                         note = Synthetic Sequence_hu3-13 antibody light chain
source                   1..212
                         mol_type = protein
                         organism = synthetic construct
SEQUENCE: 136
EIVLTQSPAT LSLSPGERAT LSCRASSSVS YMHWYQQKPG QAPRPWIYAT SNLASGVPAR  60
FSGSGSGTSY TLTISRLEPE DFAVYYCQQS DSGREFGGGT KVEIKRTVAA PSVFIFPPSD 120
EQLKSGTASV VCLLNNFYPR EAKVQWKVDN ALQSGNSQES VTEQDSKDST YSLSSTLTLS 180
KADYEKHKVY ACEVTHQGLS SPVTKSFNRG EC                              212

SEQ ID NO: 137           moltype = AA  length = 450
FEATURE                  Location/Qualifiers
REGION                   1..450
                         note = Synthetic Sequence_hu119-30 antibody heavy chain
source                   1..450
                         mol_type = protein
                         organism = synthetic construct
SEQUENCE: 137
EAQLVQSGAE VKKPGSSVKV SCKASGFTFS TYNMHWVRQA PGQGLEWIGA IYPGNGETSY  60
NQKFKDRATL TVDKSTRTAY MELSSLRSED TAVYYCARED DYGEGYFDVW GQGTTVTVSS 120
ASTKGPSVFP LAPSSKSTSG GTAALGCLVK DYFPEPVTVS WNSGALTSGV HTFPAVLQSS 180
GLYSLSSVVT VPSSSLGTQT YICNVNHKPS NTKVDKKVEP KSCDKTHTCP PCPAPELLGG 240
PSVFLFPPKP KDTLYITREP EVTCVVVDVS HEDPEVKFNW YVDGVEVHNA KTKPREEQYN 300
STYRVVSVLT VLHQDWLNGK EYKCKVSNKA LPAPIEKTIS KAKGQPREPQ VYTLPPSRDE 360
LTKNQVSLTC LVKGFYPSDI AVEWESNGQP ENNYKTTPPV LDSDGSFFLY SKLTVDKSRW 420
QQGNVFSCSV MHEALHNHYT QKSLSLSPGK                                 450

SEQ ID NO: 138           moltype = AA  length = 218
FEATURE                  Location/Qualifiers
REGION                   1..218
                         note = Synthetic Sequence_hu119-30 antibody light chain
source                   1..218
                         mol_type = protein
                         organism = synthetic construct
SEQUENCE: 138
```

```
DIVLTQSPAT LSLSPGERAT LSCRASESVD SSGLSFMHWY QQKPGQPPRL LLYRASNLGS    60
GIPARFSGSG SGTDFTLTIS SLEPEDFAVY YCQQINTDPL TFGQGTKLEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 139            moltype = AA  length = 449
FEATURE                   Location/Qualifiers
REGION                    1..449
                          note = Synthetic Sequence_hu179-33 antibody heavy chain
source                    1..449
                          mol_type = protein
                          organism = synthetic construct
SEQUENCE: 139
EVQLVQSGAE VKKPGSSVKV SCKASGYTFS NYLIEWVRQA PGQGLEWIGV IDPGVGDTNY    60
NENFKGRATL TADKSTSTAY IELSSLRSED TAVYYCARED NTGTAFDYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLYITREPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 140            moltype = AA  length = 214
FEATURE                   Location/Qualifiers
REGION                    1..214
                          note = Synthetic Sequence_hu179-33 antibody light chain
source                    1..214
                          mol_type = protein
                          organism = synthetic construct
SEQUENCE: 140
SIVMTQTPLS LSVTPGQPAS ISCKASQSVS SDVTWYLQKP GQSPQLLIYY VSEHYTGVPD    60
RFSGSGYGTD FTLKISRVEA EDVGVYYCQQ HHRFPLTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 141            moltype = AA  length = 447
FEATURE                   Location/Qualifiers
REGION                    1..447
                          note = Synthetic Sequence_hu199-36 antibody heavy chain
source                    1..447
                          mol_type = protein
                          organism = synthetic construct
SEQUENCE: 141
EVQLVQSGAE VKKPGASVKV SCKASGYTFT TYWMHWVKQA PGQGLEWMGM IDPSDSETTL    60
IQKFKDKVTL TVDKSTSTAY MELSSLRSED TAVYYCARTL DGYYDYWGQG TTVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LYITREPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                      447

SEQ ID NO: 142            moltype = AA  length = 214
FEATURE                   Location/Qualifiers
REGION                    1..214
                          note = Synthetic Sequence_hu199-36 antibody light chain
source                    1..214
                          mol_type = protein
                          organism = synthetic construct
SEQUENCE: 142
DIQMTQSPSS LSASVGDRVT ITCRASENIY SYLAWYQQKP GKSPQLLVYF AKTLAEGVPS    60
RFSGSVSGTQ FTLTISSLQP EDFATYYCQH HYGTPWTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 143            moltype = AA  length = 448
FEATURE                   Location/Qualifiers
REGION                    1..448
                          note = Synthetic Sequence_AMG157 heavy chain sequence
source                    1..448
                          mol_type = protein
                          organism = synthetic construct
SEQUENCE: 143
QMQLVESGGG VVQPGRSLRL SCAASGFTFR TYGMHWVRQA PGKGLEWVAV IWYDGSNKHY    60
ADSVKGRFTI TRDNSKNTLN LQMNSLRAED TAVYYCARAP QWELVHEAFD IWGQGTMVTV   120
SSASTKGPSV FPLAPCSRST SESTAALGCL VKDYFPEPVT VSWNSGALTS GVHTFPAVLQ   180
SSGLYSLSSV VTVPSSNFGT QTYTCNVDHK PSNTKVDKTV ERKCCVECPP CPAPPVAGPS   240
VFLFPPKPKD TLMISRTPEV TCVVVDVSHE DPEVQFNWYV DGVEVHNAKT KPREEQFNST   300
FRVVSVLTVV HQDWLNGKEY KCKVSNKGLP APIEKTISKT KGQPREPQVY TLPPSREEMT   360
```

```
KNQVSLTCLV KGFYPSDIAV EWESNGQPEN NYKTTPPMLD SDGSFFLYSK LTVDKSRWQQ    420
GNVFSCSVMH EALHNHYTQK SLSLSPGK                                      448

SEQ ID NO: 144          moltype = AA  length = 214
FEATURE                 Location/Qualifiers
REGION                  1..214
                        note = Synthetic Sequence_AMG157 light chain sequence
source                  1..214
                        mol_type = protein
                        organism = synthetic construct
SEQUENCE: 144
SYVLTQPPSV SVAPGQTARI TCGGNNLGSK SVHWYQQKPG QAPVLVVYDD SDRPSWIPER    60
FSGSNSGNTA TLTISRGEAG DEADYYCQVW DSSSDHVVFG GGTKLTVLGQ PKAAPSVTLF    120
PPSSEELQAN KATLVCLISD FYPGAVTVAW KADSSPVKAG VETTTPSKQS NNKYAASSYL    180
SLTPEQWKSH RSYSCQVTHE GSTVEKTVAP TECS                                214

SEQ ID NO: 145          moltype = AA  length = 371
FEATURE                 Location/Qualifiers
REGION                  1..371
                        note = Synthetic Sequence_Amino acid sequence of human TSLP
                         receptor full-length sequence
source                  1..371
                        mol_type = protein
                        organism = synthetic construct
SEQUENCE: 145
MGRLVLLWGA AVFLLGGWMA LGQGGAAEGV QIQIIYFNLE TVQVTWNASK YSRTNLTFHY    60
RFNGDEAYDQ CTNYLLQEGH TSGCLLDAEQ RDDILYFSIR NGTHPVFTAS RWMVYYLKPS    120
SPKHVRFSWH QDAVTVTCSD LSYGDLLYEV QYRSPFDTEW QSKQENTCNV TIEGLDAEKC    180
YSFWVRVKAM EDVYGPDTYP SDWSEVTCWQ RGEIRDACAE TPTPPKPKLS KFILISSLAI    240
LLMVSLLLLS LWKLWRVKKF LIPSVPDPKS IFPGLFEIHQ GNFQEWITDT QNVAHLHKMA    300
GAEQESGPEE PLVVQLAKTE AESPRMLDPQ TEEKEASGGS LQLPHQPLQG GDVVTIGGFT    360
FVMNDRSYVA L                                                        371

SEQ ID NO: 146          moltype = AA  length = 459
FEATURE                 Location/Qualifiers
REGION                  1..459
                        note = Synthetic Sequence_Amino acid sequence of human IL7R
                         alpha full-length sequence
source                  1..459
                        mol_type = protein
                        organism = synthetic construct
SEQUENCE: 146
MTILGTTFGM VFSLLQVVSG ESGYAQNGDL EDAELDDYSF SCYSQLEVNG SQHSLTCAFE    60
DPDVNTTNLE FEICGALVEV KCLNFRKLQE IYFIETKKFL LIGKSNICVK VGEKSLTCKK    120
IDLTTIVKPE APFDLSVIYR EGANDFVVTF NTSHLQKKYV KVLMHDVAYR QEKDENKWTH    180
VNLSSTKLTL LQRKLQPAAM YEIKVRSIPD HYFKGFWSEW SPSYYFRTPE INNSSGEMDP    240
ILLTISILSF FSVALLVILA CVLWKKRIKP IVWPSLPDHK ITEHLCKKP RKNLNVSFNP    300
ESFLDCQIHR VDDIQARDEV EGFLQDTFPQ QLEESEKQRL GGDVQSPNCP SEDVVITPES    360
FGRDSSLTCL AGNVSACDAP ILSSSRSLDC RESGKNGPHV YQDLLLSLGT TNSTLPPPFS    420
LQSGILTLNP VAQGQPILTS LGSNQEEAYV TMSSFYQNQ                           459
```

ANTIBODY CAPABLE OF BINDING TO THYMIC STROMAL LYMPHOPOIETIN AND USE THEREOF

CROSS-REFERENCE TO RELATED APPLICATIONS

The present application is a continuation patent application which claims the benefit of and priority to U.S. patent application Ser. No. 17/615,970, filed on Dec. 2, 2021, which is the national stage of International Patent Application No. PCT/CN2020/094154, filed on Jun. 3, 2020, which claims the benefit of and priority to Chinese Patent Application No. 201910480579.9 filed on Jun. 4, 2019, which are incorporated herein by reference in their entirety.

SEQUENCE LISTING

The instant application contains a Sequence Listing which has been submitted electronically in XML format and is hereby incorporated by reference in its entirety. Said XML copy, created on Mar. 15, 2024, is named "054624-09-5047-US_Sequence_Listing.xml" and is 188,327 bytes in size.

FIELD OF THE INVENTION

The present disclosure relates to the field of antibody agents. Specifically, the present disclosure relates to anti-TSLP antibody agents and the use thereof.

BACKGROUND OF THE INVENTION

The statements herein only provide background information related to the present disclosure and do not necessarily constitute the prior art.

Asthma is a serious chronic inflammatory airway disease. There are about 334 million asthma patients worldwide and about 30 million asthma patients in China, where the mortality rate is much higher than that in developed countries. As the environment deteriorates and air pollution increases, more people may suffer from this disease, which will seriously endanger human life and health.

Thymic stromal lymphopoietin (TSLP) is an epithelial cell-derived cytokine produced in response to pro-inflammatory stimuli. It mainly promotes allergic inflammation through its activity on dendritic cells and mast cells. TSLP is a type of interleukin 7 (IL-7)-like cytokine, which was first discovered in the conditioned medium of mouse thymic stromal cells. TSLP is mainly expressed in lung, skin and intestinal epithelial cells. TSLP consists of 4 α-helices and two loops AB and CD. In the molecule, there are three pairs of disulfide bonds consisting of six cysteine, two N-glycosylation sites, and the molecular weight is about 15-20 kD. TSLP receptor is a complex consisting of two moieties, one is TSLPR and the other is IL7Rα. TSLP first binds to TSLPR with relatively low affinity, then recruits the binding of IL7Rα with high affinity, and finally activates signal pathways of stat5, etc., leading to the maturation of DCs and the differentiation of T cells.

Myeloid dendritic cells (mDCs) are the major effector cells for TSLP. TSLP acts on immature mDCs, which secrete cytokines IL-8, eotaxin-2, TARC and MDC, while highly express OX40L. In the absence of IL-12, OX40L binds to the native CD4+ T cells, leading to their differentiation into Th2 cells. Th2 cells then secrete Th2 cytokines such as IL-5, IL-4, IL-9, IL-9 and TNF, inducing Th2 inflammatory response in the body. In addition, TSLP can also induce DC cells to produce the cytokine IL-8, which recruits neutrophils in turn, leading to neutrophilic innate immune inflammation. TSLP can also induce DCs to produce eotaxin-2, which recruits eosinophils, and acts together with IL5 to make the body quickly enter the inflammatory state of eosinophil infiltration. TSLP also acts on mast cells and natural killer cells, and mediates innate inflammation by inducing the production of IL-4, IL-6, IgE, etc. In summary, TSLP can cause innate inflammation and Th2 inflammation at the same time, which in turn increases tissue mucus, remodels the airway, which leads to tracheal stenosis, and makes cell fibrosis become severe. The inflammation gradually evolves into the three major allergic diseases, asthma, allergic dermatitis and allergic rhinitis. Therefore, blocking TSLP is a potentially effective strategy for the treatment of diseases such as asthma, allergic dermatitis, etc.

Currently, anti-TSLP antibodies are disclosed in WO2008155365, WO2009035577, WO2011056772, WO2016142426 and WO2017004149. However, there is no corresponding antibody commercially available. Therefore, it is necessary to continue the development of effective medicament for treating TSLP-related diseases.

SUMMARY OF THE INVENTION

The present disclosure provides an anti-TSLP antibody.
In some embodiments, the anti-TSLP antibody as described above comprises an antibody heavy chain variable region and a light chain variable region, wherein:
i) the heavy chain variable region comprises HCDR1, HCDR2 and HCDR3 as shown in SEQ ID NO: 14, SEQ ID NO: 15 and SEQ ID NO: 47, respectively, and the light chain variable region comprises LCDR1, LCDR2 as shown in SEQ ID NO: 17, SEQ ID NO: 18, respectively, and LCDR3 as shown in SEQ ID NO: 48 or 55;
wherein, the sequence of SEQ ID NO: 47 is EDYDYDG-YAMDX$_1$, the sequence of SEQ ID NO: 48 is QQWSSX$_2$RT, the sequence of SEQ ID NO: 55 is QQSDX$_3$X$_4$RX$_5$, wherein X$_1$ is H or Y, X$_2$ is N or D, X$_3$ is N or S, X$_4$ is V or G, X$_5$ is G or E; or
ii) the heavy chain variable region comprises HCDR1, HCDR2 and HCDR3 as shown in SEQ ID NO: 20, SEQ ID NO: 21 and SEQ ID NO: 22, respectively, and the light chain variable region comprises LCDR1, LCDR2 and LCDR3 as shown in SEQ ID NO: 76, SEQ ID NO: 24 and SEQ ID NO: 25, respectively;
wherein, the sequence of SEQ ID NO: 76 is RASESVDX$_6$SGLSFMH, wherein, X$_6$ is selected from N, S or Q; or
iii) the heavy chain variable region comprises HCDR1, HCDR2 and HCDR3 as shown in SEQ ID NO: 26, SEQ ID NO: 96 and SEQ ID NO: 28, respectively, and the light chain variable region comprises LCDR1, LCDR2 and LCDR3 as shown in SEQ ID NO: 29, SEQ ID NO: 118 and SEQ ID NO: 31, respectively;
wherein, the sequence of SEQ ID NO: 96 is VIDPGX$_7$X$_8$DTNYNE, the sequence of SEQ ID NO: 118 is X$_9$VX$_{10}$X$_{11}$X$_{12}$X$_{13}$T, wherein X$_7$ is selected from N, Q and V, X$_8$ is G or V; X$_9$ is Y or E, X$_{10}$ is selected from S, D and E, X$_{11}$ is selected from N, Q, D and E, X$_{12}$ is selected from H, Y, D and E, X$_{13}$ is E or Y; or
iv) the heavy chain variable region comprises HCDR1, HCDR2 and HCDR3 as shown in SEQ ID NO: 32, SEQ ID NO: 33 and SEQ ID NO: 34, respectively, and the light chain variable region comprises LCDR1, LCDR2 and LCDR3 as shown in SEQ ID NO: 35, SEQ ID NO: 36 and SEQ ID NO: 37, respectively.

In some embodiments, the anti-TSLP antibody as described above comprises a heavy chain variable region and a light chain variable region, wherein:
i) the heavy chain variable region comprises HCDR1, HCDR2 and HCDR3 as shown in SEQ ID NO: 14, SEQ ID NO: 15 and SEQ ID NO: 16, respectively, and the light chain variable region comprises LCDR1, LCDR2 and LCDR3 as shown in SEQ ID NO: 17, SEQ ID NO: 18 and SEQ ID NO: 19, respectively; or
ii) the heavy chain variable region comprises HCDR1, HCDR2 and HCDR3 as shown in SEQ ID NO: 14, SEQ ID NO: 15 and SEQ ID NO: 45, respectively, and the light chain variable region comprises LCDR1, LCDR2 and LCDR3 as shown in SEQ ID NO: 17, SEQ ID NO: 18 and SEQ ID NO: 46, respectively; or
iii) the heavy chain variable region comprises HCDR1, HCDR2 and HCDR3 as shown in SEQ ID NO: 14, SEQ ID NO: 15 and SEQ ID NO: 45, respectively, and the light chain variable region comprises LCDR1, LCDR2 and LCDR3 as shown in SEQ ID NO: 17, SEQ ID NO: 18 and SEQ ID NO: 53, respectively; or
iv) the heavy chain variable region comprises HCDR1, HCDR2 and HCDR3 as shown in SEQ ID NO: 14, SEQ ID NO: 15 and SEQ ID NO: 45, respectively, and the light chain variable region comprises LCDR1, LCDR2 and LCDR3 as shown in SEQ ID NO: 17, SEQ ID NO: 18 and SEQ ID NO: 54, respectively; or
v) the heavy chain variable region comprises HCDR1, HCDR2 and HCDR3 as shown in SEQ ID NO: 20, SEQ ID NO: 21 and SEQ ID NO: 22, respectively, and the light chain variable region comprises LCDR1, LCDR2 and LCDR3 as shown in SEQ ID NO: 23, SEQ ID NO: 24 and SEQ ID NO: 25, respectively; or
vi) the heavy chain variable region comprises HCDR1, HCDR2 and HCDR3 as shown in SEQ ID NO: 20, SEQ ID NO: 21 and SEQ ID NO: 22, respectively, and the light chain variable region comprises LCDR1, LCDR2 and LCDR3 as shown in SEQ ID NO: 70, SEQ ID NO: 24 and SEQ ID NO: 25, respectively; or
vii) the heavy chain variable region comprises HCDR1, HCDR2 and HCDR3 as shown in SEQ ID NO: 20, SEQ ID NO: 21 and SEQ ID NO: 22, respectively, and the light chain variable region comprises LCDR1, LCDR2 and LCDR3 as shown in SEQ ID NO: 71, SEQ ID NO: 24 and SEQ ID NO: 25, respectively; or
viii) the heavy chain variable region comprises HCDR1 and HCDR3 as shown in SEQ ID NO: 26, SEQ ID NO: 28, respectively, and HCDR2 as shown in SEQ ID NO: 27, 93, 94 or 95, and the light chain variable region comprises LCDR1 and LCDR3 as shown in SEQ ID NO: 29, SEQ ID NO: 31, respectively, and LCDR2 as shown in SEQ ID NO: 30, 108, 109, 110, 111, 112, 113, 114, 115, 116 or 117.

In some embodiments, the anti-TSLP antibody as described above comprises a heavy chain variable region and a light chain variable region, wherein:
a) the heavy chain variable region comprises HCDR1, HCDR2 and HCDR3 as shown in SEQ ID NO: 26, SEQ ID NO: 27 and SEQ ID NO: 28, respectively, and the light chain variable region comprises LCDR1, LCDR2 and LCDR3 as shown in SEQ ID NO: 29, SEQ ID NO: 30 and SEQ ID NO: 31, respectively; or
b) the heavy chain variable region comprises HCDR1, HCDR2 and HCDR3 as shown in SEQ ID NO: 26, SEQ ID NO: 93 and SEQ ID NO: 28, respectively, and the light chain variable region comprises LCDR1, LCDR2 and LCDR3 as shown in SEQ ID NO: 29, SEQ ID NO: 30 and SEQ ID NO: 31, respectively; or
c) the heavy chain variable region comprises HCDR1, HCDR2 and HCDR3 as shown in SEQ ID NO: 26, SEQ ID NO: 94 and SEQ ID NO: 28, respectively, and the light chain variable region comprises LCDR1, LCDR2 and LCDR3 as shown in SEQ ID NO: 29, SEQ ID NO: 30 and SEQ ID NO: 31, respectively; or
d) the heavy chain variable region comprises HCDR1, HCDR2 and HCDR3 as shown in SEQ ID NO: 26, SEQ ID NO: 95 and SEQ ID NO: 28, respectively, and the light chain variable region comprises LCDR1, LCDR2 and LCDR3 as shown in SEQ ID NO: 29, SEQ ID NO: 30 and SEQ ID NO: 31, respectively; or
e) the heavy chain variable region comprises HCDR1, HCDR2 and HCDR3 as shown in SEQ ID NO: 26, SEQ ID NO: 27 and SEQ ID NO: 28, respectively, and the light chain variable region comprises LCDR1, LCDR2 and LCDR3 as shown in SEQ ID NO: 29, SEQ ID NO: 108 and SEQ ID NO: 31, respectively; or
f) the heavy chain variable region comprises HCDR1, HCDR2 and HCDR3 as shown in SEQ ID NO: 26, SEQ ID NO: 27 and SEQ ID NO: 28, respectively, and the light chain variable region comprises LCDR1, LCDR2 and LCDR3 as shown in SEQ ID NO: 29, SEQ ID NO: 109 and SEQ ID NO: 31, respectively; or
g) the heavy chain variable region comprises HCDR1, HCDR2 and HCDR3 as shown in SEQ ID NO: 26, SEQ ID NO: 27 and SEQ ID NO: 28, respectively, and the light chain variable region comprises LCDR1, LCDR2 and LCDR3 as shown in SEQ ID NO: 29, SEQ ID NO: 110 and SEQ ID NO: 31, respectively; or
h) the heavy chain variable region comprises HCDR1, HCDR2 and HCDR3 as shown in SEQ ID NO: 26, SEQ ID NO: 27 and SEQ ID NO: 28, respectively, and the light chain variable region comprises LCDR1, LCDR2 and LCDR3 as shown in SEQ ID NO: 29, SEQ ID NO: 111 and SEQ ID NO: 31, respectively; or
i) the heavy chain variable region comprises HCDR1, HCDR2 and HCDR3 as shown in SEQ ID NO: 26, SEQ ID NO: 27 and SEQ ID NO: 28, respectively, and the light chain variable region comprises LCDR1, LCDR2 and LCDR3 as shown in SEQ ID NO: 29, SEQ ID NO: 112 and SEQ ID NO: 31, respectively; or
j) the heavy chain variable region comprises HCDR1, HCDR2 and HCDR3 as shown in SEQ ID NO: 26, SEQ ID NO: 27 and SEQ ID NO: 28, respectively, and the light chain variable region comprises LCDR1, LCDR2 and LCDR3 as shown in SEQ ID NO: 29, SEQ ID NO: 113 and SEQ ID NO: 31, respectively; or
k) the heavy chain variable region comprises HCDR1, HCDR2 and HCDR3 as shown in SEQ ID NO: 26, SEQ ID NO: 27 and SEQ ID NO: 28, respectively, and the light chain variable region comprises LCDR1, LCDR2 and LCDR3 as shown in SEQ ID NO: 29, SEQ ID NO: 114 and SEQ ID NO: 31, respectively; or
l) the heavy chain variable region comprises HCDR1, HCDR2 and HCDR3 as shown in SEQ ID NO: 26, SEQ ID NO: 27 and SEQ ID NO: 28, respectively, and the light chain variable region comprises LCDR1, LCDR2 and LCDR3 as shown in SEQ ID NO: 29, SEQ ID NO: 115 and SEQ ID NO: 31, respectively; or
m) the heavy chain variable region comprises HCDR1, HCDR2 and HCDR3 as shown in SEQ ID NO: 26, SEQ ID NO: 27 and SEQ ID NO: 28, respectively, and the light chain variable region comprises LCDR1, LCDR2 and LCDR3 as shown in SEQ ID NO: 29, SEQ ID NO: 116 and SEQ ID NO: 31, respectively; or n) the heavy chain variable region comprises HCDR1, HCDR2 and HCDR3 as shown in SEQ ID NO: 26, SEQ ID NO: 27 and SEQ ID NO: 28, respectively, and the light chain variable region comprises LCDR1, LCDR2 and LCDR3 as shown in SEQ ID NO: 29, SEQ ID NO: 117 and SEQ ID NO: 31, respectively.

In some embodiments of the anti-TSLP antibody as described above, the anti-TSLP antibody is a murine antibody, a chimeric antibody or a humanized antibody.

In some embodiments of the anti-TSLP antibody as described above, the anti-TSLP antibody comprises framework region(s) derived from a human antibody, or the anti-TSLP antibody comprises a light chain variable region and/or a heavy chain variable region selected from those described in (a), (b), (c) or (d) below:

a) the heavy chain variable region comprises HCDR1 and HCDR2 as shown in SEQ ID NO: 14, SEQ ID NO: 15, respectively, and HCDR3 as shown in SEQ ID NO: 16 or 45, and the framework region(s) thereof comprise(s) at most 10 back mutations, preferably, the back mutation is selected from one or more of 38K, 48I, 67A, 69L, 71V and 73K; and/or the light chain variable region comprises LCDR1 and LCDR2 as shown in SEQ ID NO: 17, SEQ ID NO: 18, respectively, and LCDR3 as shown in SEQ ID NO: 19, 46, 53 or 54, and the framework region(s) thereof comprise(s) at most 10 amino acid back mutations, preferably, the back mutation is selected from one or more of 46P, 47W, 58V, 70S and 71Y;

b) the heavy chain variable region comprises HCDR1, HCDR2 and HCDR3 as shown in SEQ ID NO: 20, SEQ ID NO: 21 and SEQ ID NO: 22, respectively, and the framework region(s) thereof comprise(s) at most 10 back mutations, preferably, the back mutation is selected from one or more of 2A, 27F, 38K, 39H, 48I, 67A, 69L, 71V and 76R; and/or the light chain variable region comprises LCDR2 and LCDR3 as shown in SEQ ID NO: 24, SEQ ID NO: 25, respectively, and LCDR1 as shown in SEQ ID NO: 23, 70 or 71, and the framework region(s) thereof comprise(s) at most 10 amino acid back mutations, preferably, the back mutation is one or more of 1D, 4L, 43P, 48L and 58I;

c) the heavy chain variable region comprises HCDR1 and HCDR3 as shown in SEQ ID NO: 26, SEQ ID NO: 28, respectively, and HCDR2 as shown in SEQ ID NO: 27, 93, 94 or 95, and the framework region(s) thereof comprise(s) at most 10 back mutations, preferably, the back mutation is selected from one or more of 27Y, 28A, 38K, 48I, 66K, 67A, 69L, 80I and 82b R; and/or the light chain variable region comprises LCDR1 and LCDR3 as shown in SEQ ID NO: 29, SEQ ID NO: 31, respectively, and LCDR2 as shown in SEQ ID NO: 30, 108, 109, 110, 111, 112, 113, 114, 115, 116 or 117, and the framework region(s) thereof comprise(s) at most 10 back mutations, preferably, the back mutation is selected from one or more of 1S, 43S, 67Y and 73F; or d) the heavy chain variable region comprises HCDR1, HCDR2 and HCDR3 as shown in SEQ ID NO: 32, SEQ ID NO: 33 and SEQ ID NO: 34, respectively, and the framework region(s) thereof comprise(s) at most 10 back mutations, preferably, the back mutation is selected from one or more of 38K, 48I, 66K, 67A, 69L, 71V, 73K and 78A; and/or the light chain variable region comprises LCDR1, LCDR2 and LCDR3 as shown in SEQ ID NO: 35, SEQ ID NO: 36 and SEQ ID NO: 37, respectively, and the framework region(s) thereof comprise(s) at most 10 back mutations, preferably, the back mutation is selected from one or more of 43S, 45Q, 48V, 66V and 70Q.

In some embodiments, the anti-TSLP antibody as described above comprises a heavy chain variable region and a light chain variable region, wherein:

i) the heavy chain variable region has at least 90%, 92%, 94%, 95%, 96%, 97%, 98% or 99% sequence identity with the heavy chain variable region as shown in amino acid sequence SEQ ID NO: 6, 42, 43, 44 or 50, and the light chain variable region has at least 90%, 92%, 94%, 95%, 96%, 97%, 98% or 99% sequence identity with the light chain variable region as shown in amino acid sequence SEQ ID NO: 7, 38, 39, 40, 41, 49, 51 or 52; or ii) the heavy chain variable region has at least 90%, 92%, 94%, 95%, 96%, 97%, 98% or 99% sequence identity with the heavy chain variable region as shown in amino acid sequence SEQ ID NO: 8, 62, 63, 64, 65, 66, 67, 68 or 69, and the light chain variable region has at least 90%, 92%, 94%, 95%, 96%, 97%, 98% or 99% sequence identity with the light chain variable region as shown in amino acid sequence SEQ ID NO: 9, 56, 57, 58, 59, 60, 61, 72, 73, 74 or 75; or iii) the heavy chain variable region has at least 90%, 92%, 94%, 95%, 96%, 97%, 98% or 99% sequence identity with the heavy chain variable region as shown in amino acid sequence SEQ ID NO: 10, 85, 86, 87, 88, 89, 90, 91, 92 or 97, and the light chain variable region has at least 90%, 92%, 94%, 95%, 96%, 97%, 98% or 99% sequence identity with the light chain variable region as shown in amino acid sequence SEQ ID NO: 11, 77, 78, 79, 80, 81, 82, 83, 84, 98, 99, 100, 101, 102, 103, 104, 105, 106, 107 or 119; or iv) the heavy chain variable region has at least 90%, 92%, 94%, 95%, 96%, 97%, 98% or 99% sequence identity with the heavy chain variable region as shown in amino acid sequence SEQ ID NO: 12, 126, 127, 128, 129, 130, 131 or 132, and the light chain variable region has at least 90%, 92%, 94%, 95%, 96%, 97%, 98% or 99% sequence identity with the light chain variable region as shown in amino acid sequence SEQ ID NO: 13, 120, 121, 122, 123, 124 or 125.

In some embodiments of the anti-TSLP antibody as described above, the anti-TSLP antibody is a humanized antibody, which comprises framework region(s) derived from a human antibody or a framework region variant thereof, said framework region variant has at most 1, 2, 3, 4, 5, 6, 7, 8, 9 or 10 amino acid back mutations in the light chain framework region(s) and/or heavy chain framework region(s) of the human antibody, respectively.

In some embodiments of the anti-TSLP antibody as described above, the framework region variant comprises back mutations selected from those described in (a), (b), (c) or (d) below:

a) one or more amino acid back mutations selected from the group consisting of 46P, 47W, 58V, 70S and 71Y comprised in the framework region(s) of the light chain variable region as shown in SEQ ID NO: 38, 49, 51 or 52, and/or one or more amino acid back mutations selected from the group consisting of 38K, 48I, 67A, 69L, 71V and 73K comprised in the framework region (s) of the heavy chain variable region as shown in SEQ ID NO: 42 or 50;

b) one or more amino acid back mutations selected from the group consisting of 1D, 4L, 43P, 48L and 58I comprised in the framework region(s) of the light chain variable region as shown in SEQ ID NO: 56, 59, 72, 73, 74 or 75, and/or one or more amino acid back mutations selected from the group consisting of 2A, 27F, 38K, 39H, 48I, 67A, 69L, 71V and 76R comprised in the framework region(s) of the heavy chain variable region as shown in SEQ ID NO: 62;

c) one or more amino acid back mutations selected from the group consisting of 1S, 43S, 67Y and 73F comprised in the framework region(s) of the light chain variable region as shown in SEQ ID NO: 77, 81, 98, 99, 100, 101, 102, 103, 104, 105, 106, 107 or 119, and/or one or more amino acid back mutations selected from the group consisting of 27Y, 28A, 38K, 48I, 66K, 67A, 69L, 80I and 82b R comprised in the framework region(s) of the heavy chain variable region as shown in SEQ ID NO: 85, 90, 91, 92 or 97;

d) one or more amino acid back mutations selected from the group consisting of 43S, 45Q, 48V, 66V and 70Q comprised in the framework region(s) of the light chain variable region as shown in SEQ ID NO: 120, and/or one or more amino acid back mutations selected from the group consisting of 38K, 48I, 66K, 67A, 69L, 71V, 73K and 78A comprised in the framework region of the heavy chain variable region as shown in SEQ ID NO: 126.

In some embodiments, the anti-TSLP antibody as described above comprises a heavy chain variable region and a light chain variable region, wherein:

i) the amino acid sequence of the heavy chain variable region is as shown in SEQ ID NO: 6, 42, 43, 44 or 50, and the amino acid sequence of the light chain variable region is as shown in SEQ ID NO: 7, 38, 39, 40, 41, 49, 51 or 52; or ii) the amino acid sequence of the heavy chain variable region is as shown in SEQ ID NO: 8, 62, 63, 64, 65, 66, 67, 68 or 69, and the amino acid sequence of the light chain variable region is as shown in SEQ ID NO: 9, 56, 57, 58, 59, 60, 61, 72, 73, 74 or 75; or iii) the amino acid sequence of the heavy chain variable region is as shown in SEQ ID NO: 10, 85, 86, 87, 88, 89, 90, 91, 92 or 97, and the amino acid sequence of the light chain variable region is as shown in SEQ ID NO: 11, 77, 78, 79, 80, 81, 82, 83, 84, 98, 99, 100, 101, 102, 103, 104, 105, 106, 107 or 119; or iv) the amino acid sequence of the heavy chain variable region is as shown in SEQ ID NO: 12, 126, 127, 128, 129, 130, 131 or 132, and the amino acid sequence of the light chain variable region is as shown in SEQ ID NO: 13, 120, 121, 122, 123, 124 or 125.

In some embodiments, the anti-TSLP antibody as described above comprises a heavy chain variable region and a light chain variable region as shown below:

(a) the sequence of the heavy chain variable region is as shown in SEQ ID NO: 6, and the sequence of the light chain variable region is as shown in SEQ ID NO: 7;

(b) the sequence of the heavy chain variable region is as shown in SEQ ID NO: 42, 43 or 44, and the sequence of the light chain variable region is as shown in SEQ ID NO: 39, 40 or 41;

(c) the sequence of the heavy chain variable region is as shown in SEQ ID NO: 43, and the sequence of the light chain variable region is as shown in SEQ ID NO: 38;

(d) the sequence of the heavy chain variable region is as shown in SEQ ID NO: 50, and the sequence of the light chain variable region is as shown in SEQ ID NO: 49, 51 or 52;

(e) the sequence of the heavy chain variable region is as shown in SEQ ID NO: 8, and the sequence of the light chain variable region is as shown in SEQ ID NO: 9;

(f) the sequence of the heavy chain variable region is as shown in SEQ ID NO: 62, 63, 64 or 65, and the sequence of the light chain variable region is as shown in SEQ ID NO: 56, 57 or 58;

(g) the sequence of the heavy chain variable region is as shown in SEQ ID NO: 64, 66, 67, 68 or 69, and the sequence of the light chain variable region is as shown in SEQ ID NO: 59, 60 or 61;

(h) the sequence of the heavy chain variable region is as shown in SEQ ID NO: 64, and the sequence of the light chain variable region is as shown in SEQ ID NO: 72 or 73;

(i) the sequence of the heavy chain variable region is as shown in SEQ ID NO: 69, and the sequence of the light chain variable region is as shown in SEQ ID NO: 74;

(j) the sequence of the heavy chain variable region is as shown in SEQ ID NO: 10, and the sequence of the light chain variable region is as shown in SEQ ID NO: 11;

(k) the sequence of the heavy chain variable region is as shown in SEQ ID NO: 85, and the sequence of the light chain variable region is as shown in SEQ ID NO: 77, 78, 102 or 104;

(l) the sequence of the heavy chain variable region is as shown in SEQ ID NO: 86 or 88, and the sequence of the light chain variable region is as shown in SEQ ID NO: 77 or 78;

(m) the sequence of the heavy chain variable region is as shown in SEQ ID NO: 87, and the sequence of the light chain variable region is as shown in SEQ ID NO: 77, 78, 79, 81, 82, 83, 84, 98, 99, 100, 101, 103, 105, 106 or 107;

(n) the sequence of the heavy chain variable region is as shown in SEQ ID NO: 89, and the sequence of the light chain variable region is as shown in SEQ ID NO: 79, 81, 82, 83 or 84;

(o) the sequence of the heavy chain variable region is as shown in SEQ ID NO: 90, 91 or 92, and the sequence of the light chain variable region is as shown in SEQ ID NO: 78;

(p) the sequence of the heavy chain variable region is as shown in SEQ ID NO: 97, and the sequence of the light chain variable region is as shown in SEQ ID NO: 119;

(q) the sequence of the heavy chain variable region is as shown in SEQ ID NO: 12, and the sequence of the light chain variable region is as shown in SEQ ID NO: 13;

(r) the sequence of the heavy chain variable region is as shown in SEQ ID NO: 127, 128, 129, 130, 131 or 132, and the sequence of the light chain variable region is as shown in SEQ ID NO: 120, 121, 123, 124 or 125; or (s) the sequence of the heavy chain variable region is as shown in SEQ ID NO: 132, and the sequence of the light chain variable region is as shown in SEQ ID NO: 125.

In some embodiments of the anti-TSLP antibody as described above, the combinations of the light chain variable region and the heavy chain variable region of the antibodies are shown as follows:

TABLE 1

Combinations of the light and heavy chain variable regions of the mAb3 humanized antibodies

| Antibody | VH (SEQ ID NO) | VL (SEQ ID NO) |
|---|---|---|
| hu3-01 | 42 | 39 |
| hu3-02 | 42 | 40 |
| hu3-03 | 42 | 41 |
| hu3-04 | 43 | 38 |
| hu3-05 | 43 | 39 |
| hu3-06 | 43 | 40 |
| hu3-07 | 43 | 41 |
| hu3-08 | 44 | 39 |
| hu3-09 | 44 | 40 |
| hu3-10 | 44 | 41 |
| hu3-11 | 50 | 49 |
| hu3-12 | 50 | 51 |
| hu3-13 | 50 | 52 |

TABLE 2

Combinations of the light and heavy chain variable regions of the mAb119 humanized antibodies

| Antibody | VH (SEQ ID NO) | VL (SEQ ID NO) |
|---|---|---|
| hu119-01 | 62 | 56 |
| hu119-02 | 63 | 56 |
| hu119-03 | 64 | 56 |
| hu119-04 | 65 | 56 |
| hu119-05 | 62 | 57 |
| hu119-06 | 63 | 57 |
| hu119-07 | 64 | 57 |
| hu119-08 | 65 | 57 |
| hu119-09 | 62 | 58 |
| hu119-10 | 63 | 58 |
| hu119-11 | 64 | 58 |
| hu119-12 | 65 | 58 |
| hu119-13 | 64 | 59 |
| hu119-14 | 66 | 59 |
| hu119-15 | 67 | 59 |
| hu119-16 | 68 | 59 |
| hu119-17 | 69 | 59 |
| hu119-18 | 64 | 60 |
| hu119-19 | 66 | 60 |
| hu119-20 | 67 | 60 |
| hu119-21 | 68 | 60 |
| hu119-22 | 69 | 60 |
| hu119-23 | 64 | 61 |
| hu119-24 | 66 | 61 |
| hu119-25 | 67 | 61 |
| hu119-26 | 68 | 61 |
| hu119-27 | 69 | 61 |
| hu119-28 | 64 | 72 |
| hu119-29 | 64 | 73 |
| hu119-30 | 69 | 74 |

TABLE 3

Combinations of the light and heavy chain variable regions of the mAb179 humanized antibodies

| Antibody | VH (SEQ ID NO) | VL (SEQ ID NO) |
|---|---|---|
| hu179-01 | 85 | 77 |
| hu179-02 | 85 | 78 |
| hu179-03 | 86 | 77 |
| hu179-04 | 86 | 78 |
| hu179-05 | 87 | 77 |
| hu179-06 | 87 | 78 |
| hu179-07 | 87 | 79 |
| hu179-08 | 87 | 81 |
| hu179-09 | 87 | 82 |
| hu179-10 | 87 | 83 |
| hu179-11 | 87 | 84 |
| hu179-12 | 88 | 77 |
| hu179-13 | 88 | 78 |
| hu179-14 | 89 | 79 |
| hu179-15 | 89 | 80 |
| hu179-16 | 89 | 81 |
| hu179-17 | 89 | 82 |
| hu179-18 | 89 | 83 |
| hu179-19 | 89 | 84 |
| hu179-20 | 90 | 78 |
| hu179-21 | 91 | 78 |
| hu179-22 | 92 | 78 |
| hu179-23 | 85 | 102 |
| hu179-24 | 85 | 104 |
| hu179-25 | 87 | 98 |
| hu179-26 | 87 | 99 |
| hu179-27 | 87 | 100 |
| hu179-28 | 87 | 101 |
| hu179-29 | 87 | 103 |
| hu179-30 | 87 | 105 |
| hu179-31 | 87 | 106 |
| hu179-32 | 87 | 107 |
| hu179-33 | 97 | 119 |

TABLE 4

Combinations of the light and heavy chain variable regions of the mAb199 humanized antibodies

| Antibody | VH (SEQ ID NO) | VL (SEQ ID NO) |
|---|---|---|
| hu199-01 | 127 | 120 |
| hu199-02 | 127 | 121 |
| hu199-03 | 127 | 122 |
| hu199-04 | 127 | 123 |
| hu199-05 | 127 | 124 |
| hu199-06 | 127 | 125 |
| hu199-07 | 128 | 120 |
| hu199-08 | 128 | 121 |
| hu199-09 | 128 | 122 |
| hu199-10 | 128 | 123 |
| hu199-11 | 128 | 124 |
| hu199-12 | 128 | 125 |
| hu199-13 | 129 | 120 |
| hu199-14 | 129 | 121 |
| hu199-15 | 129 | 122 |
| hu199-16 | 129 | 123 |
| hu199-17 | 129 | 124 |
| hu199-18 | 129 | 125 |
| hu199-19 | 130 | 120 |
| hu199-20 | 130 | 121 |
| hu199-21 | 130 | 122 |
| hu199-22 | 130 | 123 |
| hu199-23 | 130 | 124 |
| hu199-24 | 130 | 125 |
| hu199-25 | 131 | 120 |
| hu199-26 | 131 | 121 |
| hu199-27 | 131 | 122 |
| hu199-28 | 131 | 123 |
| hu199-29 | 131 | 124 |
| hu199-30 | 131 | 125 |
| hu199-31 | 132 | 120 |
| hu199-32 | 132 | 121 |
| hu199-33 | 132 | 122 |
| hu199-34 | 132 | 123 |
| hu199-35 | 132 | 124 |
| hu199-36 | 132 | 125 |

In some embodiments of the anti-TSLP antibody as described above, the antibody further comprises antibody constant region(s); preferably, the heavy chain constant region of the antibody constant regions is selected from the group consisting of human IgG1, IgG2, IgG3 and IgG4 constant regions and conventional variants thereof, the light chain constant region of the antibody constant regions is selected from the group consisting of human antibody κ and λ chain constant regions and conventional variants thereof; more preferably, the antibody comprises the heavy chain constant region as shown in sequence SEQ ID NO: 133, and the light chain constant region as shown in sequence SEQ ID NO: 134.

In some embodiments, the anti-TSLP antibody as described above comprises a heavy chain and a light chain as shown below:
(a) the amino acid sequence of the heavy chain is as shown in SEQ ID NO: 135 or has at least 90%, 92%, 94%, 95%, 96%, 97%, 98% or 99% sequence identity with the same, and the amino acid sequence of the light chain is as shown in SEQ ID NO: 136 or has at least 90%, 92%, 94%, 95%, 96%, 97%, 98% or 99% sequence identity with the same;
(b) the amino acid sequence of the heavy chain is as shown in SEQ ID NO: 137 or has at least 90%, 92%, 94%, 95%, 96%, 97%, 98% or 99% sequence identity with the same, and the amino acid sequence of the light chain is as shown in SEQ ID NO: 138 or has at least 90%, 92%, 94%, 95%, 96%, 97%, 98% or 99% sequence identity with the same;
(c) the amino acid sequence of the heavy chain is as shown in SEQ ID NO: 139 or has at least 90%, 92%, 94%, 95%, 96%, 97%, 98% or 99% sequence identity with the same, and the amino acid sequence of the light chain is as shown in SEQ ID NO: 140 or has at least 90% sequence identity with the same; or
(d) the amino acid sequence of the heavy chain is as shown in SEQ ID NO: 141 or has at least 90%, 92%, 94%, 95%, 96%, 97%, 98% or 99% sequence identity with the same, and the amino acid sequence of the light chain is as shown in SEQ ID NO: 142 or has at least 90%, 92%, 94%, 95%, 96%, 97%, 98% or 99% sequence identity with the same.

In some embodiments, the anti-TSLP antibody as described above comprises a heavy chain and a light chain as shown below:
(a) the amino acid sequence of the heavy chain is as shown in SEQ ID NO: 135, and the amino acid sequence of the light chain is as shown in SEQ ID NO: 136;
(b) the amino acid sequence of the heavy chain is as shown in SEQ ID NO: 137, and the amino acid sequence of the light chain is as shown in SEQ ID NO: 138;
(c) the amino acid sequence of the heavy chain is as shown in SEQ ID NO: 139, and the amino acid sequence of the light chain is as shown in SEQ ID NO: 140; or
(d) the amino acid sequence of the heavy chain is as shown in SEQ ID NO: 141, and the amino acid sequence of the light chain is as shown in SEQ ID NO: 142.

In some embodiments, the antibody competitively binds to human TSLP with the anti-TSLP antibody as described above or antigen-binding fragment thereof.

In another aspect, the present disclosure also provides a nucleic acid molecule encoding the anti-TSLP antibody as described above.

In another aspect, the present disclosure also provides an expression vector comprising the nucleic acid molecule as described above.

In another aspect, the present disclosure also provides a host cell comprising the nucleic acid molecule as described above or the expression vector as described above, preferably, the cell is a bacterial cell, a fungal cell, an insect animal cell or a mammalian cell.

In some embodiments, the present disclosure provides a method for preparing the TSLP antibody as described above.

In some embodiments, the present disclosure provides a pharmaceutical composition containing a therapeutically effective amount of the anti-TSLP antibody as described above, or the nucleic acid molecule as described above, or the host cell as described above, as well as one or more pharmaceutically acceptable carriers, diluents, buffers or excipients. Preferably, the therapeutically effective amount means 0.1-3000 mg or 1-1000 mg of the anti-TSLP antibody as described above contained in a unit dose of the composition.

In some embodiments, the present disclosure provides a method for immunodetection or determination of TSLP in vitro or ex vivo, which comprises a step of using the anti-TSLP antibody as described above.

In some embodiments, the present disclosure provides use of the anti-TSLP antibody as described above in preparing reagents for immunodetection of human TSLP.

In some embodiments, the present disclosure provides an anti-TSLP antibody as described above for use in immunodetection or determination of TSLP.

In some embodiments, the present disclosure provides a kit comprising the anti-TSLP antibody as described above.

In some embodiments, the present disclosure provides use of the anti-TSLP antibody as described above, or the nucleic acid molecule as described above, or the host cell as described above or the pharmaceutical composition as described above, in preparing a medicament for treating TSLP-related diseases: wherein the TSLP-related disease includes, but is not limited to: asthma, idiopathic pulmonary fibrosis, atopic dermatitis, allergic conjunctivitis, allergic rhinitis, allergic sinusitis, urticaria, Netherton syndrome, eosinophilic esophagitis, food allergy, allergic diarrhea, eosinophilic gastroenteritis, allergic bronchopulmonary aspergillosis, allergic fungal sinusitis, chronic pruritus, cancer, breast cancer, colon cancer, lung cancer, ovarian cancer, prostate cancer, rheumatoid arthritis, chronic obstructive pulmonary disease, systemic sclerosis, multiple sclerosis, keloidosis, ulcerative colitis, nasal polyposis, chronic eosinophilic pneumonia, eosinophilic bronchitis, celiac disease, Churg-Strauss syndrome, eosinophilic myalgia syndrome, hypereosinophilic syndrome, eosinophilic granulomatosis with polyangiitis, inflammatory bowel disease, scleroderma, interstitial lung disease, fibrosis caused by chronic hepatitis B or C, fibrosis induced by radiation and fibrosis caused by wound healing.

In some embodiments, the present disclosure provides a method for treating TSLP-related diseases, which comprises administering to a subject a therapeutically effective amount of the anti-TSLP antibody as described above, or the nucleic acid molecule as described above, or the host cell as described above or the pharmaceutical composition as described above; asthma, idiopathic pulmonary fibrosis, atopic dermatitis, allergic conjunctivitis, allergic rhinitis, allergic sinusitis, urticaria, Netherton syndrome, eosinophilic esophagitis, food allergy, allergic diarrhea, eosinophilic gastroenteritis, allergic bronchopulmonary aspergillosis, allergic fungal sinusitis, chronic pruritus, cancer, breast cancer, colon cancer, lung cancer, ovarian cancer, prostate cancer, rheumatoid arthritis, chronic obstructive pulmonary disease, systemic sclerosis, multiple sclerosis, keloidosis, ulcerative colitis, nasal polyposis, chronic eosinophilic pneumonia, eosinophilic bronchitis, celiac disease, Churg-Strauss syndrome, eosinophilic myalgia syndrome, hypereosinophilic syndrome, eosinophilic granulomatosis with polyangiitis, inflammatory bowel disease, scleroderma, interstitial lung disease, fibrosis caused by chronic hepatitis B or C, fibrosis induced by radiation and fibrosis caused by wound healing.

In some embodiments, the present disclosure provides an anti-TSLP antibody for use as a medicament, wherein the anti-TSLP antibody is for use in treating TSLP-related diseases, wherein the TSLP-related disease includes, but is not limited to: asthma, idiopathic pulmonary fibrosis, atopic dermatitis, allergic conjunctivitis, allergic rhinitis, allergic sinusitis, urticaria, Netherton syndrome, eosinophilic esophagitis, food allergy, allergic diarrhea, eosinophilic gastroenteritis, allergic bronchopulmonary aspergillosis, allergic fungal sinusitis, chronic pruritus, cancer, breast cancer, colon cancer, lung cancer, ovarian cancer, prostate cancer, rheumatoid arthritis, chronic obstructive pulmonary disease, systemic sclerosis, multiple sclerosis, keloidosis, ulcerative colitis, nasal polyposis, chronic eosinophilic pneumonia, eosinophilic bronchitis, celiac disease, Churg-Strauss syndrome, eosinophilic myalgia syndrome, hypereosinophilic syndrome, eosinophilic granulomatosis with polyangiitis, inflammatory bowel disease, scleroderma, interstitial lung disease, fibrosis caused by chronic hepatitis B or C, fibrosis induced by radiation and fibrosis caused by wound healing.

DETAILED DESCRIPTION OF THE DISCLOSURE

Detailed Description of the Invention

Terminology

Figure 1:
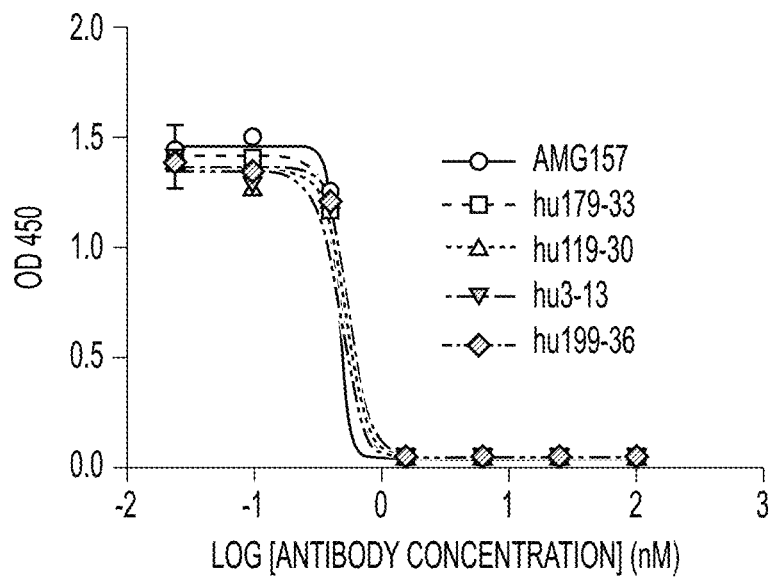
FIG. 1: The result of the antibody blocking the binding activity of TSLP to TSLP receptor.
Figure 2:
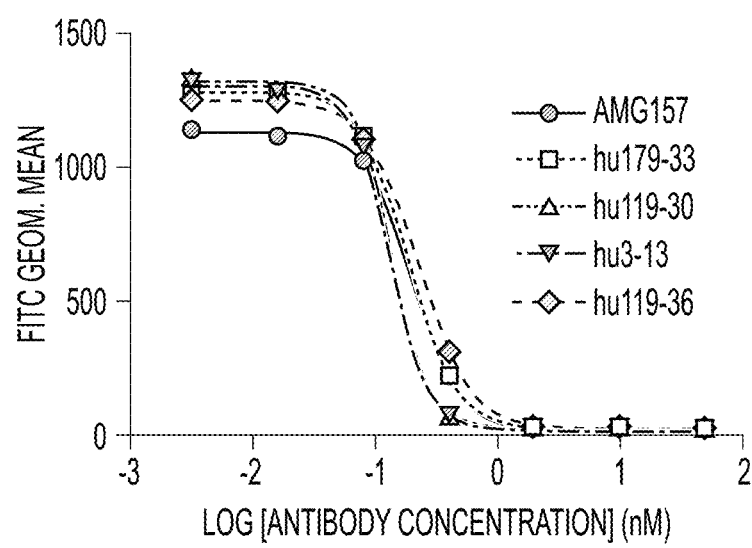
FIG. 2: The result of the antibody blocking the binding activity of TSLP to cell surface TSLP receptor.

To make the present disclosure easier to be understood, certain technical and scientific terms are specifically defined below. Unless clearly defined otherwise herein, all other technical and scientific terms used herein have the meanings commonly understood by those of ordinary skill in the art to which the present disclosure belongs.

The three-letter codes and one-letter codes of amino acids used in the present disclosure are as described in J. biol. chem, 243, p 3558 (1968).

The term "Thymic Stromal Lymphopoietin (TSLP)" is a type I cytokine with four α-helix bundle, and also known as an epithelial cell-derived cytokine produced in response to pro-inflammatory stimuli. It is closely related to interleukin-7 (IL-7), initiates allergic reactions by stimulating dendritic cells (DCs), and is an important factor in regulating the immune response in the human body. The term "TSLP" includes variants, isoforms, homologs, orthologs and paralogues of TSLP.

The "antibody" described in the present disclosure refers to an immunoglobulin, generally, the intact antibody is a tetrapeptide chain structure composed of two identical heavy chains and two identical light chains linked by interchain disulfide bonds. Immunoglobulin heavy chain constant regions exhibit different amino acid compositions and rank orders, hence present different antigenicity. Accordingly, immunoglobulins can be divided into five types, or named as immunoglobulin isotypes, namely IgM, IgD, IgG, IgA and IgE, and the corresponding heavy chains are μ chain, δ chain, γ chain, α chain and ε chain, respectively. The same type of Ig can be further divided into different subclasses according to the difference in the amino acid composition of the hinge region and the number and position of heavy chain disulfide bonds. For example, IgG can be divided into IgG1, IgG2, IgG3 and IgG4. The light chain is divided into κ chain or λ chain by the difference of the constant region. Each of the five types of Ig can have κ chain or λ chain.

The sequence of about 110 amino acids near the N-terminus of the antibody heavy and light chains varies greatly and known as the variable region (Fv region); the remaining amino acid sequence near the C-terminus is relatively stable and is the constant region. The variable region includes 3 hypervariable regions (HVR) and 4 framework regions (FR) with relatively conservative sequences. The 3 hypervariable regions determine the specificity of the antibody, and is also known as complementarity determining regions (CDR). Each light chain variable region (VL) and heavy chain variable region (VH) consists of 3 CDR regions and 4 FR regions. The order from the amino terminus to the carboxy terminus is: FR1, CDR1, FR2, CDR2, FR3, CDR3, FR4. The 3 CDR regions of the light chain refer to LCDR1, LCDR2 and LCDR3; the 3 CDR regions of the heavy chain refer to HCDR1, HCDR2 and HCDR3.

The antibodies of the present disclosure include murine antibodies, chimeric antibodies and humanized antibodies.

The term "murine antibody" in the present disclosure refers to a monoclonal antibody against human TSLP prepared according to the knowledge and skills in the art. During preparation, the test subject is injected with TSLP antigen, and then hybridomas expressing antibodies with the desired sequence or functional properties are isolated. In a preferred embodiment of the present disclosure, the murine anti-TSLP antibody or antigen-binding fragment thereof may further comprise a light chain constant region of murine κ, λ chain or variants thereof, or further comprise a heavy chain constant region of murine IgG1, IgG2, IgG3 or variants thereof.

The term "chimeric antibody" is an antibody formed by fusing the variable region of a murine antibody with the constant region of a human antibody, which can alleviate the immune response induced by murine antibody. Establishing a chimeric antibody requires first establishing a hybridoma secreting murine specific monoclonal antibodies, then cloning the variable region gene from the murine hybridoma cells, and then cloning the constant region gene of the human antibody as necessary, linking the murine variable region gene with the human constant region gene to form a chimeric gene to be inserted into an expression vector, and finally expressing the chimeric antibody molecule in a eukaryotic system or a prokaryotic system. In a preferred embodiment of the present disclosure, the antibody light chain of the TSLP chimeric antibody further comprises a light chain constant region of a human κ, λ chain or variant thereof. The antibody heavy chain of the TSLP chimeric antibody further comprises the heavy chain constant region of human IgG1, IgG2, IgG3, IgG4 or variant thereof, preferably comprises the heavy chain constant region of human IgG1, IgG2 or IgG4, or IgG1, IgG2, or IgG4 variants with amino acid mutations (for example L234A and/or L235A mutations, and/or S228P mutations).

The term "humanized antibody", also known as CDR-grafted antibody, refers to the antibody produced by grafting murine CDR sequences into the framework of human antibody variable regions, that is, an antibody produced in different types of human germline antibody framework sequences. It can overcome the heterogeneous reaction induced by the chimeric antibody as it carries a large amount of murine protein components. Such framework sequences can be obtained from public DNA databases or published references that include germline antibody gene sequences. For example, the germline DNA sequences of the human heavy chain and light chain variable region genes can be found in the "VBase" human germline sequence database (available on the Internet www.mrccpe.com.ac.uk/vbase), as well as in Kabat, E. A., et al., 1991, Sequences of Proteins of Immunological Interest, 5th edition. In order to avoid the decrease in activity at the same time caused by the decrease in immunogenicity, the human antibody variable region framework sequence can be subjected to minimal reverse mutations or back mutations to maintain activity. The humanized antibody of the present disclosure also includes humanized antibodies on which CDR affinity maturation is performed by yeast display.

CDR grafting may result in reduced affinity of the produced antibody or antigen-binding fragment thereof to the antigen due to changes of the framework residues in contact with the antigen. Such interactions may be the result of hypermutation of somatic cells. Therefore, it may still be necessary to graft such donor framework amino acids to the framework of the humanized antibody. The amino acid residues involved in antigen binding and from non-human antibodies or antigen-binding fragments thereof can be identified by examining the sequence and structure of the animal monoclonal antibody variable region. Residues in the CDR donor framework that differ from the germline can be considered related. If the closest germline cannot be determined, the sequence can be compared with the consensus sequence of a subclass or animal antibody sequence with a high percentage of similarity. Rare framework residues are thought to be the result of hypermutation of somatic cells and thus play an important role in binding.

In one embodiment of the present disclosure, the antibody or antigen-binding fragment thereof may further comprise the light chain constant region of human or murine κ, λ chain or variant thereof, or further comprise the heavy chain constant region of human or murine IgG1, IgG2, IgG3, IgG4 or variant thereof; preferably comprising the heavy chain constant region of human IgG1, IgG2 or IgG4, or IgG1, IgG2 or IgG4 variants with amino acid mutations (for example L234A/L235A mutation, S228P mutation, YTE mutation).

The "conventional variant" of the human antibody heavy chain constant region and the human antibody light chain constant region described in the present disclosure refer to the variant of heavy chain constant region or light chain constant region that has been disclosed in the prior art and does not change the structure and function of the antibody variable region. Exemplary variants include IgG1, IgG2, IgG3 or IgG4 heavy chain constant region variants with site-directed modifications and amino acid substitutions of the heavy chain constant region. Specific substitutions are such as YTE mutations, L234A and/or L235A mutations, S228P mutations, and/or mutations to obtain a knob-into-hole structure (making the antibody heavy chain have a combination of knob-Fc and hole-Fc) known in the art. These mutations have been confirmed to make the antibody have new properties, but does not change the function of the antibody variable region.

"Human antibody (HuMAb)", "antibody derived from human", "fully human antibody"and" completely human antibody" can be used interchangeably, and can be antibodies derived from humans or antibodies obtained from a genetically modified organism which has been "engineered" to produce specific human antibodies in response to antigen stimulation and can be produced by any method known in the art. In some technologies, the elements of human heavy chain and light chain gene loci are introduced into cell lines of organisms derived from embryonic stem cell lines, in which the endogenous heavy chain and light chain genetic loci are target disrupted. Transgenic organisms can synthesize human antibodies specific to human antigens, and the organisms can be used to produce human antibody-secreting hybridomas. A human antibody can also be an antibody in which the heavy and light chains are encoded by nucleotide sequences derived from one or more human DNA sources. A fully human antibody can also be constructed by gene or chromosome transfection methods and phage display technology, or constructed by B cells activated in vitro, all of which are known in the art.

The terms "full-length antibody", "intact antibody", "complete antibody" and "whole antibody" are used interchangeably herein and refer to an antibody in a substantially intact form, as distinguished from the antigen-binding fragments defined below. These terms specifically refer to an antibody whose light chain and heavy chain comprises constant region. The "antibody" of the present disclosure includes "full-length antibody" and antigen-binding fragments thereof.

In some embodiments, the full-length antibody of the present disclosure includes antibodies formed by linking the light chain variable region to the light chain constant region, and linking the heavy chain variable region to the heavy chain constant region, as shown in the light and heavy chain combination in the table 1 to 4 below. Those skilled in the art can select different antibody-derived light chain constant regions and heavy chain constant regions according to actual needs, for example, human antibody-derived light chain constant regions and heavy chain constant regions.

The term "antigen-binding fragment" or "functional fragment" of an antibody refers to one or more fragments of the antibody that retain the ability to specifically bind to an antigen (for example, TSLP). It has been shown that fragments of full-length antibodies can be used to perform the antigen-binding function of antibodies. Examples of the binding fragment included in the term "antigen-binding fragment" of an antibody include (i) Fab fragment, a monovalent fragment consisting of VL, VH, CL and CH1 domains; (ii) F(ab')₂ fragment, a bivalent fragment comprising two Fab fragments linked by a disulfide bridge in the hinge region; (iii) Fd fragment, consisting of VH and CH1 domains; (iv) Fv fragment, consisting of VH and VL domains of one arm of the antibody; (V) dsFv, a stable antigen-binding fragment formed by interchain disulfide bonds between VH and VL; (vi) diabody, bispecific antibody and multispecific antibody, comprising fragments like scFv, dsFv, Fab, etc. In addition, although the two domains VL and VH of the Fv fragment are encoded by separate genes, recombination methods can be used to link them by synthetic linkers so that it can be produced as a single protein chain in which the VL and VH regions pair to form a monovalent molecule (referred to as single-chain Fv (scFv); see, for example, Bird et al. (1988) Science 242:423-426; and Huston et al. (1988) Proc. Natl. Acad. Sci USA 85: 5879-5883). Such single chain antibodies are also included in the term "antigen-binding fragment" of an antibody. Such antibody fragments are obtained by using conventional techniques known to those skilled in the art, and screened in the same manner as that used for intact antibodies. The antigen binding moiety can be produced by recombinant DNA technology or by enzymatic or chemical fragmentation of the intact immunoglobulin. The antibodies may be antibodies of different isotypes, for example, IgG (for example, IgG1, IgG2, IgG3 or IgG4 subtypes), IgA1, IgA2, IgD, IgE or IgM antibodies.

Fab is an antibody fragment that has a molecular weight of about 50,000 and has antigen-binding activity among fragments obtained by treating IgG antibody molecules with papain (which cleaves the amino acid residue at position 224 of the H chain), in which about half of the H chain of the N-terminal side and the entire L chain are joined together by disulfide bonds.

F(ab')2 is an antibody fragment that has a molecular weight of about 100,000 and has antigen-binding activity and comprises two Fab regions connected at the hinge position among fragments obtained by digesting the lower part of the two disulfide bonds in the hinge region of IgG with the enzyme pepsin.

Fab' is an antibody fragment that has a molecular weight of about 50,000 and has antigen-binding activity obtained by cleaving the disulfide bond in the hinge region of the F(ab')2. The Fab' of the present disclosure can be produced by using reducing agents, for example dithiothreitol, to treat the F(ab')2 of the present disclosure which specifically recognizes TSLP and binds to the amino acid sequence of the extracellular domain or three-dimensional structure thereof.

In addition, the Fab' can be produced by inserting the DNA encoding the Fab' fragment of the antibody into a prokaryotic expression vector or a eukaryotic expression vector and introducing the vector into a prokaryotic organism or eukaryotic organism to express the Fab'.

The term "single-chain antibody", "single-chain Fv" or "scFv" refers to molecules comprising an antibody heavy chain variable domain (or region, VH) and an antibody light chain variable domain (or region, VL) connected by a linker. Such scFv molecules can have the general structure: NH₂—VL-linker-VH—COOH or NH₂—VH-linker-VL-COOH. Suitable prior art linkers consist of repeated GGGGS amino acid sequences or variants thereof, for example using 1 to 4 repeated variants (Holliger et al. (1993), Proc. Natl. Acad. Sci. USA 90: 6444-6448). Other linkers that can be used in the present disclosure are described in Alfthan et al. (1995), Protein Eng. 8:725-731, Choi et al. (2001), Eur. J. Immunol. 31:94-106, Hu et al. (1996), Cancer Res. 56:3055-3061, Kipriyanov et al. (1999), J. Mol. Biol. 293:41-56 and Roovers et al. (2001), Cancer Immunol.

Diabody is an antibody fragment in which scFv or Fab is dimerized, and is an antibody fragment with bivalent antigen-binding activity. In the bivalent antigen binding activity, the two antigens can be the same or different.

Bispecific antibody and multispecific antibody refer to an antibody that can simultaneously bind to two or more antigens or antigenic determinants, including scFv or Fab fragments that can bind to TSLP.

The diabody of the present disclosure can be produced by the following steps: obtaining the coding cDNA of VH and VL of the monoclonal antibody of the present disclosure which specifically recognizes human TSLP and binds to the amino acid sequence of the extracellular domain or three-dimensional structure thereof, constructing the DNA encoding scFv so that the amino acid sequence length of the peptide linker is 8 residues or less, inserting the DNA into a prokaryotic expression vector or a eukaryotic expression vector, and then introducing the expression vector into a prokaryote organism or eukaryotic organism to express the diabody.

dsFv is obtained by linking VH and VL polypeptides in which one amino acid residue in each is substituted with a cysteine residue via disulfide bonds between the cysteine residues. The amino acid residues substituted with cysteine residues can be selected according to known methods (Protein Engineering, 7, 697 (1994)) based on the three-dimensional structure prediction of the antibody.

The full-length antibody or antigen-binding fragment of the present disclosure can be produced by the following steps: obtaining the coding cDNA of VH and VL of the monoclonal antibody of the present disclosure which specifically recognizes human TSLP and binds to the amino acid sequence of the extracellular domain or three-dimensional structure thereof, constructing the DNA encoding the full-length antibody or antigen-binding fragment, inserting the DNA into a prokaryotic expression vector or a eukaryotic expression vector, and then introducing the expression vector into a prokaryotic organism or eukaryotic organism for expression.

The term "amino acid difference" or "amino acid mutation" refers to the presence of amino acid changes or mutations in the variant protein or polypeptide compared with the original protein or polypeptide, including occurrence of 1, 2, 3 or more amino acid insertion, deletion or substitution on the basis of the original protein or polypeptide.

The term "antibody framework" or "FR region" refers to a moiety of the variable domain VL or VH, which serves as a scaffold for the antigen binding loop (CDR) of the variable domain. Essentially, it is a variable domain without CDR.

The term "complementarity determining region", "CDR" or "hypervariable region" refers to one of the six hypervariable regions in the variable domain of an antibody that mainly contribute to antigen binding. Generally, there are three CDRs (HCDR1, HCDR2, HCDR3) in each heavy chain variable region, and three CDRs (LCDR1, LCDR2, LCDR3) in each light chain variable region. Any one of a variety of well-known schemes can be used to determine the amino acid sequence boundaries of the CDRs, including the "Kabat" numbering rules (see Kabat et al. (1991), "Sequences of Proteins of Immunological Interest", 5th edition, Public Health Service, National Institutes of Health, Bethesda, MD), "Chothia" numbering rules (see Al-Lazikani et al., (1997) JMB 273: 927-948) and ImmunoGenTics (IMGT) numbering rules (Lefranc M. P., Immunologist, 7, 132-136 (1999); Lefranc, M. P., et al., Dev. Comp. Immunol., 27, 55-77 (2003)), etc. For example, for the classical format, following the Kabat rule, the amino acid residue numbers of CDRs in the heavy chain variable domain (VH) are 31-35 (HCDR1), 50-65 (HCDR2) and 95-102 (HCDR3); the amino acid residue numbers of CDRs in the light chain variable domain (VL) are 24-34 (LCDR1), 50-56 (LCDR2) and 89-97 (LCDR3). Following the Chothia rule, the amino acid residue numbers of CDRs in VH are 26-32 (HCDR1), 52-56 (HCDR2) and 95-102 (HCDR3); and the amino acid residue numbers in VL are 26-32 (LCDR1), 50-52 (LCDR2) and 91-96 (LCDR3). By combining the CDR definitions of both Kabat and Chothia, the CDRs consist of amino acid residues 26-35 (HCDR1), 50-65 (HCDR2) and 95-102 (HCDR3) in human VH and amino acid residues 24-34 (LCDR1), 50-56 (LCDR2) and 89-97 (LCDR3) in human VL. Following IMGT rules, the amino acid residue numbers of CDRs in VH are roughly 26-35 (CDR1), 51-57 (CDR2) and 93-102 (CDR3), and the amino acid residue numbers of CDRss in VL are roughly 27-32 (CDR1), 50-52 (CDR2) and 89-97 (CDR3). Following IMGT rules, the CDR regions of an antibody can be determined by using the program IMGT/DomainGap Align.

The term "epitope" or "antigenic determinant" refers to a site on an antigen where an immunoglobulin or antibody specifically binds (for example, a specific site on TSLP molecules). Epitopes generally include at least 3, 4, 5, 6, 7, 8, 9, 10, 11, 12, 13, 14 or 15 consecutive or non-consecutive amino acids in a unique spatial conformation. See, for example, Epitope Mapping Protocols in Methods in Molecular Biology, Vol. 66, G. E. Morris, Ed. (1996).

The terms "specifically binds", "selectively binds", "binds selectively" and "binds specifically" refer to the binding of an antibody to an epitope on a predetermined antigen. Generally, an antibody binds with an affinity (KD) of about less than $10^{-8}$M, for example about less than $10^{-9}$M, $10^{-10}$M, $10^{-11}$M, $10^{-12}$M or less.

The term "KD" refers to the dissociation equilibrium constant of a specific antibody-antigen interaction. Generally, the antibody of the present disclosure binds to TSLP with an affinity (KD) of about less than $10^{-7}$M, for example about less than $10^{-8}$M or $10^{-9}$M, for example, in the present disclosure, the affinity of the antibody to the cell surface antigen is determined by the FACS or Biacore method to determine the KD value.

When the term "competition" is used in the context of antigen-binding proteins (for example neutralizing antigen-binding protein or neutralizing antibody) that compete for the same epitope, it refers to the competition between the antigen-binding proteins, which is determined by the following assay: in the assay, the antigen-binding proteins to be tested (for example antibodies or immunological functional fragments thereof) prevent or inhibit (for example reduce) the specific binding of a reference antigen-binding protein (for example a ligand or a reference antibody) to a common antigen (for example TSLP antigen or fragment thereof). Numerous types of competitive binding assays can be used to determine whether one antigen-binding protein competes with another, these assays are for example: solid phase direct or indirect radioimmunoassay (RIA), solid phase direct or indirect enzyme immunoassay (EIA), sandwich competition assay (see for example Stahli et al., 1983, Methods in Enzymology 9:242-253); solid phase direct biotin-avidin EIA (see for example Kirkland et al., 1986, J. Immunol. 137:3614-3619), solid phase direct labeling assay, solid phase direct labeling sandwich assay (see for example Harlow and Lane, 1988, Antibodies, A Laboratory Manual, Cold Spring Harbor Press); solid phase direct labeling RIA with I-125 labels (see for example Morel et al., 1988, Molec. Immunol. 25: 7-15); solid-phase direct biotin-avidin EIA (see for example Cheung, et al., 1990, Virology 176: 546-552); and directly labeling RIA (Moldenhauer et al., 1990, Scand. J. Immunol. 32:77-82). Generally, the assays involve using any one of unlabeled test antigen-binding protein and labeled reference antigen-binding protein to bind purified antigens bound to a solid surface or cells. Competitive inhibition is measured by measuring the amount of label bound to the solid surface or cells in the presence of the test antigen-binding protein. Generally, the test antigen-binding protein is present in excess. The antigen-binding proteins identified by competition assays (competitive antigen-binding proteins) include: antigen-binding proteins that bind to the same epitope as the reference antigen-binding protein; and antigen-binding proteins that binds to adjacent epitopes that are sufficiently close to the binding epitope of the reference antigen-binding protein, the two epitopes sterically hindering each other from binding. Generally, when the competitive antigen-binding protein is present in excess, it will inhibit (for example reduce) the specific binding of the reference antigen-binding protein to the common antigen by at least 40-45%, 45-50%, 50-55%, 55-60%, 60-65%, 65-70%, 70%-75% or 75% or more. In some cases, the binding is inhibited by at least 80-85%, 85-90%, 90-95%, 95-97%, or 97% or more.

The term "nucleic acid molecule" used herein refers to DNA molecule and RNA molecule. The nucleic acid molecule can be single-stranded or double-stranded, and is preferably double-stranded DNA or single-stranded mRNA or modified mRNA. When a nucleic acid is placed in a functional relationship with another nucleic acid sequence, the nucleic acid is "operably linked". For example, if a promoter or enhancer affects the transcription of a coding sequence, then the promoter or enhancer is operably linked to the coding sequence.

Amino acid sequence "identity" "identity" refers to the percentage of the amino acid residues that are identical between the first and the second sequence when the amino acid sequences are aligned (introducing gaps when necessary) to achieve the maximum percentage of sequence identity, and no conservative substitutions are considered as part of the sequence identity. For the purpose of determining the percentage of amino acid sequence identity, the alignment can be achieved by a variety of ways within the technical scope of the art, for example, using publicly available computer software, such as BLAST, BLAST-2, ALIGN, ALIGN-2 or Megalign (DNASTAR) software. Those skilled in the art can determine the parameters suitable for measuring the alignment, including any algorithm required to achieve the maximum alignment over the entire length of the sequences being compared.

The term "expression vector" refers to a nucleic acid molecule capable of transporting another nucleic acid to which it has been linked. In one embodiment, the vector is a "plasmid", which refers to a circular double-stranded DNA loop into which additional DNA segments can be linked. In another embodiment, the vector is a viral vector in which additional DNA segments can be linked into the viral genome. The vectors disclosed herein can replicate autonomously in the host cell into which they have been introduced (for example, bacterial vectors with bacterial origin of replication and episomal mammalian vectors) or can be integrated into the genome of the host cell after being introduced into the host cell, so as to replicate together with the host genome (for example, non-episomal mammalian vectors).

The methods for producing and purifying antibodies and antigen-binding fragments are well known in the prior art, such as Antibody Experiment Technical Guide, Cold Spring Harbor, Chapters 5-8 and 15. For example, mice can be immunized with human TSLP or fragment thereof, and the obtained antibodies can be renatured and purified, and amino acid sequencing can be performed by using conventional methods. Antigen-binding fragments can also be prepared by using conventional methods. The antibody or antigen-binding fragment according to the present disclosure is genetically engineered to add one or more human FR regions to the non-human CDR regions. The human FR germline sequences can be obtained from the ImmunoGeneTics (IMGT) website http://imgt.cines.fr by comparing the IMGT human antibody variable region germline gene database and MOE software, or be obtained from The Immunoglobulin FactsBook, 2001ISBN012441351.

The term "host cell" refers to a cell into which an expression vector has been introduced. Host cells can include bacteria, microorganisms, plant or animal cells. Bacteria that can be easily transformed include members of the enterobacteriaceae, for example *Escherichia coli* or *Salmonella* strains; Bacillaceae, for example *Bacillus subtilis*; Pneumococcus; *Streptococcus* and *Haemophilus influenzae*. Suitable microorganisms include *Saccharomyces cerevisiae* and *Pichia pastoris*. Suitable animal host cell lines include CHO (Chinese Hamster Ovary Cell Line), 293 cells and NSO cells.

The engineered antibodies or antigen-binding fragments of the present disclosure can be prepared and purified by conventional methods. For example, the cDNA sequences encoding the heavy chain and light chain can be cloned and recombined into a GS expression vector. The recombinant immunoglobulin expression vectors can stably transfect CHO cells. As a more recommended prior art, mammalian expression systems can lead to glycosylation of antibodies, especially in the highly conserved N-terminal sites of the Fc region. Stable clones are obtained by expressing antibodies that specifically bind to human TSLP. Positive clones are expanded in serum-free medium of bioreactors to produce antibodies. The medium into which the antibodies are secreted can be purified by conventional techniques. For example, using A or G Sepharose FF column with adjusted buffer for purification. Non-specifically bound components are washed off. Then the bound antibodies are eluted by the pH gradient method, and the antibody fragments are detected by SDS-PAGE and collected. The antibodies can be filtered and concentrated by conventional methods. Soluble mixtures and polymers can also be removed by conventional methods, for example molecular sieves and ion exchange. The resulting product needs to be frozen immediately, such as at −70° C., or lyophilized.

"Administering", "giving" and "treating", when applied to animals, humans, experimental subjects, cells, tissues, organs or biological fluids, refer to the contact of the exogenous medicament, therapeutic agent, diagnostic agent or composition with the animals, humans, subjects, cells, tissues, organs or biological fluids. "Administering", "giving" and "treating" can refer to for example treatment, pharmacokinetics, diagnosis, research and experimental methods. Treating cells includes contacting reagents with cells, and contacting reagents with fluids, wherein the fluids are in contact with the cells. "Administering", "giving" and "treating" also refer to treating for example cells by reagents, diagnosis, binding compositions or by another cell in vitro and ex vivo. "Treating" when applied to human, veterinary or research subjects, refers to therapeutic treatment, preventive or prophylactic measures, research and diagnostic applications.

"Treatment" refers to giving an internal or external therapeutic agent, for example a composition comprising any one of the binding compounds of the present disclosure, to a patient with one or more disease symptoms on which the therapeutic agent is known to have therapeutic effect. Generally, the therapeutic agent is given at an amount effective to alleviate one or more disease symptoms in the patient or population treated to induce the regression of such symptoms or inhibit the development of such symptoms to any clinically measurable extent. The amount of therapeutic agent that is effective to alleviate any specific disease symptom (also referred to as a "therapeutically effective amount") can vary according to a variety of factors, for example the patient's disease state, age and body weight, and the ability of the drug to produce the desired therapeutic effect in the patient. Whether the disease symptoms have been alleviated can be evaluated by any clinical testing methods commonly used by doctors or other health care professionals to evaluate the severity or progression of the symptoms. Although the embodiments of the present disclosure (for example treatment methods or products) may not be effective in alleviating the target disease symptom(s) in every patient, as determined according to any statistical testing methods known in the art, such as Student t-test, chi-square test, Mann and Whitney's U test, Kruskal-Wallis test (H test), Jonckheere-Terpstra test and Wilcoxon test, they should reduce the target disease symptom(s) in a statistically significant number of patients.

"Conservative modification" or "conservative replacement or substitution" refers to substitutions of amino acids in a protein with other amino acids having similar characteristics (e.g. charge, side-chain size, hydrophobicity/hydrophilicity, backbone conformation and rigidity, etc.), so that changes can be frequently made without changing the biological activity of the protein. Those skilled in the art know that, generally speaking, a single amino acid substitution in a non-essential region of a polypeptide does not substantially change the biological activity (see for example Watson et al. (1987) Molecular Biology of the Gene, The Benjamin/Cummings Pub. Co., Page 224, (4th edition)). In addition, the substitution of amino acids with similar structure or function is unlikely to disrupt the biological activity. Exemplary conservative substitutions are stated in the table "Exemplary amino acid conservative substitutions" below.

TABLE 5

Exemplary amino acid conservative substitutions

| Original residue | Conservative substitution |
|---|---|
| Ala (A) | Gly; Ser |
| Arg (R) | Lys; His |
| Asn (N) | Gln; His; Asp |
| Asp (D) | Glu; Asn |
| Cys (C) | Ser; Ala; Val |
| Gln (Q) | Asn; Glu |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |

TABLE 5-continued

Exemplary amino acid conservative substitutions

| Original residue | Conservative substitution |
|---|---|
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

"Effective amount" or "effective dose" refers to the amount of a drug, compound or pharmaceutical composition necessary to obtain any one or more beneficial or desired therapeutic results. For preventive use, the beneficial or desired results include elimination or reduction of risk, reduction of severity or delay of the disease onset, including the biochemistry, histology and/or behavioral symptoms of the disease, complications thereof and intermediate pathological phenotypes that appear during the developmental process of the disease. For therapeutic applications, the beneficial or desired results include clinical results, such as reducing the incidence of various target antigen-related disorders of the present disclosure or improving one or more symptoms of the disorder, reducing the dose of other agents required to treat the disorder, enhancing the therapeutic effect of another agent, and/or delaying the progression disorders of the patient related to the target antigen of the present disclosure.

"Exogenous" refers to substances produced outside organisms, cells or human bodies according to circumstances. "Endogenous" refers to substances produced inside cells, organisms or human bodies according to circumstances.

"Homology" refers to the sequence similarity between two polynucleotide sequences or between two polypeptides. When the positions in the two sequences compared are occupied by the same base or amino acid monomer subunit, for example if each position of two DNA molecules is occupied by adenine, then the molecules are homologous at that position. The homology percentage between two sequences is a function of the number of matched or homologous positions shared by the two sequences divided by the number of positions compared×100. For example, in the optimal sequence alignment, if 6 out of 10 positions in the two sequences are matched or homologous, then the two sequences are 60% homologous; if 95 out of 100 positions in the two sequences are matched or homologous, then the two sequences are 95% homologous. Generally, when aligning two sequences, comparisons are made to give the maximum percentage homology. For example, the comparison can be performed by the BLAST algorithm, wherein the parameters of the algorithm are selected to give the maximum match between each sequence over the entire length of each reference sequence. The following references relate to the BLAST algorithm that is often used for sequence analysis: BLAST ALGORITHMS: Altschul, S. F. et al., (1990) J. Mol. Biol. 215:403-410; Gish, W. et al., (1993) Nature Genet. 3:266-272; Madden, T. L. et al., (1996) Meth. Enzymol. 266:131-141; Altschul, S. F. et al., (1997) Nucleic Acids Res. 25:3389-3402; Zhang, J. et al., (1997) Genome Res. 7:649-656. Other conventional BLAST algorithms, such as those provided by NCBI BLAST, are also well known to those skilled in the art.

The expressions "cell", "cell line" and "cell culture" as used herein can be used interchangeably, and all such names include the progeny. Therefore, the words "transformant" and "transformed cell" include primary test cells and cultures derived therefrom, regardless of the number of passages. It should also be understood that due to deliberate or unintentional mutations, all offspring cannot be exactly the same in terms of DNA content. Mutant progeny with the same function or biological activity as screened in the original transformed cells is included. It is clearly visible from the context when a different name is referred to.

"Polymerase chain reaction" or "PCR" as used herein refers to a procedure or technique in which a trace amount of a specific moiety of nucleic acid, RNA and/or DNA is amplified as described in, for example, U.S. Pat. No. 4,683, 195. Generally speaking, it is necessary to obtain sequence information from the end or outside of the target region, so that oligonucleotide primers can be designed; these primers are the same or similar in terms of sequence to the corresponding strand of the template to be amplified. The 5' terminal nucleotides of the two primers can be identical to the ends of the material to be amplified. PCR can be used to amplify specific RNA sequences, specific DNA sequences from total genomic DNA and cDNA sequences transcribed from total cellular RNA, phage or plasmid sequences, etc. Generally, see Mullis et al. (1987) Cold Spring Harbor, Symp. Ouant. Biol. 51:263; Erlich ed., (1989) PCR TECHNOLOGY (Stockton Press, N.Y.). The PCR used herein is regarded as an example, but not the only example, of a nucleic acid polymerase reaction method for amplifying a nucleic acid test sample, and the method includes using known nucleic acids as primers and nucleic acid polymerases to amplify or produce a specific moiety of the nucleic acid.

"Isolated" refers to a purified state, and in this case means that the designated molecule is substantially free of other biomolecules, for example nucleic acids, proteins, lipids, carbohydrates or other materials, for example cell debris and growth medium. Generally, the term "isolated" is not intended to mean the complete absence of these materials or the absence of water, buffer or salt, unless they are present in an amount that significantly interferes with the experimental or therapeutic use of the compound as described herein.

"Optional" or "optionally" means that the event or environment described later can occur, but does not have to occur, and this description includes occasions where the event or environment occurs or does not occur.

"Pharmaceutical composition" means a mixture containing one or more of the compounds described herein or physiologically/pharmaceutically acceptable salts or prodrugs thereof, and other chemical components, for example physiological/pharmaceutically acceptable carriers and excipients. The purpose of the pharmaceutical composition is to promote the administration to organisms, which facilitates the absorption of the active ingredient and thereby exerts biological activity.

The term "pharmaceutically acceptable carrier" refers to any inactive substance suitable for use in a formulation for the delivery of antibodies or antigen-binding fragments. The carrier can be an anti-adhesive agent, binder, coating, disintegrant, filler or diluent, preservative (such as antioxidant, antibacterial or antifungal agent), sweetener, absorption delaying agent, wetting agent, emulsifier, buffer, etc. Examples of suitable pharmaceutically acceptable carriers include water, ethanol, polyol (for example glycerol, propanediol, polyethylene glycol, etc.), dextrose, vegetable oil (for example olive oil), saline, buffer, buffered saline, and isotonic agent for example sugar, polyol, sorbitol and sodium chloride.

In addition, the present disclosure includes agents for treating TSLP-related diseases, comprising the anti-TSLP antibody of the present disclosure or antigen-binding fragment thereof as an active ingredient.

There is no limitation for the TSLP-related disease in the present disclosure, as long as it is a disease related to TSLP. For example, the therapeutic response induced by the molecule of the present disclosure can be achieved by binding to human TSLP, and then blocking the binding of TSLP to its receptors, or killing cells overexpressing TSLP.

In addition, the present disclosure relates to methods for immunodetection or determination of the target antigen (for example TSLP), reagents for immunodetection or determination of the target antigen (for example TSLP), methods for immunodetection or determination of cells expressing the target antigen (for example TSLP) and diagnostic agents for diagnosing diseases related to target antigen (for example TSLP) positive cells, which includes the antibody or antibody fragment of the present disclosure as active ingredient, which specifically recognizes the target antigen (for example human TSLP) and binds with the amino acid sequence of the extracellular domain or three-dimensional structure thereof.

In the present disclosure, the method used for detection or measurement of the amount of the target antigen (for example TSLP) may be any known method. For example, it includes immunodetection or measurement methods.

The immunodetection or measurement methods are methods of detecting or measuring the amount of antibody or antigen using labeled antigens or antibodies. Examples of immunodetection or measurement methods include radioimmunoassay (RIA), enzyme immunoassay (EIA or ELISA), fluorescence immunoassay (FIA), luminescence immunoassay, western blotting, physicochemical methods, etc.

The aforementioned TSLP-related diseases can be diagnosed by detecting or measuring cells expressing TSLP by using the antibody or antibody fragment of the present disclosure.

In order to detect cells expressing the polypeptide, known immunodetection methods can be used, preferably using immunoprecipitation, fluorescent cell staining, immunohistochemical staining, etc. In addition, fluorescent antibody staining method utilizing the FMAT8100HTS system (Applied Biosystem) can be used.

In the present disclosure, there is no particular limitation for the in vivo sample used for detection or measurement of the target antigen (for example TSLP), as long as it has the possibility of comprising cells expressing the target antigen (for example TSLP), for example histocyte, blood, plasma, serum, pancreatic juice, urine, feces, tissue fluid or culture fluid.

According to the required diagnostic method, the diagnostic agent containing the monoclonal antibody or antibody fragment thereof of the present disclosure can also contain reagents for performing antigen-antibody reaction or reagents for detecting the reaction. The reagents used for performing the antigen-antibody reaction include buffers, salts, etc. The reagents used for detection include reagents commonly used in immunodetection or measurement methods, for example labeled second antibodies that recognize the monoclonal antibody, antibody fragment thereof or conjugate thereof, and substrates corresponding to the label, etc.

In the above specification, presented are the details of one or more embodiments of the present disclosure. Although any methods and materials similar or identical to those described herein can be used to implement or test the present invention, the preferred methods and materials are described below. The other features, purposes and advantages of the present disclosure will be obvious through the specification and the claims. In the specification and the claims, unless otherwise clearly indicated in the context, the singular form includes the cases of plural referent. Unless otherwise defined, all technical and scientific terms used herein have the general meanings understood by those of ordinary skill in the art to which the present invention belongs. All patents and publications cited in the specification are incorporated by reference. The following examples are presented to more comprehensively illustrate the preferred embodiments of the present invention. These examples should not be construed as limiting the scope of the present invention in any way, and the scope of the present invention is defined by the claims.

EXAMPLES

The examples below are incorporated for further description of the present disclosure, but these examples do not limit the scope of the present disclosure.

The experimental methods with unspecified conditions in the examples or test examples of the present disclosure generally follow conventional conditions, or according to the conditions recommended by the raw material or commodity manufacturer. See Sambrook et al., Molecular Cloning: A Laboratory Manual, Cold Spring Harbor; Current Protocols Molecular Biology, Ausubel et al., Greene Publishing Associates, Wiley Interscience, NY. The reagents with unspecified sources are conventional reagents purchased on the market.

Example 1. Expression of TSLP and TSLP Receptor

The sequences encoding His-tagged human TSLP and cyno TSLP, human IgG1-Fc-tagged human TSLP and cyno TSLP, and TSLP receptor extracellular domain sequences were loaded onto phr vector to construct expression plasmids, which were then transfected into HEK293. The specific transfection steps were as follows: on the previous day, HEK293E cells were seeded in Freestyle expression medium (containing 1% FBS) at $0.8 \times 10^6$/ml, placed on a 37° C. constant temperature shaker (120 rpm) and continued culturing for 24 hours. After 24 hours, the transfection plasmid and the transfection reagent PEI were sterilized with 0.22 μm filters. Then the transfection plasmid was adjusted to 100 μg/100 ml cells, and the mass ratio of PEI (1 mg/ml) and plasmid was 3:1. Taking the transfection of 200 ml HEK293E cells as an example, 10 ml of Opti-MEM and 200 μg plasmid were taken and mixed well, and let stand for 5 min; another 10 ml of Opti-MEM and 600 μg PEI were taken and mixed well, and let stand for 5 min. The plasmid and PEI were mixed well and let stand for 15 min, better not exceeding 20 min. The mixture of the plasmid and PEI was slowly added to 200 ml HEK293E cells, and placed on a shaker at 8% $CO_2$, 120 rpm and 37° C. for culturing. On day 3 of transfection, the culture was supplemented with 10% volume of supplemented medium. Until day 6 of transfection, samples were taken and centrifuged at 4500 rpm for 10 min to collect the cell supernatant. The supernatant was filtered and purified to obtain the recombinant TSLP and TSLP receptor proteins through Example 2. The purified proteins could be used in the experiments of each example below. The relevant sequences are as follows.

1. Amino acid sequence of his-tagged human TSLP antigen (huTSLP-his)

SEQ ID NO: 1

<u>MFPFALLYVLSVSFRKIFILQLVGLVLT</u>YDFTNCDFEKIKAAYLSTISKDLITYMS

GTKSTEFNNTVSCSNRPHCLTEIQSLTFNPTAGCASLAKEMFAMKTKAALAIW

CPGYSETQINATQAMKKARKSKVTTNKCLEQVSQLQGLWRRFNRPLLKQQ*GS*

*SDYKDDDDKHHHHHH*
Note:
Underlined is the signal peptide sequence; the italicized part is the Flag-His6-tag.

2. Amino acid sequence of Fc-tagged human TSLP antigen (huTSLP-Fc)

SEQ ID NO: 2

<u>MFPFALLYVLSVSFRKIFILQLVGLVLT</u>YDFTNCDFEKIKAAYLSTISKDLITYMS

GTKSTEFNNTVSCSNRPHCLTEIQSLTFNPTAGCASLAKEMFAMKTKAALAIW

CPGYSETQINATQAMKKARKSKVTTNKCLEQVSQLQGLWRRFNRPLLKQQ*DI*

*EGRMDEPKSSDKTHTCPPCPAPELLGGPSVFLFPPKPKDTLMISRTPEVTCVVVDV*

*SHEDPEVKFNWYVDGVEVHNAKTKPREEQYNSTYRVVSVLTVLHQDWLNGKEYK*

*CKVSNKALPAPIEKTISKAKGQPREPQVYTLPPSRDELTKNQVSLTCLVKGFYPSDIA*

*VEWESNGQPENNYKTTPPVLDSDGSFFLYSKLTVDKSRWQQGNVFSCSVMHEALH*

*NHYTQKSLSLSPGK*
Note:
Underlined is the signal peptide sequence; the italicized part is the linker-human Fc-tag.

3. Amino acid sequence of his-tagged cyno TSLP antigen (cynoTSLP-his)

SEQ ID NO: 3

<u>METDTLLLWVLLLWVPGSTG</u>YDFTNCDFQKIEADYLRTISKDLITYMSGTKST

DFNNTVSCSNRPHCLTEIQSLTFNPTPRCASLAKEMFARKTKATLALWCPGYSE

TQINATQAMKKARKSKVTTNKCLEQVSQLLGLWRRFIRTLLKQQ*GSSDYKDD*

*DDKHHHHHH*
Note:
Underlined is the signal peptide sequence; the italicized part is the flag-His6-tag.

4. Amino acid sequence of Fc-tagged cyno TSLP antigen (cynoTSLP-Fc)

SEQ ID NO: 4

<u>METDTLLLWVLLLWVPGSTG</u>YDFTNCDFQKIEADYLRTISKDLITYMSGTKST

DFNNTVSCSNRPHCLTEIQSLTFNPTPRCASLAKEMFARKTKATLALWCPGYSE

TQINATQAMKKARKSKVTTNKCLEQVSQLLGLWRRFIRTLLKQQ*DIEGRMDE*

*PKSSDKTHTCPPCPAPELLGGPSVFLFPPKPKDTLMISRTPEVTCVVVDVSHEDPE*

*VKFNWYVDGVEVHNAKTKPREEQYNSTYRVVSVLTVLHQDWLNGKEYKCKVSNK*

*ALPAPIEKTISKAKGQPREPQVYTLPPSRDELTKNQVSLTCLVKGFYPSDIAVEWES*

*NGQPENNYKTTPPVLDSDGSFFLYSKLTVDKSRWQQGNVFSCSVMHEALHNHYT*

*QKSLSLSPGK*
Note:
Underlined is the signal peptide sequence; the italicized part is the linker-human Fc-tag.

5. Amino acid sequence of Fc-tagged human TSLP receptor extracellular domain (human-TSLPR-Fc-ECD):

SEQ ID NO: 5

<u>GAAEGVQIQIIYFNLETVQVTWNASKYSRTNLTFHYRFNGDEAYDQCTNYLL</u>

<u>QEGHTSGCLLDAEQRDDILYFSIRNGTHPVFTASRWMVYYLKPSSPKHVRFSW</u>

<u>HQDAVTVTCSDLSYGDLLYEVQYRSPFDTEWQSKQENTCNVTIEGLDAEKCY</u>

<u>SFWVRVKAMEDVYGPDTYPSDWSEVTCWQRGEIRDACAETPTPPKPKLSK</u>*DI*

*SHEDPEVKFNWYVDGVEVHNAKTKPREEQYNSTYRWSVLTVLHQDWLNGKEYK*

-continued

*CKVSNKALPAPIEKTISKAKGQPREPQVYTLPPSRDELTKNQVSLTCLVKGFYPSDIA*

*VEWESNGQPENNYKTFPPVLDSDGSFFLYSKLTVDKSRWQQGNVFSCSVMHEALH*

*NHYTQKSLSLSPGK*

Note:
The underlined part is the human-TSLPR extracellular domain, and the italicized part is linker-human Fc-tag.

Example 2. Purification of TSLP and TSLP Receptor (TSLPR) Recombinant Proteins

2.1 Purification of His-Tagged TSLP Recombinant Proteins of Each Species

The cell expression supernatant samples were centrifuged at high speed to remove impurities and filtered. Nickel columns were equilibrated with PBS solution and washed with 10 times of the column volume. The filtered supernatant samples were applied to the columns. The columns were washed with PBS solution containing 30 mM imidazole until the $A_{280}$ reading dropped to baseline. The target proteins were then eluted with PBS solution containing 300 mM imidazole, and the elution peaks were collected. The proteins were concentrated and exchanged into PBS, and aliquoted for use after being identified as correct by LC-MS. Obtained were his-tagged human TSLP and cyno TSLP.

2.1 Purification of Human Fc-Tagged TSLP of Each Species and Human TSLP Receptor Extracellular Domain Recombinant Proteins The cell expression supernatant samples were centrifuged at high speed to remove impurities. The recombinant antibody expression supernatant was purified by Protein A columns. The columns were washed with PBS until the A280 reading dropped to baseline. The target proteins were eluted with 100 mM acetate buffer pH 3.5, and neutralized with 1 M Tris-HCl pH 8.0. The obtained proteins were concentrated and exchanged into new solution, and aliquoted for use after being identified as correct by electrophoresis and LC-MS.

Example 3. Construction and Identification of Recombinant TSLP Receptor and IL7Rα Receptor Cell Lines In order to screen antibodies that can block TSLP from binding to TSLP receptor, CHO-K1 and BaF3 cell lines simultaneously expressing both human TSLP receptor and human IL7Rα (TSLPR/IL7Rα) were constructed. Lentivirus was used to package the target gene TSLPR/IL7 Rα and cloned into the target cell lines to form stable high-expressing cell lines. Firstly, human TSLPR and human IL7Rα genes were cloned into the plasmids pCDH-CMV-MCS-EF1-puro and pCDH-CMV-MCS-EF1-Neo (SBI, CD500B-1) respectively. Then the lentivirus infection method was used to insert human TSLPR into CHO-K1 and BaF3 cell lines, which were cultured under the selection pressure of 10 μg/ml puromycin (Gibco, US) for three weeks. Then, the second round of infection was carried out. The human IL7Rα gene was inserted into the cell lines and screened with 1 mg/ml G418 (Gibco, US) and 10 μg/ml puromycin for two to three weeks. Finally, CHO-K1 and BaF3 monoclonal cell lines with simultaneous high expression of TSLPR and IL7Rα were screened out by the flow sorting method.

Example 4. Preparation and Screening of Anti-Human TSLP Antibodies

Anti-human TSLP monoclonal antibodies were produced by immunizing laboratory SJL white mice, female, 6-8 weeks old (Beijing Charles River Laboratory Animal Technology Co., Ltd., animal production license number: SCXK (Beijing) 2012-0001). Housing environment: SPF level. After the mice were purchased, they were kept in a laboratory environment for 1 week, with 12/12 hours light/dark cycle adjustment, temperature 20-25° C.; humidity 40-60%. Mice that had adapted to the environment were immunized with recombinant proteins huTSLP-Fc (25 μg), huTSLP-his (12.5 μg) and cyno TSLP-his (12.5 μg) and TiterMax, Alum or CpG adjuvant. After 4-5 immunizations, mice with high antibody titers in the serum and the titers tending to reach a plateau were selected and sacrificed. The spleen cells were collected and fused with myeloma cells. Splenic lymphocytes and the myeloma cell Sp2/0 cells (ATCC® CRL-8287™) were fused to obtain hybridoma cells by using optimized PEG-mediated fusion steps.

For the initial screening, ELISA binding assays for human and cyno TSLP, assays of blocking human TSLP from binding to its receptor TSLPR, and experiments of inhibiting TSLP-induced proliferation of BaF3 cells were performed. After transferring the hybridoma cells to 24-well plates, the supernatant was re-screened. Hybridoma clones were obtained after two rounds of subcloning of the selected positive clones, and were used for antibody production and purification was performed by affinity methods.

The monoclonal hybridoma cell lines No. 3, No. 119, No. 179 and No. 199 with good activity were obtained after screening, and the hybridoma cells in logarithmic growth phase were collected. RNA was extracted with NucleoZol (MN), and reverse transcription was performed (PrimeScript™ Reverse Transcriptase, Takara, cat #2680A). The cDNA obtained by reverse transcription was amplified by PCR using mouse Ig-Primer Set (Novagen, TB326 Rev.B 0503) and sent to a sequencing company for sequencing. Murine anti-TSLP antibodies were obtained after sequencing: mab3, mab119, mab179 and mab199 sequences, the amino acid sequence of the variable regions thereof are as follows:

```
>mab3 murine heavy chain variable region sequence:
                                          SEQ ID NO: 6
```
*EVQLQQSGPVLVKPGASVKMSCKASGYTFT<u>DDYMN</u>WVKQSHGKSLEWIG<u>IISPYN</u>*

*<u>GGTSYNQKFKG</u>KATLTVDKSSSTAYMELNSLTSEDSAVYYCAR<u>EDYDYDGYAMDH</u>*

*WGQGTSVTVSS*

-continued

```
>mab3 murine light chain variable region sequence:
                                              SEQ ID NO: 7
QIVLSQSPAILSASPGEKVTMTCRASSSVSYMHWYQQKPGSSPKPWIYATSNLASGV

PARFSGSGSGTSYSLTISRVEAEDAATYYCQQWSSNRTFGGGTKLEIK

>mab11 murine heavy chain variable region sequence:
                                              SEQ ID NO: 8
QAYLQQSGAELVRPGASVKMSCKASGFAFTTYNMHWVKHTPGQGLEWIGAIYPG

NGETSYNQKFKDRATLTVDKSSRTAYMQLSSLTSEDSAVYFCAREDDYGEGYFDV

WGAGTTVTVSS

>mab119 murine light chain variable region sequence:
                                              SEQ ID NO: 9
DIVLTQSPASLAVSLGQRATISCRASESVDNSGLSFMHWYQQKPGQPPRLLLYRASN

LGSGIPARFSGSGSGTDFTLTLNPVETDDVATYYCQQINTDPLTFGAGTKLELK

>mab179 murine heavy chain variable region sequence:
                                              SEQ ID NO: 10
QVQLQQSGAELVRPGTSVKVSCKASGYAFTNYLIEWVKQRPGQGLEWIGVIDPGN

GDTNYNENFKGKATLTADKSSSTAYIELSRLTSEDSAVYFCAREDNTGTAFDYWGQ

GTTLTVSS

>mab179 murine light chain variable region sequence:
                                              SEQ ID NO: 11
SIVMTQTPKFLLVSAGDRVTISCKASQSVSSDVTWYQQKPGQSPKLLIYYVSNHYTG

VPDRFTGSGYGTDFTFTISSVQAEDLAVYFCQQHHRFPLTFGAGTKLELK

>mab199 murine heavy chain variable region sequence:
                                              SEQ ID NO: 12
QVQLQQSGPQLVRPGASVKISCKASGYSFTTYWMHWVKQRPGQGLEWIGMIDPS

DSETTLIQKFKDKATLTVDKSSSTAYMQLSSPTSEDSAVYYCARTLDGYYDYWGQG

TTLTVSS

>mab199 murine light chain variable region sequence:
                                              SEQ ID NO: 13
DIQMTQSPASLSASVGETVTITCRASENIYSYLAWYQQKQGKSPQLLVYFAKTLAEG

VPSRFSGSVSGTQFSLKINSLQPEDFGSYYCQHHYGTPWTFGGGTKLEIK
```

The amino acid sequences of the CDR regions obtained according to the Kabat numbering rules are shown in the following table:

TABLE 6

Sequences of heavy chain and light chain CDR regions of antibodies from hybridoma clones

| Antibody | Heavy chain | | Light chain | |
|---|---|---|---|---|
| mab3 | HCDR1 | DDYMN<br>SEQ ID NO: 14 | LCDR1 | RASSSVSYMH<br>SEQ ID NO: 17 |
| | HCDR2 | IISPYNGGTSYNQKFKG<br>SEQ ID NO: 15 | LCDR2 | ATSNLAS<br>SEQ ID NO: 18 |
| | HCDR3 | EDYDYDGYAMDH<br>SEQ ID NO: 16 | LCDR3 | QQWSSNRT<br>SEQ ID NO: 19 |
| mab119 | HCDR1 | TYNMH<br>SEQ ID NO: 20 | LCDR1 | RASESVDNSGLSFMH<br>SEQ ID NO: 23 |
| | HCDR2 | AIYPGNGETSYNQKFKD<br>SEQ ID NO: 21 | LCDR2 | RASNLGS<br>SEQ ID NO: 24 |
| | HCDR3 | EDDYGEGYFDV<br>SEQ ID NO: 22 | LCDR3 | QQINTDPLT<br>SEQ ID NO: 25 |

TABLE 6-continued

Sequences of heavy chain and light chain CDR regions of antibodies from hybridoma clones

| Antibody | | Heavy chain | | Light chain |
|---|---|---|---|---|
| mab179 | HCDR1 | NYLIE<br>SEQ ID NO: 26 | LCDR1 | KASQSVSSDVT<br>SEQ ID NO: 29 |
| | HCDR2 | VIDPGNGDTNYNENFKG<br>SEQ ID NO: 27 | LCDR2 | YVSNHYT<br>SEQ ID NO: 30 |
| | HCDR3 | EDNTGTAFDY<br>SEQ ID NO: 28 | LCDR3 | QQHHRFPLT<br>SEQ ID NO: 31 |
| mab199 | HCDR1 | TYWMH<br>SEQ ID NO: 32 | LCDR1 | RASENIYSYLA<br>SEQ ID NO: 35 |
| | HCDR2 | MIDPSDSETTLIQKFKD<br>SEQ ID NO: 33 | LCDR2 | FAKTLAE<br>SEQ ID NO: 36 |
| | HCDR3 | TLDGYYDY<br>SEQ ID NO: 34 | LCDR3 | QHHYGTPWT<br>SEQ ID NO: 37 |

Chimeric antibodies were formed by linking the light and heavy chain variable regions of the aforementioned murine antibody with the light and heavy chain constant regions of the human antibody (such as the kappa constant region as shown in SEQ ID NO: 134 and the IgG1-YTE constant region as shown in SEQ ID NO: 133). The chimeric antibody corresponding to clone mab3 was named Ch3, and so forth for other antibodies.

Example 5. Design of Humanization of Anti-Human TSLP Monoclonal Antibodies

In order to reduce the immunogenicity of murine antibodies, the screened mab3, mab119, mab179 and mab199 antibodies with excellent in vivo and in vitro activities were humanized. Humanization of the murine monoclonal antibodies was performed according to the methods published in many documents in the art. Briefly, human antibody constant domains were used to replace parental (murine antibody) constant domains, human germline antibody sequences were selected according to the homology between the murine and human antibodies, and CDR grafting was performed. Then, based on the three-dimensional structure of the murine antibody, the amino acid residues of VL and VH were subjected to back-mutation, and the constant regions of the murine antibody were replaced with human constant regions, resulting in the final humanized molecule.

5.1 Selection and Back Mutations of the Human FR Regions for Mab3

(1) Selection and Back Mutations of the Human FR Regions

For mab3, the humanized VH template was IGHV1-3*01+IGHJ6*01, and the humanized VL template was IGKV3-20+IGKJ4*01. The CDRs of mab3 were grafted to the human template, and the variable region sequences obtained after grafting are as follows:

hu3 VL-CDR grafted:
SEQ ID NO: 38
EIVLTQSPATLSLSPGERATLSCRASSSVSYMHWYQQKPGQAPRLLIY

ATSNLASGIPARFSGSGSGTDFTLTISRLEPEDFAVYYCQQWSSNRTF

GGGTKVEIK hu3 VH-CDR grafted:
SEQ ID NO: 42
EVQLVQSGALVKKPGASVKVSCKASGYIIDDYMNWVRQAPGQRLEW

MGIISPYNGGTSYNQKFKGRVTITRDTSASTAYMELSSLRSEDTAVYY

CAREDYDYDGYAMDHWGQGTTVTSS

Back mutation design of the mab3 humanized antibody is as shown in the following table:

TABLE 7

Back mutations of the mab3 humanized antibody

| hu3VL | | hu3VH | |
|---|---|---|---|
| hu3VL1 | Grafted | hu3VH1 | Grafted |
| hu3VL2 | L46P, F71Y | hu3VH2 | I69L, R71V, T73K |
| hu3VL3 | L46P, L47W, I58V, F71Y | hu3VH3 | R38K, M48I, V67A, I69L, R71V, T73K |
| hu3VL4 | L46P, L47W, I58V, D70S, F71Y | | |

Note:
Grafted represents grafting the murine antibody CDRs into the human germline FR region sequences. L46P represents that according to the Kabat numbering system, the L at position 46 is mutated back to P.

The sequences of the variable regions of the mab3 humanized antibody are as follows:

>hu3VL1 (hu3 VL-CDR grafted)
SEQ ID NO: 38
EIVLTQSPATLSLSPGERATLSCRASSSVSYMHWYQQKPGQAPRLLIYAT

SNLASGIPARFSGSGSGTDYTLTISRLEPEDFAVYYCQQWSSNRTFGGGT

KVEIK

>hu3VL2
SEQ ID NO: 39
EIVLTQSPATLSLSPGERATLSCRASSSVSYMHWYQQKPGQAPRLIYAT

SNLASGIPARFSGSGSGTDYTLTISRLEPEDFAVYYCQQWSSNRTFGGGT

KVEIK

>hu3VL3
SEQ ID NO: 40
EIVLTQSPATLSLSPGERATLSCRASSSYSYMHWYQQKPGQAPRPWIYAT

SNLASGVPARFSGSGSGTDYTLTISRLEPEDFAVYYCQQWSSNRTFGGGT

KVEIK

-continued

>hu3VL4
SEQ ID NO: 41
EIVLTQSPATLSLSPGERATLSCRASSSYSYMHWYQQKPGQAPRPWIYAT

SNLASGVPARFSGSGSGTSYTLTISRLEPEDFAVYYCQQWSSNRTFGGGT

KVEIK

>hu3VH1 (hu3 VH-CDR Grafted)
SEQ ID NO: 42
EVQLVQSGAEVKKPGASVKVSCKASGYTFTDDYMNWVRQAPGQRLEWMGI

ISPYNGGTSYNQKFKGRVTITRDTSASTAYMELSSLRSEDTAVYYCARED

YDYDGYAMDHWGQGTTVTVSS

>hu3VH2
SEQ ID NO: 43
EVQLVQSGAEVKKPGASVKVSCKASGYTFTDDYMNWVRQAPGQRLEWMGI

ISPYNGGTSYNQKFKGRVTLTVDKSASTAYMELSSLRSEDTAVYYCARED

YDYDGYAMDHWGQGTTVTVSS

>hu3VH3
SEQ ID NO: 44
EVQLVQSGAEVKKPGASVKVSCKASGYTFTDDYMNWVKQAPGQRLEWIGI

ISPYNGGTSYNQKFKGRATLTVDKSASTAYMELSSLRSEDTAVYYCARED

YDYDGYAMDHWGQGTTVTVSS

Note:
The single underline represents CDR regions, and the double underline represents back mutation sites.

The aforementioned light and heavy chain variable regions were combined with human germline light and heavy chain constant region sequences to form the final complete light and heavy chain sequences, thus obtaining the antibody with full-length sequence. Exemplarily, for the mab3 humanized antibody in the present disclosure, the heavy chain constant region is the IgG1-YTE constant region shown in SEQ ID NO: 133, and the light chain constant region is the kappa chain constant region shown in SEQ ID NO: 134, but they can also be replaced with other constant regions known in the art.

The sequences of the heavy and light chain variable regions of the obtained mab3 humanized antibodies are shown in the following table:

TABLE 8

Heavy and light chain variable region sequences of mab3 humanized antibody

| Antibody | VH (SEQ ID No.) | VL (SEQ ID No.) |
|---|---|---|
| hu3-01 | 42 | 39 |
| hu3-02 | 42 | 40 |
| hu3-03 | 42 | 41 |
| hu3-04 | 43 | 38 |
| hu3-05 | 43 | 39 |
| hu3-06 | 43 | 40 |
| hu3-07 | 43 | 41 |
| hu3-08 | 44 | 39 |
| hu3-09 | 44 | 40 |
| hu3-10 | 44 | 41 |

The binding activity of mab3 humanized antibody to human TSLP was detected by ELISA method, and the results showed that mab3 humanized antibodies have very good binding ability to human TSLP.

(2) Point Mutation to Hu3 Antibody

It was found by detection that there were hot spots on the MDH sequence of HCDR3 and the NTR sequence of LCDR3 of the mab3 humanized antibody. Therefore, the corresponding hot spots were mutated. The sequences of the CDR regions of the mab3 humanized antibodies obtained after mutation are as follows:

TABLE 9

HCDR3 and LCDR3 sequences after mutation

| hu3 HCDR3-H110Y | EDYDYDGYAMDY |
| | SEQ ID NO: 45 |
| hu3LCDR3-N93D | QQWSSDRT |
| | SEQ ID NO: 46 |

Note:
The positions of mutation sites in Table 9 are numbered according to the natural order of the variable region sequences.

It can be concluded that the CDR sequences of the mab3 humanized antibody are as follows:

TABLE 10

CDRs after mutation of mab3 humanized antibody

| | Heavy chain | | Light chain |
|---|---|---|---|
| HCDR1 | DDYMN | LCDR1 | RASSSVSYMH |
| | SEQ ID NO: 14 | | SEQ ID NO: 17 |
| HCDR2 | IISPYNGGTSYNQKFKG | LCDR2 | ATSNLAS |
| | SEQ ID NO: 15 | | SEQ ID NO: 18 |
| HCDR3 (general formula) | EDYDYDGYAMDX1 SEQ ID NO: 47 | LCDR3 (general formula 1) | QQWSSX2RT SEQ ID NO: 48 |

Wherein, $X_1$ is selected from H or Y, $X_2$ is selected from N or D.

Exemplarily, the CDRs and heavy and light chain variable regions of the humanized antibody hu3-11 obtained after mutation are as follows:

TABLE 11

CDR regions of hu3-11

| | Heavy chain | | Light chain |
|---|---|---|---|
| HCDR1 | DDYMN | LCDR1 | RASSSVSYMH |
| | SEQ ID NO: 14 | | SEQ ID NO: 17 |
| HCDR2 | IISPYNGGTSYNQKFKG | LCDR2 | ATSNLAS |
| | SEQ ID NO: 15 | | SEQ ID NO: 18 |
| HCDR3-H110Y | EDYDYDGYAMDY SEQ ID NO: 45 | LCDR3-N93D | QQWSSDRT SEQ ID NO: 46 |

>Light chain variable region of hu3-11 (hu3VL4-N93D)
SEQ ID NO: 49
EIVLTQSPATLSLSPGERATLSCRASSSVSYMHWYQQKPGQAPRPWIYAT

SNLASGVPARFSGSGSGTSYTLTISRLEPEDFAVYYCQQWSSDRTFGGGT

KVEIK

-continued

>Heavy chain variable region of hu3-11
(hu3VH2-H110Y)
SEQ ID NO: 50
EVQLVQSGAEVKKPGASVKVSCKASGYTFT<u>DDYMN</u>WVRQAPGQRLEWMG<u>I</u>

<u>ISPYNGGTSYNQKFKG</u>RVT<u>L</u>T<u>V</u>D<u>K</u>SASTAYMELSSLRSEDTAVYYCARE<u>D</u>

<u>YDYDGYAMDY</u>WGQGTTVTVSS

The light and heavy chain variable regions after hot spot mutation were recombined with human germline light and heavy chain constant region sequences to form complete light and heavy chain sequences, thus obtaining the antibody with full-length sequence.

The binding activity of the antibody obtained after mutation to human TSLP was detected by using ELISA method. The results showed that the affinity activity of hu3-11 to human TSLP is still high, indicating that the hot spot mutations on the HCDR3 and LCDR3 of the mab3 humanized antibody do not affect the activity of antibody.

(3) Affinity Maturation of Hu3-11 Antibody

The hu3-11 molecule was subjected to affinity maturation. The process of affinity maturation was as follows:

Construction of the yeast library: degenerate primers were designed, and the designed mutant amino acids were introduced into the antibody hu3-11 scFv mutant libraries by PCR method, with the size of each library of about 109. The constructed yeast libraries were verified for their diversity by sequencing method.

In the first round of screening, about 5×10$^{10}$ cells from the hu3-11-scFv mutant libraries and biotinylated TSLP-Fc protein (1-10 μg/ml) were incubated in 50 ml 0.1% bovine serum albumin (BSA)-containing phosphate buffered saline (PBSA) for 1 hour at room temperature. Then, the mixture was washed with 0.1% PBSA to remove unbound antibody fragments. Then, 100 μl of streptomycin beads (Milenyi Biotec, Auburn, CA) were added to the hu3-11-scFv antibody mutant libraries bound to the biotinylated TSLP-Fc, and were loaded on the AutoMACS system for sorting. The cells with high affinity to TSLP-Fc were collected from the antibody library and induced at 250 rpm and 20° C. for 18 h. The obtained enriched library was subjected to the second round of screening against biotinylated recombinant TSLP-Fc protein.

For the third and fourth rounds of screening, the library cells from the previous round were incubated with biotinylated recombinant TSLP-Fc protein (0.1-1 μg/ml) and 10 μg/ml Mouse Anti-cMyc (9E10, sigma) antibody in 0.1% PBSA at room temperature for 1 h. The mixture was washed with 0.1% PBSA to remove unbound antibody fragments. Goat anti-mouse-Alexa488 (A-11001, life technologies) and Streptavidin-PE (S-866, Life technologies) were added and incubated at 4° C. for 1 h. The mixture was washed with 0.1% PBSA to remove unbound antibody fragments. Finally, antibodies with high affinity were screened out by FACS screening (BD FACSAria™ FUSION).

The hu3-11-scFv mutant libraries underwent 2 rounds of MACS screening and 2 rounds of FACS screening by utilizing biotinylated TSLP-Fc antigen. About 400 yeast single clones were then selected for culturing and inducing expression. The binding of yeast single clones to TSLP-Fc antigen was detected by using FACS, and yeast single clones with high affinity were selected and subjected to sequencing verification. The sequenced clones were compared and analyzed. After removing redundant sequences, the non-redundant sequences were converted into full-length antibodies for mammalian cell expression.

The sequences of the light chain variable regions obtained by affinity maturation are as follows:

>hu3VL5
SEQ ID NO: 51
EIVLTQSPATLSLSPGERATLSC<u>RASSSVSYMH</u>WYQQKPGQAPR<u>PWIYAT</u>

<u>SNLAS</u>G<u>V</u>PARFSGSGSGT<u>SY</u>TLTISRLEPEDFAVYYC<u>QQSDNVRG</u>FGGGT

KVEIK

>hu3VL6
SEQ ID NO: 52
EIVLTQSPATLSLSPGERATLSC<u>RASSSVSYMH</u>WYQQKPGQAPR<u>PWIYAT</u>

<u>SNLAS</u>G<u>V</u>PARFSGSGSGT<u>SY</u>TLTISRLEPEDFAVYYC<u>QQSDSGRE</u>FGGGT

KVEIK

The obtained light chain variable regions were recombined with the heavy chain variable regions of the mab3 humanized antibody to obtain a new mab3 humanized antibody. Exemplarily, huVL5 and huVL6 were respectively combined with hu3VH2-H110Y to obtain the new antibody molecules hu3-12 and hu3-13, which in details are as shown follows:

TABLE 12

Antibodies obtained by affinity maturation

| Antibody | hu3VH | hu3VL |
|---|---|---|
| hu3-12 | hu3VH2-H110Y | hu3VL5 |
| hu3-13 | hu3VH2-H110Y | hu3VL6 |

The CDR sequences of the mab humanized antibody obtained after affinity maturation are shown as follows:

TABLE 13

Antibody CDRs of mab3 humanized antibody obtained by affinity maturation

| Antibody | Heavy chain | | Light chain | |
|---|---|---|---|---|
| hu3-12 | HCDR1 | DDYMN SEQ ID NO: 14 | LCDR1 | RASSSVSYMH SEQ ID NO: 17 |
| | HCDR2 | IISPYNGGTSYNQ KFKG SEQ ID NO: 15 | LCDR2 | ATSNLAS SEQ ID NO: 18 |
| | HCDR3-H110Y | EDYDYDGYAMDY SEQ ID NO: 45 | LCDR3-V1 | QQSDNVRG SEQ ID NO: 53 |
| hu3-13 | HCDR1 | DDYMN SEQ ID NO: 14 | LCDR1 | RASSSVSYMH SEQ ID NO: 17 |
| | HCDR2 | IISPYNGGTSYNQ KFKG SEQ ID NO: 15 | LCDR2 | ATSNLAS SEQ ID NO: 18 |
| | HCDR3-H110Y | EDYDYDGYAMDY SEQ ID NO: 45 | LCDR3-V2 | QQSDSGRE SEQ ID NO: 54 |

The obtained new antibody mab3 humanized antibody was subjected to ELISA to detect its binding activity to human TSLP. The results showed that hu3-12 and hu3-13 still have high binding ability to human TSLP. It showed that changes of LCDR3 would not affect the activity of the hu3 series of antibodies.

In summary, the CDRs of the mab3 humanized antibody have the sequences shown as follows:

TABLE 14

General formula sequences of CDR regions of mab3 humanized antibody

| Heavy chain | | Light chain | |
|---|---|---|---|
| HCDR1 | DDYMN SEQ ID NO: 14 | LCDR1 | RASSSVSYMH SEQ ID NO: 17 |
| HCDR2 | IISPYNGGTSYNQ KFKG SEQ ID NO: 15 | LCDR2 | ATSNLAS SEQ ID NO: 18 |
| HCDR3 (general formula) | EDYDYDGYAMDX$_1$ SEQ ID NO: 47 | LCDR3 (general formula 2) | QQSDX$_3$X$_4$RX$_5$ SEQ ID NO: 55 |

Wherein, $X_1$ is H or Y, $X_3$ is N or S, $X_4$ is V or G, $X_5$ is G or E.

The combinations of the antibody heavy and light chain variable regions of the mab3 humanized antibody after hot spot mutation and affinity maturation are shown in the following table:

TABLE 15

Sequences of antibodies after affinity maturation

| Antibody | VH (SEQ ID NO) | VL (SEQ ID NO) |
|---|---|---|
| hu3-11 | 50 | 49 |
| hu3-12 | 50 | 51 |
| hu3-13 | 50 | 52 |

5.2 Selection and Back Mutations of the Human FR Regions for Mab119

For mab119, IGHV1-69*02 and HJ6*01 were selected as templates for the VH, and IGKV4-1*01 and IGKJ2*01 as well as IGKV3-11*01 and IGKJ2*01 were selected as templates for the VL. The CDR regions of the murine antibody were grafted to the selected humanized templates, and the FR regions were subjected to back mutation to obtain different light chain and heavy chain variable regions. The variable region sequences obtained by CDR grafting are as follows:

>hu119-VL CDR (Grafted, IGKV4-1*01)
SEQ ID NO: 56
DIVMTQSPDSLAVSLGERATINCRASESVDNSGLSFMHWYQQKPGQPPKL

LIYRASNLGSGVPDRFSGSGSGTDFTLTISSLQAEDVAVYYCQQINTDPL

TFGQGTKLEIK

>hu119VL4 (Grafted, IGKV3-11*01)
SEQ ID NO: 59
EIVLTQSPATLSLSPGERATLSCRASESVDNSGLSFMHWYQQKPGQAPRL

LIYRASNLGSGIPARFSGSGSGTDFTLTISSLEPEDFAVYYCQQINTDPL

TFGQGTKLEIK

>hu119-VH CDR (Grafted, IGHV1-69*02)
SEQ ID NO: 62
EVQLVQSGAEVKKPGSSVKVSCKASGGTFSTYNMHWVRQAPGQGLEWMGA

IYPGNGETSYNQKFKDRVTITADKSTSTAYMELSSLRSEDTAVYYCARED

DYGEGYFDVWGQGTTVTVSS

Back mutations of the mab119 humanized antibody are as shown in the following table:

TABLE 16

Back mutations of mab119

| | hu119VL | | hu119VH |
|---|---|---|---|
| hu119VL1 | Grafted (IGKV4-1*01) | hu119VH1 | Grafted (IGHV1-69*02) |
| hu119VL2 | Grafted (IGKV4-1*01) + M4L | hu119VH2 | G27F, I69L, A71V |
| hu119VL3 | Grafted (IGKV4-1*01) + I48L, V58I | hu119VH3 | G27F, M48I, V67A, I69L, A71V |
| hu119VL4 | Grafted (IGKV3-11*01) | hu119VH4 | G27F, R38K, Q39H, M48I, V67A, I69L, A71V |
| hu119VL5 | Grafted (IGKV3-11*01) + A43P, I48L | hu119VH5 | M48I, V67A, I69L, A71V |
| hu119VL6 | Grafted (IGKV3-11*01) + E1D, A43P, I48L | hu119VH6 | V2A, G27F, M48I, V67A, I69L, A71V |
| | | hu119VH7 | M48I, V67A, I69L, A71V, S76R |
| | | hu119VH8 | V2A, G27F, M48I, V67A, I69L, A71V, S76R |

Note:

For example, M4L represents that according to the Kabat numbering system, M at position 4 is mutated back to L. Grafted represents that the murine antibody CDR is implanted into the human germline FR region sequence.

The specific sequences of the variable regions of the mab119 humanized antibody are as follows:

>hu119VL1 (Grafted (IGKV4-1*01))
SEQ ID NO: 56
DIVMTQSPDSLAVSLGERATINCRASESVDNSGLSFMHWYQQKPGQPPKL
LIYRASNLGSGVPDRFSGSGSGTDFTLTISSLQAEDVAVYYCQQINTDPL
TFGQGTKLEIK >hu119VL2
SEQ ID NO: 57
DIVLTQSPDSLAVSLGERATINCRASESVDNSGLSFMHWYQQKPGQPPKL
LIYRASNLGSGVPDRFSGSGSGTDFTLTISSLQAEDVAVYYCQQINTDPL
TFGQGTKLEIK >hu119VL3
SEQ ID NO: 58
DIVMTQSPDSLAVSLGERATINCRASESVDNSGLSFMHWYQQKPGQPPKL
LLYRASNLGSGIPDRFSGSGSGTDFTLTISSLQAEDVAVYYCQQINTDPL
TFGQGTKLEIK >hu119VL4 (Grafted, IGKV3-11*01)
SEQ ID NO: 59
EIVLTQSPATLSLSPGERATLSCRASESVDNSGLSFMHWYQQKPGQAPRL
LIYRASNLGSGIPARTSGSGSGTDFTLTISSLEPEDFAVYYCQQINTDPL
TFGQGTKLEIK >hu119VL5
SEQ ID NO: 60
EIVLTQSPATLSLSPGERATLSCRASESVDNSGLSFMHWYQQKPGQPPRL
LLYRASNLGSGIPARFSGSGSGTDFTLTISSLEPEDFAVYYCQQINTDPL
TFGQGTKLEIK >hu119VL6
SEQ ID NO: 61
DIVLTQSPATLSLSPGERATLSCRASESVPNSGLSFMHWYQQKPGQPPRL
LLYRASNLGSGIPARTSGSGSGTDFTLTISSLEPEDFAVYYCQQINTDPL
TFGQGTKLEIK >hu119VH1 (Grafted)
SEQ ID NO: 62
EVQLVQSGAEVKKPGSSVKVSCKASGGTFSTYNMHWVRQAPGQGLEWMGA
IYPGNGETSYNQKFKDRVTITADKSTSTAYMELSSLRSEDTAVYYCARED
DYGEGYFDVWGQGTTVTVSS >hu119VH2
SEQ ID NO: 63
EVQLVQSGAEVKKPGSSVKVSCKASGFTFSTYNMHWVRQAPGQGLEWMGA
IYPGNGETSYNQKFKDRVTLTVDKSTSTAYMELSSLRSEDTAVYYCARED
DYGEGYFDVWGQGTTVTVSS >hu119VH3
SEQ ID NO: 64
EVQLVQSGAEVKKPGSSVKVSCKASGFTFSTYNMHWVKHAPGQGLEWIGA
IYPGNGETSYNQKFKDRATLTVDKSTSTAYMELSSLRSEDTAVYYCARED
DYGEGYFDVWGQGTTVTVSS >hu119VH4
SEQ ID NO: 65
EVQLVQSGAEVKKPGSSVKVSCKASGFTFSTYNMHWVKHAPGQGLEWIGA
IYPGNGETSYNQKEKDRATLTVDKSTSTAYMELSSLRSEDTAVYYCARED
DYGEGYFDVWGQGTTVTVSS >hu119VH5
SEQ ID NO: 66
EVQLVQSQAEVKKPGSSVKVSCKASGGTFSTYNMHWVRQAPGQGLEWIGA
IYPGNGETSYNQKFKDRATLTVDKSTSTAYMELSSLRSEDTAVYYCARED
DYGEGYFDVWGQGTTVTVSS >hu119VH6
SEQ ID NO: 67
EAQLVQSGAEVKKPGSSVKVSCKASGFTFSTYNMHWVRQAPGQGLEWIGA
IYPGNGETSYNQKFKDRATLTVDKSTSTAYMELSSLRSEDTAVYYCARED
DYGEGYFDVWGQGTTVTVSS >hu119VH7
SEQ ID NO: 68
EVQLVQSGAEVKKPGSSVKVSCKASGGTFSTYNMHWVRQAPGQGLEWIGA
IYPGNGETSYNQKFKDRATLTVDKSTRTAYMELSSLRSEDTAVYYCARED
DYGEGYFDVWGQGTTVTVSS >hu119VH8
SEQ ID NO: 69
EAQLVQSGAEVKKPGSSVKVSCKASGFTFSTYNMHWVRQAPGQGLEWIGA
IYPGNGETSYNQKFKDRATLTVDKSTRTAYMELSSLRSEDTAVYYCARED
DYGEGYFDVWGQGTTVTVSS Note:
The single underline represents variable regions, and the double underline represents back mutations.

The aforementioned light and heavy chain variable regions were combined with human germline light and heavy chain constant region sequences to form the final complete light and heavy chain sequences, thus obtaining the antibody with full-length sequence. Exemplarily, for the mab119 humanized antibody in the present disclosure, the heavy chain constant region is the IgG1-YTE constant region shown in SEQ ID NO: 133, and the light chain constant region is the kappa chain constant region shown in SEQ ID NO: 134, but they can also be replaced with other constant regions known in the art.

The heavy and light chain variable regions of the mab119 humanized antibody are shown in Table 17.

TABLE 17

| Heavy and light chain variable regions of the mab119 humanized antibody | | |
|---|---|---|
| Antibody | VH (SEQ ID NO) | VL (SEQ ID NO) |
| hu119-01 | 62 | 56 |
| hu119-02 | 63 | 56 |
| hu119-03 | 64 | 56 |
| hu119-04 | 65 | 56 |
| hu119-05 | 62 | 57 |
| hu119-06 | 63 | 57 |
| hu119-07 | 64 | 57 |
| hu119-08 | 65 | 57 |
| hu119-09 | 62 | 58 |
| hu119-10 | 63 | 58 |
| hu119-11 | 64 | 58 |
| hu119-12 | 65 | 58 |
| hu119-13 | 64 | 59 |

TABLE 17-continued

Heavy and light chain variable regions of the mab119 humanized antibody

| Antibody | VH (SEQ ID NO) | VL (SEQ ID NO) |
|---|---|---|
| hu119-14 | 66 | 59 |
| hu119-15 | 67 | 59 |
| hu119-16 | 68 | 59 |
| hu119-17 | 69 | 59 |
| hu119-18 | 64 | 60 |
| hu119-19 | 66 | 60 |
| hu119-20 | 67 | 60 |
| hu119-21 | 68 | 60 |
| hu119-22 | 69 | 60 |
| hu119-23 | 64 | 61 |
| hu119-24 | 66 | 61 |
| hu119-25 | 67 | 61 |
| hu119-26 | 68 | 61 |
| hu119-27 | 69 | 61 |

The binding activity of the humanized antibody to human TSLP was detected by ELISA method, and the results showed that mab119 humanized antibodies can specifically bind to human TSLP.

(2) Mutations of Hu119

It was found by detection that a hot spot was present in the LCDR1 DNS sequence of the mab119 humanized antibody, thus, the corresponding site was mutated to N31S or N31Q. The LCDR1 sequences obtained after mutation are as follows:

TABLE 18

LCDR1 after site mutation of mab119 humanized antibody

| hu119 LCDR1-N31S | RASESVDSSGLSFMH<br>SEQ ID NO: 70 |
|---|---|
| hu119 LCDR1-N31Q | RASESVDQSGLSFMH<br>SEQ ID NO: 71 |

Note:
The positions of mutation sites in Table 19 are numbered according to the natural order.

Exemplarily, the hu119VL2, hu119VL6 mutant sequences obtained after mutation are as follows:

>hu119VL2-N31S
SEQ ID NO: 72
DIVLTQSPDSLAVSLGERATINCRASESVDSSGLSFMHWYQQKPGQPPKL

LIYRASNLGSGVPDRFSGSGSGTDFTLTISSLQAEDVAVYYCQQINTDPL

TFGQGTKLEIK

>hu119VL2-N31Q
SEQ ID NO: 73
DIVLTQSPDSLAVSLGERATINCRASESVDQSGLSFMHWYQQKPGQPPKL

LIYRASNLGSGVPDRFSGSGSGTDFTLTISSLQAEDVAVYYCQQINTDP

LTFGQGTKLEIK

>hu119VL6-N31S
SEQ ID NO: 74
DIVLTQSPATLSLSPGERATLSCRASESVDSSGLSFMHWYQQKPGQPPRL

LYRASNLGSGIPARFSGSGSGTDFTLTISSLEPEDFAVYYCQQINTDPL

TFGQGTKLEIK

>hu119VL6-N31Q
SEQ ID NO: 75
DIVLTQSPATLSLSPGERATLSCRASESVDQSGLSFMHWYQQKPGQPPRL

LYRASNLGSGIPARFSGSGSGTDFTLTISSLEPEDFAVYYCQQINTDPL

TFGQGTKLEIK

Note:
The single underline represents variable regions, and the double underline represents back mutations.

The obtained hu119VL2, hu119VL6 mutants were combined with hu119VH to obtain new humanized hu119 antibodies. Exemplarily, hu119VL2-N31S, hu119VL2-N31Q were respectively combined with hu119VH3 to obtain antibodies hu119-28 and hu119-29; hu119VL3-N31S was combined with hu119VH8 to obtain the antibody hu119-30. Exemplary combinations of variable regions of the mutated antibodies are as follows:

TABLE 19

Combinations of the humanized antibody variable regions after hot spot mutation

| | hu119VH | hu119VL |
|---|---|---|
| hu119-28 | hu119VH3 | hu119VL2-N31S |
| hu119-29 | hu119VH3 | hu119VL2-N31Q |
| hu119-30 | hu119VH8 | hu119VL6-N31S |

The affinity of the antibody obtained after mutation with human TSLP was detected by using ELISA method. The results showed that hu119-28 and hu119-29 antibodies still have relatively high affinity with human TSLP, showing that the N31S and N31Q mutations of LCDR2 will not affect the anti-TSLP antibody activity.

In summary, the CDRs of the mab119 humanized antibody have the sequences shown as follows:

TABLE 20

CDRs of mab119 humanized antibody

| HCDR1 | TYNMH<br>SEQ ID NO: 20 | LCDR1-<br>general<br>formula | RASESVDX$_6$SGLS<br>FMH<br>SEQ ID NO: 76 |
|---|---|---|---|
| HCDR2 | AIYPGNGETSYNQ<br>KFKD<br>SEQ ID NO: 21 | LCDR2 | RASNLGS<br>SEQ ID NO: 24 |
| HCDR3 | EDDYGEGYFDV<br>SEQ ID NO: 22 | LCDR3 | QQINTDPLT<br>SEQ ID NO: 25 |

Wherein, $X_6$ is selected from N, S and Q.

5.3. Humanization of Mab179

(1) Template Selection and Back Mutations for Humanization of Mab179 Murine Antibody For mab179, IGHV1-69*02 and IGHJ6*01 were selected as templates for the VH, and IGKV4-1*01 and IGKJ2*01 or IGKV2-29*02 and IGKJ2*01 were selected as templates for the VL. The CDR regions of the murine antibody were grafted to the selected humanized templates, and the FR regions were subjected to back mutation to obtain light chain and heavy chain variable regions with different sequences.

The humanized variable region sequences and back mutations are as follows:

>hu179VL1 (Graft (IGKV4-1*01))
SEQ ID NO: 77
DIVMTQSPDSLAVSLGERATINCKASQSVSSDVTWYQQKPGQPPKLLIYY

VSNHYTGVPDRFSGSGSGTDFTLTISSLQAEDVAVYYCQQHHRFPLTFGQ

GTKLEIK

>hu179VL5 (Grafted (IGKV2-29*02))
SEQ ID NO: 81
DIVMTQTPLSLSVTPGQPASISCKASQSVSSDVTWYLQKPGQSPQLLIYY

VSNHYTGVPDRFSGSGSGTDFTLKISRVEAEDVGVYYCQQHHRFPLTFGQ

GTKLEIK

>hu179VH1 (Grafted)
SEQ ID NO: 85
EVQLVQSGAEVKKPGSSVKASCKASGGTFSNYLIEWVRQAPGQGLEWMGV

IDPGNGPTNYNENFKGRVTITADKSTSTAYMELSSLRSEDTAVYYCARED

NTGTAFDYWGQGTTVTVSS

TABLE 21

Templates and back mutations for Humanization of mab179

| hu179VL1VL | | hu179VH | |
|---|---|---|---|
| hu179VL1 | Graft (IGKV4-1*01) | hu179VH1 | Graft (IGHV1-69*02) |
| hu179VL2 | Graft (IGKV4-1*01) P43S | hu179VH2 | G27Y, I69L |
| hu179VL3 | Graft (IGKV4-1*01) P43S, L73F | hu179VH3 | G27Y, M48I, V67A, I69L, M80I |
| hu179VL4 | Graft (IGKV4-1*01) D1S, P43S | hu179VH4 | G27Y, R38K, M48I, R66K, V67A, I69L, M80I, S82bR |
| hu179VL5 | Grafted(IGKV2-29*02) | hu179VH5 | G27Y, T28A, M48I, V67A, I69L |
| hu179VL6 | Graft (IGKV2-29*02), D1S | | |
| hu179VL7 | Graft (IGKV2-29*02) D1S, L73F | | |
| hu179VL8 | Graft (IGKV2-29*02) D1S, S67Y | | |

Note:
For example, P43S represents that according to the Kabat numbering system, P at position 43 is mutated back to S. Grafted represents that the murine antibody CDRs are implanted into the human germline FR region sequences.

The variable regions of the mab179 humanized antibody are shown as follows:

>hu179VL1 (Graft (IGKV4-1*01))
SEQ ID NO: 77
DIVMTQSPDSLAVSLGERATINCKASQSVSSDVTWYQQKPGCPPKLLIYY

VSNHYTGVPDRESGSGSGTDFTLTISSLQAEDVAVYYCQQHHREPLTFGQ

GTKLEIK

>hu179VL2
SEQ ID NO: 78
DIVMTQSPDSLAVSLQERATINCKASQSVSSDVTWYQQKPGQSPKLLIYY

VSNHYTGVPDRFSGSGSGTDFILTISSLQAEDVAVYYCQQHHRFPLTFGQ

GTKLEIK

>hu179VL3
SEQ ID NO: 79
DIVMTQSPDSLAVSLGERATINCKASQSVSSDVTWYQQKPGQSPKLLIYY

VSNHYTGVPDRFSGSGSGTDFTETISSLQAEDVAVYYCQQHHRFPLTFGQ

GIKLEIK

>hu179VL4
SEQ ID NO: 80
STVMTQSPDSLAVSLGERATINCKASQSVSSDVTWYQQKPGQSPKLLIYY

VSNHYTGVPDRFSGSGSGTDFTLTISSLQAEDVAVYYCQQHHRFPLTFGQ

GTKLEIK

>hu179VL5 (Grafted (IGKV2-29*02))
SEQ ID NO: 81
DIVMTQTPLSLSVTPGQPASISCKASQSVSSDVTWYLQKPGQSPQLLIYY

VSNHYTGVPDRPSGSGSGTDFTLKISRVEAEDVGVYYCQQHHRFPLTFGQ

GTKLEIK

>hu179VL6
SEQ ID NO: 82
SIVMTQTPLSLSVTPGQPASISCKASQSVSSDVTWYLQKPGQSPQLLIYY

VSNHYTGVPDRFSGSGSGTDFTLKISRVEAEDVGVYYCQQHHRFPLTFGQ

GTKLEIK

>hu179VL7
SEQ ID NO: 83
SIVMTQTPLSLSVTPGQPASISCKASQSVSSDVTWYLQKPGQSPQLLIYY

VSNHYTGVPDRFSGSGSGTDFTFKISRVEAEDVGVYYCQQHHRFPLTFGQ

GTKLEIK

>hu179VL8
SEQ ID NO: 84
SIVMTQTPLSLSVTPGQPASISCKASQSVSSDVTWYLQKPGQSPQLLIYY

VSNHYTGVPDRFSGSGYGTDFTLKISRVEAEDVGVYYCQQHHRFPLTFGQ

GTKLEIK

>hu179VH1 (Grafted)
SEQ ID NO: 85
EVQLVQSGAEVKKPGSSVKVSCKASGGTFSNYLIEWVRQAPGQGLEWMGV

IDPGNGDTNYNENFKGRVTITADKSTSTAYMELSSLRSEDTAVYYCARED

NTGTAFDYWGQGTTVTVSS

>hu179VH2
SEQ ID NO: 86
EVQLVQSGAEVKKPGSSVKVSCKASGYTFSNYLIEWVRQAPGQGLEWMGV

IDPGNGDTNYNENFKGRVTLTADKSTSTAYMELSSLRSEDTAVYYCARED

NTGTAFDYWGQGTTVTVSS

>hu179VH3
SEQ ID NO: 87
EVQLVQSGAEVKKPGSSVKVSCKASGYTFSNYLIEWVRQAPGQGLEWIGV

IDPGNGDTNYNENFKGRATLTADKSTSTAYIELSSLRSEDTAVYYCARED

NTGTAFDYWGQGTTVTVSS

>hu179VH4
SEQ ID NO: 88
EVQLVQSGABVKKPGSSVKVSCKASGYTFSNYLIEWVKQAPGQGLEWIGV

IDPGNGDTNYNENFKGKATLTADKSTSTAYIELSRLRSEDTAVYYCARED

NTGTAFDYWGQGTTVTVSS

>hu179VH5
SEQ ID NO: 89
EVQLVQSGAEVKKPGSSVKVSCKASG<u>YAFS</u><u>NYLIE</u>WVRQAPGQGLEW<u>IGV</u>
<u>IDPGNGDTNYNENFKGR</u><u>ATL</u>TADKSTSTAYMELSSLRSEDTAVYYCAR<u>ED</u>
<u>NTGTAFDY</u>WGQGTTVTVSS
Note:
The single underlined part represents CDRs, and the double underlined represents back mutation sites.

The aforementioned light and heavy chain variable regions were combined with human germline light and heavy chain constant region sequences to form the final complete light and heavy chain sequences, thus obtaining the antibody with full-length sequence. Exemplarily, for the mab199 humanized antibody in the present disclosure, the heavy chain constant region is the IgG1-YTE constant region shown in SEQ ID NO: 133, and the light chain constant region is the kappa chain constant region shown in SEQ ID NO: 134, but they can also be replaced with other constant regions known in the art.

TABLE 22

Combinations of heavy and light chain variable regions of the mab 179 humanized antibody

| Antibody | VH (SEQ ID NO) | VL (SEQ ID NO) |
|---|---|---|
| hu179-01 | 85 | 77 |
| hu179-02 | 85 | 78 |
| hu179-03 | 86 | 77 |
| hu179-04 | 86 | 78 |
| hu179-05 | 87 | 77 |
| hu179-06 | 87 | 78 |
| hu179-07 | 87 | 79 |
| hu179-08 | 87 | 81 |
| hu179-09 | 87 | 82 |
| hu179-10 | 87 | 83 |
| hu179-11 | 87 | 84 |
| hu179-12 | 88 | 77 |
| hu179-13 | 88 | 78 |
| hu179-14 | 89 | 79 |
| hu179-15 | 89 | 80 |
| hu179-16 | 89 | 81 |
| hu179-17 | 89 | 82 |
| hu179-18 | 89 | 83 |
| hu179-19 | 89 | 84 |

The affinity of mab179 humanized antibody with human TSLP was detected by using ELISA method, and the results showed that mab179 humanized antibodies have very good affinity with human TSLP.

(2) Mutations of Hu179 Antibody

It was found by detection that there were hot spots on the HCDR2 and LCDR2 sequences of the mab179 humanized antibody. Therefore, the corresponding hot spots were mutated to eliminate the risk of molecule modification.

In one of the embodiments, GNG of HCDR2 of hu179VH1 was subjected to amino acid mutation, and the sequences of hu179VH1 after mutation are:

hu179VH1-N55Q
SEQ ID NO: 90
EVQLVQSGAEVKKPGSSVKVSCKASGGTFS<u>NYLIE</u>WVRQAPGQGLEWMGV
<u>IDPGQGDTNYNENFKGR</u>VTTTADKSTSTAYMELSSLRSEDTAVYYCAR<u>ED</u>
<u>NTCAFDY</u>WGQGTTVTVSS hu179VH1-N55V
SEQ ID NO: 91
EVQLVQSGAEVKKPGSSVKVSCKASGGTFS<u>NYLIE</u>WVRQAPGQGLEWMGV
<u>IDPGVGDTNYNENFKGR</u>VTTTADKSTSTAYMELSSLRSEDTAVYYCAR<u>ED</u>
<u>NTGTAFDY</u>WGQGTTVTVSS hu179VH1-G56V
SEQ ID NO: 92
EVQLVQSGAEVKKPGSSVKVSCKASGGTFS<u>NYLIE</u>WVRQAPGQGLEWMGV
<u>IDPGNVDTNYNENFKGR</u>VTTTADKSTSTAYMELSSLRSEDTAVYYCAR<u>ED</u>
<u>NTGTAFDY</u>WGQGTTVTVSS
Note:
The single underlined part represents CDRs, and the double underlined represents back mutation sites.

The sequences of HCDR2 regions of the mab179 humanized antibody obtained after mutation are as follows:

TABLE 23

HCDR2 mutants of the mab179 humanized antibody

| hu179 HCDR2-N55Q | VIDPGQGDTNYNENFKG<br>SEQ ID NO: 93 |
|---|---|
| hu179 HCDR2-N55V | VIDPGVGDTNYNENFKG<br>SEQ ID NO: 94 |
| hu179 HCDR2-G56V | VIDPGNVDTNYNENFKG<br>SEQ ID NO: 95 |

Note:
The positions of mutation sites in Table 24 are numbered according to the natural order.

The CDR regions of the mab179 humanized antibody can be obtained from above, and are shown as follows:

TABLE 24

CDRs of mab179 humanized antibody after mutation

| HCDR1 | NYLIE<br>SEQ ID NO: 26 | LCDR1 | KASQSVSSDVT<br>SEQ ID NO: 29 |
|---|---|---|---|
| HCDR2 (general formula) | VIDPGX$_7$X$_8$DTNYN<br>ENFKG<br>SEQ ID NO: 96 | LCDR2 | YVSNHYT<br>SEQ ID NO: 30 |
| HCDR3 | EDNTGTAFDY<br>SEQ ID NO: 28 | LCDR3 | QQHHRFPLT<br>SEQ ID NO: 31 |

Wherein, $X_7$ is selected from N, Q or V, $X_8$ is selected from G or V.

The hu179VH1 mutants obtained after mutation were combined with the humanized hu179VL to obtain new mab179 humanized antibodies. Exemplary antibodies of combination of hu179VH1 mutant and hu179VL2 are as follows:

TABLE 25

Combinations of the antibody variable regions after mutation

| Variable region | hu179VH1-N55Q | hu179VH1-N55V | hu179VH1-G56V |
|---|---|---|---|
| hu179VL2 | hu179-20 | hu179-21 | hu179-22 |

The affinity of the antibody obtained after mutation with human TSLP was detected by using ELISA method. The results showed that antibodies after HCDR2 mutation still maintain relatively high affinity with human TSLP. This showed that the N55Q, N55V and G56V point mutations of HCDR2 of the mab179 humanized antibody will basically not affect the affinity activity of the antibody with TSLP.

According to the same method, N55Q, N55V and G56V point mutations (numbered by the natural order) were made on hu179VH2, hu179VH3, hu179VH4 and hu179VH5 respectively, and the heavy and light chain variable regions obtained by mutation were recombined to obtain new mab179 humanized antibodies. Exemplarily, the mutated sequence of hu179VH3 is shown as follows:

```
>hu179VH3-N55V
                                      SEQ ID NO: 97
EVQLVQSGAEVKKPGSSVKVSCKASGYTFSNYLIEWVRQAPGQGLEWIG

VIDPGVGDTNYNENFKGRATLTADKSTSTAYIELSSLRSEDTAVYYCAR

EDNTGTAFDYWGQGTTVTVSS
```

Note:
The single underlined part represents CDRs, and the double underlined represents back mutation sites.

In some other examples, LCDR2 of mab179 humanized antibody was subjected to amino acid mutation. Exemplarily, the sequences of hu179VL2 after mutation are as follows:

```
>hu179VL2-Y50E
                                      SEQ ID NO: 98
DIVMTQSPDSLAVSLGERATINCKASQSVSSDVTWYQQKPGQSPKLLIY

EVSNHYTGVPDRFSGSGSGTDFTLTISSLQAEDVAVYYCQQHHRFPLTF

GQGTKLEIK

>hu179VL2-S52D
                                      SEQ ID NO: 99
DIVMTQSPDSLAVSLGERATINCKASQSVSSDVTWYQQKPGQSPKLLIY

YVDNHYTGVPDRFSGSGSGTDFTLTISSLQAEDVAVYYCQQHHRFPLTF

GQGTKLEIK

>hu179VL2-S52E
                                     SEQ ID NO: 100
DIVMTQSPDSLAVSLGERATINCKASQSVSSDVTWYQQKPGQSPKLLIY

YVENHYTGVPDRFSGSGSGTDFTLTISSLQAEDVAVYYCQQHHRFPLTF

GQGTKLEIK

>hu179VL2-N53Q
                                     SEQ ID NO: 101
DIVMTQSPDSLAVSLGERATINCKASQSVSSDVTWYQQKPGQSPKLLIY

YVSQHYTGVPDRFSGSGSGTDFTLTISSLQAEDVAVYYCQQHHRFPLTF

GQGTKLEIK

>hu179VL2-N53D
                                     SEQ ID NO: 102
DIVMTQSPDSLAVSLGERATINCKASQSVSSDVTWYQQKPGQSPKLLIY

YVSDHYTGVPDRFSGSGSGTDFTLTISSLQAEDVAVYYCQQHHRFPLTF

GQGTKLEIK

>hu179VL2-N53E
                                     SEQ ID NO: 103
DIVMTQSPDSLAVSLGERATINCKASQSVSSDVTWYQQKPGQSPKLLIY

YVSEHYTGVPDRFSGSGSGTDFTLTISSLQAEDVAVYYCQQHHREPLTF

GQGTKLEIK
```

-continued

```
>hu179VL2-H54Y
                                     SEO ID NO: 104
DIVMTQSPDSLAVSLGERATINCKASQSVSSDVTWYQQKPGQSPKLLIY

YVSNYYTGVPDRFSGSGSGTDFTLTISSLQAEDVAVYYCQQHHRFPLTF

GQGTKLEIK

>hu179VL2-H54D
                                     SEQ ID NO: 105
DIVMTQSPDSLAVSLGERATINCKASQSVSSDYTWYQQKPGQSPKLLIY

YVSNDYTGVPDRFSGSGSGTDFTLTISSLQAEDVAVYYCQQHHRFPLTF

GQGTKLEIK

>hu179VL2-H54E
                                     SEQ ID NO: 106
DIVMTQSPDSLAVSLGERATINCKASQSYSSDYIWYQQKPGQSPKLLIY

YVSNEYTGVPDRFSGSGSGTDFTLTISSLQAEDYAYYYCQQHHRFPLTF

GQGTKLEIK

>hu179VL2-Y55E
                                     SEQ ID NO: 107
DIVMTQSPDSLAVSLGERATINCKASQSVSSDVTWYQQKPGQSPKLLIY

YVSNHETGVPDRFSGSGSCTDFTLTISSLQAEDVAVYYCQQHHREPLTF

GQGTKLEIK
```

Note:
The single underlined part represents CDRs, and the double underlined represents back mutation sites.

The sequences of the mab179 humanized antibody LCDR2 obtained after mutation are as follows:

TABLE 26

LCDR2 mutants of the mab179 humanized antibody

| Mutant | Sequence |
|---|---|
| hu179 LCDR2-Y50E | EVSNHYT<br>SEQ ID NO: 108 |
| hu179 LCDR2-S52D | YVDNHYT<br>SEQ ID NO: 109 |
| hu179 LCDR2-S52E | YVENHYT<br>SEQ ID NO: 110 |
| hu179 LCDR2-N53Q | YVSQHYT<br>SEQ ID NO: 111 |
| hu179 LCDR2-N53D | YVSDHYT<br>SEQ ID NO: 112 |
| hu179 LCDR2-N53E | YVSEHYT<br>SEQ ID NO: 113 |
| hu179 LCDR2-H54Y | YVSNYYT<br>SEQ ID NO: 114 |
| hu179 LCDR2-H54D | YVSNDYT<br>SEQ ID NO: 115 |
| hu179 LCDR2-H54E | YVSNEYT<br>SEQ ID NO: 116 |
| hu179 LCDR2-Y55E | YVSNHET<br>SEQ ID NO: 117 |

It can be seen from the above that the general formula of LCDR2 of mab179 humanized antibody is: $X_9VX_{10}X_{11}X_{12}X_{13}T$ (SEQ ID NO: 118), wherein $X_9$ is selected from Y or E, $X_{10}$ is selected from S, D or E, $X_{11}$ is selected from N, Q, D or E; $X_{12}$ is selected from H, Y, D or E; $X_{13}$ is selected from E or Y. The CDR regions of the mab179 humanized antibody are as shown in the following table:

TABLE 27

CDRs of mab179 humanized antibody

| HCDR1 | NYLIE<br>SEQ ID NO: 26 | LCDR1 | KASQSVSSDVT<br>SEQ ID NO: 29 |
|---|---|---|---|
| HCDR2 | VIDPGX$_7$X$_8$DTNYNENFKG<br>SEQ ID NO: 96 | LCDR2 | X$_9$VX$_{10}$X$_{11}$X$_{12}$X$_{13}$T<br>SEQ ID NO: 118 |
| HCDR3 | EDNTGTAFDY<br>SEQ ID NO: 28 | LCDR3 | QQHHRFPLT<br>SEQ ID NO: 31 |

Wherein, $X_7$ is selected from N, Q or V, $X_8$ is selected from G or V; $X_9$ is selected from Y or E; $X_{10}$ is selected from S, D or E; $X_{11}$ is selected from N, Q, D or E; $X_{12}$ is selected from H, Y, D or E; $X_{13}$ is selected from E or Y.

The hu179VL2 mutants obtained after mutation were combined with the humanized hu179 heavy chain variable regions to obtain new mab179 humanized antibodies. As an example, hu179VL2 mutants were combined with hu179VH1, hu179VH3, and the CDRs and the combinations of the heavy and light chain variable regions of the obtained mab179 humanized antibodies are shown as follows:

TABLE 28

The sequences of CDR regions of the mab179 humanized antibody after LCDR2 mutation

| HCDR1 | NYLIE<br>SEQ ID NO: 26 | LCDR1 | KASQSVSSDVT<br>SEQ ID NO: 29 |
|---|---|---|---|
| HCDR2 | VIDPGNGDTNYNENFKG<br>SEQ ID NO: 27 | LCDR2 | X$_5$VX$_6$X$_7$X$_8$X$_9$T<br>SEQ ID NO: 118 |
| HCDR3 | EDNTGTAFDY<br>SEQ ID NO: 28 | LCDR3 | QQHHRFPLT<br>SEQ ID NO: 31 |

Wherein, $X_5$ is selected from Y or E; $X_6$ is selected from S, D or E; $X_7$ is selected from N, Q, D or E; $X_8$ is selected from H, Y, D or E; $X_9$ is selected from E or Y.

TABLE 29

Combinations of heavy and light chain variable regions of mab179 humanized antibody after LCDR2 mutation

| Antibody | VH (SEQ ID NO) | VL (SEQ ID NO) |
|---|---|---|
| hu179-23 | 85 | 102 |
| hu179-24 | 85 | 104 |
| hu179-25 | 87 | 98 |
| hu179-26 | 87 | 99 |
| hu179-27 | 87 | 100 |
| hu179-28 | 87 | 101 |
| hu179-29 | 87 | 103 |
| hu179-30 | 87 | 105 |
| hu179-31 | 87 | 106 |
| hu179-32 | 87 | 107 |

The affinity of the mab179 humanized antibodies obtained after LCDR2 mutation with human TSLP was detected by using ELISA method. The results showed that antibodies obtained after hot spot site mutation to LCDR2 still have relatively good affinity with human TSLP. This showed that hot spot site mutation to LCDR2 will not affect the binding activity of the mab179 humanized antibodies.

According to the same method, N53Q, N53D, N53S, H54Y, Y50E, S52D, S52E, N53E, H54D, H54E, Y55E mutations were made on LCDR2 of hu179VL3, hu179VL4, hu179VL5, hu179VL6, hu179VL7 and hu179VL8. The light chain variable regions and the heavy chain variable regions after mutation were combined to form new mab humanized antibodies. In one embodiment, the sequence of hu179VL8 after mutation is shown as follows:

hu179L8-N53E:
SEQ ID NO: 1
SIVMTQPLSLSVTPGQPASISC<u>KASQSVSSDVT</u>WYLQKPGQSPQLLIYY<u>V</u>
<u>SEHYT</u>GVPDRFSGSG<u>Y</u>GTDFTLKISRVEAEDVGVYYC<u>QQHHRFPLT</u>FGQG
TKLEIK hu179VL8-N53E and hu179VH3-N55V obtained by mutation were combined to obtain a new antibody molecule hu179-33, the CDR sequences of which are shown as follows:

TABLE 30

CDR regions of hu179-33 antibody

| HCDR1 | NYLIE<br>SEQ ID NO: 26 | LCDR1 | KASQSVSSDVT<br>SEQ ID NO: 29 |
|---|---|---|---|
| HCDR2-<br>N55V | VIDPGVGDTNYNENFK<br>G<br>SEQ ID NO: 94 | LCDR2-<br>N53E | YVSEHYT<br>SEQ ID NO: 113 |
| HCDR3 | EDNTGTAFDY<br>SEQ ID NO: 28 | LCDR3 | QQHHRFPLT<br>SEQ ID NO: 31 |

The binding activity of antibodies obtained after mutation to human TSLP was detected by Biacore. Exemplary binding activity of antibodies is shown as follows:

TABLE 31

Affinity of hu179-33 with human TSLP

| Antibody | Affinity to huTSLP KD (M) |
|---|---|
| AMG157 | 8.12E−12 |
| hu179-33 | 9.03E−13 |

The results showed that antibody hu179-33 has relatively high specific binding activity to human TSLP. This indicated that point mutations of hot spots on both HCDR2 and LCDR2 will not affect the affinity of the mab179 humanized antibody to human TSLP. It can be seen that in the mab179 humanized antibody molecule, mutations of N55Q, N55V, G56V made on HCDR2, and mutations of N53Q, N53D, N53S, H54Y, Y50E, S52D, S52E, N53E, H54D, H54E, Y55E made on LCDR2 will not affect the binding of the antibody to human TSLP, i.e., will not affect the activity of anti-TSLP antibodies.

5.4 Selection and Back Mutations of the Human FR Regions for Mab199 Antibody

For mab199, IGHV1-46*01 and HJ6*01 were selected as templates for the VH, and IGKV1-39*01 and IGKJ4*01 were selected as templates for the VL. The CDR regions of the murine antibody were grafted to the selected humanized templates, and the FR region was subjected to back mutation to obtain light chain and heavy chain variable regions with different sequences. The back mutations are as shown in Table 32.

TABLE 32

Design of back mutations for mab199

| hu199VL | | hu199VH | |
|---|---|---|---|
| hu199VL1 | Grafted | hu199VH1 | Grafted |
| hu199VL2 | I48V | hu199VH2 | R71V, T73K, V78A |
| hu199VL3 | A43S, K45Q, I48V, D70Q | hu199VH3 | M69L, R71V, T73K, V78A |
| hu199VL4 | G66V | hu199VH4 | M48I, V67A, M69L, R71V, T73K, V78A |
| hu199VL5 | I48V, G66V | hu199VH5 | R38K, M48I, R66K, V67A, M69L, R71V, T73K, V78A |
| hu199VL6 | A43S, K45Q, I48V, G66V, D70Q | hu199VH6 | R38K, R66K, R71V, T73K, V78A |
| | | hu199VH7 | R38K, R67K, M69L, R71V, T73K, V78A |

Note:
For example, I48V represents that according to the Kabat numbering system, I at position 48 is mutated back to V. Grafted represents that the murine antibody CDRs are implanted into the human germline FR region sequences.

The variable regions of the mab199 humanized antibody are shown as follows:

>hu199VL1 (Grafted)
SEQ ID NO: 120
DIQMTQSPSSLSASVGDRVTITCRASENIYSYLAWYQQKPGKAPKLLIYFAKTLAEGVPSRFSGSGSGTDFTLTISSLQPEDFATYYCQHHYGTPWTFGGGTKVEIK >hu199VL2
SEQ ID NO: 121
DIQMTQSPSSLSASVGDRVTTTCRASENIYSYLAWYQQKPGKAPKLLVYFAKTLAEGVPSRFSGSGSGTDFTLTISSLQPEDFATTYCQHHYGTPWTFGGGTKVEIK >hu199VL3
SEQ ID NO: 122
DIQMTQSPSSLSASVGDRVTITCRASENIYSLAWYQQKPGKSPQLLVYFAKTLAEGVPSRFSGSGSGTQFTLTISSLQPEDFATYYCQHHYGTPWTFGGTKVEIK >hu199VL4
SEQ ID NO: 123
DIQMTQSPSSLSASVCDRVTITCRASENIYSYLAWYQQKPGKAPKLLIYFAKTLAEGVPSRFSGSVSGTDFTLTISSSLQPEDFATYYCQHHYGTPWTFGGGTKVEIK >hu199VL5
SEQ ID NO: 124
DIQMTQSPSSLSASVGDRVTITCRASENIYSYLAWYQQKPGKAPKLLVYFAKTLAEGVPSRFSGSVSGTDFTLISSLQPEDFATYYCQHHYGTPWTFGGTKVEIK >hu199VL6
SEQ ID NO: 125
DIQMTQSPSSLSASVGDRVTITCRASENIYSYLAWYQQKPGKSPQLLVYFAKTLAEGVPSRFSGSVSGTQFTLTSSLQPEDFATYYCQHHYCPWTFGGTKVEIK >hu199VH1 (Grafted)
SEQ ID NO: 126
EVQLVQSGAEVKKPGASVKVSCKASGYTFTTYWMHWVRQAPGQGLEWMGMIDPSDSETTLIQKFKDRVTMTRDTSTSTVYMELSSLRSEDTAVYYCARTLDGYYDYWGQGTTVTVSS >hu199VH2
SEQ ID NO: 127
EVQLVQSGAEVKKPGASVKVSCKASGYTFTTYWMHWVRQAPGQGLEWMGMIDPSDSETTLIQKFKDRVTMTVDKSTSTAYMELSSLRSEDTAVYYCARTLDGYYDYWGQGTTVTVSS >hu199VH3
SEQ ID NO: 128
EVQLVQSGAEVKKPGASVKVSCKASGYTFTTYWMHWVRQAPGQGLEWMGMIDPSDSETTLIQKFKDRVTLTVDKSTSTAYMELSSLRSEDTAVYYCARTLDGYYDYWQQGTTVTVSS >hu199VH4
SEQ ID NO: 129
EVQLVQSGAEVKKPGASVKVSCKASGYTFTTYWMHWVRQAPGQGLEWIGMIDPSDSETTLIQKFKDRATLTVDKSTSTAYMELSSLRSEDTAVYYCARTLDGYYDYWGQGTTVTVSS hu199VH5
SEQ ID NO: 130
EVQLVQSGAEVKKPGASVKVSCKASGYTFTTYWMHWVKQAPGQGLEWIGMIDPSDSETTLIQKFKDKATLTVDKSTSTAYMELSSLRSEDTAVYYCARTLDGYYDYWGQGTTVTVSS >hu199VH6
SEQ ID NO: 131
EVQLVQSGAEVKKPGASVKVSCKASGYTFTTYWMHWVKQAPGQGLEWMGMIDPSDSETTLIQKFKDKVTMTVDKSTSTAYMELSSLRSEDTAVYYCARTLDGYYDYWGQGTTVTVSS >hu199VH7
SEQ ID NO: 132
EVQLVQSGAEVKKPGASVKVSCKASGYTFTTYWMHWVKQAPGQGLEWMGMIDPSDSETTLIQKFKDKVTLTVDKSTSTAYMELSSLRSEDTAVYYCARTLDGYYDYWGQGTTVTVSS Note:
The single underlined part represents CDRs, and the double underlined represents back mutation sites.

The aforementioned light and heavy chain variable regions were combined with human germline light and heavy chain constant region sequences to form the final complete light and heavy chain sequences, thus obtaining the antibody with full-length sequence. For the mab199 humanized antibodies, if there is no clear description in the present disclosure, the light chain constant region is the constant region shown in SEQ ID NO: 134, and the heavy chain constant region is the constant region shown in SEQ ID NO: 133.

The obtained mab199 humanized antibodies are shown as follows:

TABLE 33

Sequences of heavy and light chain variable regions of the mab199 humanized antibodies

| Antibody | VH (SEQ ID NO) | VL (SEQ ID NO) |
|---|---|---|
| hu199-01 | 127 | 120 |
| hu199-02 | 127 | 121 |
| hu199-03 | 127 | 122 |
| hu199-04 | 127 | 123 |
| hu199-05 | 127 | 124 |
| hu199-06 | 127 | 125 |
| hu199-07 | 128 | 120 |
| hu199-08 | 128 | 121 |
| hu199-09 | 128 | 122 |
| hu199-10 | 128 | 123 |
| hu199-11 | 128 | 124 |
| hu199-12 | 128 | 125 |
| hu199-13 | 129 | 120 |
| hu199-14 | 129 | 121 |
| hu199-15 | 129 | 122 |
| hu199-16 | 129 | 123 |
| hu199-17 | 129 | 124 |
| hu199-18 | 129 | 125 |
| hu199-19 | 130 | 120 |
| hu199-20 | 130 | 121 |
| hu199-21 | 130 | 122 |
| hu199-22 | 130 | 123 |
| hu199-23 | 130 | 124 |
| hu199-24 | 130 | 125 |
| hu199-25 | 131 | 120 |
| hu199-26 | 131 | 121 |
| hu199-27 | 131 | 122 |
| hu199-28 | 131 | 123 |
| hu199-29 | 131 | 124 |
| hu199-30 | 131 | 125 |
| hu199-31 | 132 | 120 |
| hu199-32 | 132 | 121 |
| hu199-33 | 132 | 122 |
| hu199-34 | 132 | 123 |
| hu199-35 | 132 | 124 |
| hu199-36 | 132 | 125 |

The activity of the mab199 humanized antibodies blocking the binding of TSLP to TSLP receptor was detected by using ELSA method, and the detection results are as follows:

The results showed that the mab199 humanized antibodies still have relatively high activity of blocking the binding of TSLP to TSLP receptor.

5.5 Antibody Constant Regions

The heavy chain constant region of humanized antibody and chimera antibody can be selected from the group consisting of the constant regions of IgG1, IgG2, IgG4 and variants thereof. Exemplarily, IgG1-YTE constant region was used in the present disclosure, and its sequence is as shown in SEQ ID NO: 133. The light chain constant region can be selected from the light chain constant regions of human κ, λ chain or variants thereof. Exemplarily, human κ chain constant region was used in the present disclosure, and its sequence is as shown in SEQ ID NO: 134.

>IgG1-YTE heavy chain constant region:
SEQ ID NO: 133
ASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDK

KVEPKSCDKTHTCPPCPAPELLGGPSVFLFPPKPKDTL<u>Y</u>I<u>T</u>R<u>E</u>PEVTC

VVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFF

LYSKLTVDKSRWQQGNVFSCSVMHEALHNHYTQKSLSLSPGK
Note:
Underlined refers to the designed M252Y, S254T, T256E mutations > κ light chain constant region:
SEQ ID NO: 134
RTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSS

PVTKSFNRGEC

The humanized heavy and light chain variable regions in the present disclosure were recombined with the above constant regions to obtain the full-length sequences of the heavy and light chains. Exemplarily, the antibody sequences are as follows:

TABLE 34

Activity of mab199 humanized antibody blocking the binding of TSLP to TSLP receptor

| Antibody | IC50 (nM) | Antibody | IC50 (nM) | Antibody | IC50 (nM) | Antibody | IC50 (nM) |
|---|---|---|---|---|---|---|---|
| hu199-01 | 0.1912 | hu199-10 | 0.3910 | hu199-191 | 0.6584 | hu199-28 | 0.4619 |
| hu199-02 | 0.2193 | hu199-11 | 0.3648 | hu199-20 | 0.4001 | hu199-29 | 0.5543 |
| hu199-03 | 0.2077 | hu199-12 | 0.3700 | hu199-21 | 0.5353 | hu199-30 | 0.3493 |
| hu199-04 | 0.4242 | hu199-13 | 0.2395 | hu199-22 | 0.3449 | hu199-31 | 0.3044 |
| hu199-05 | 0.4726 | hu199-14 | 0.3112 | hu199-23 | 0.3370 | hu199-32 | 0.2870 |
| hu199-06 | 0.3806 | hu199-15 | 0.2866 | hu199-24 | 0.4960 | hu199-33 | 0.2055 |
| hu199-07 | 0.2834 | hu199-16 | 0.7367 | hu199-25 | 0.2460 | hu199-34 | 0.7107 |
| hu199-08 | 0.2828 | hu199-17 | 0.6111 | hu199-26 | 0.3651 | hu199-35 | 0.4849 |
| hu199-09 | 0.2732 | hu199-18 | 0.4806 | hu199-27 | 0.3544 | hu199-36 | 0.7273 |
| Ch199 | 0.4266 | | | | | | | hu3-13 antibody heavy chain:
SEQ ID NO: 135

EVQLVQSGAEVKKPGASVKVSCKASGYTFDDYMNWVRQAPGQRLEWMGIISPYNGGTSYNQKFKGRVTLTVDKSASTAYMELSSLRSEDTAVYYCAREDYDYDGYAMDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLYITREPEVTCVVVDYSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK hu3-13 antibody light chain:
SEQ ID NO: 136

EIVLTQSPATLSLSPGERATLSCRASSSVSYMHWYQQKPGQAPRPWIYATSNLASGVPARFSGSGSGTSYTLTISRLEPEDFAVYYCQQSDSGREFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC hu119-30 antibody heavy chain
SEQ ID NO: 137

EAQLVQSGAEVKKPGSSVKVSCKASGFTFSTYNMHWVRQAPGQGLEWIGAIYPGNGETSYNQKFKDRATLTVDKSTRTAYMELSSLRSEDTAVYYCAREDDYGEGYFDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK hu119-30 antibody light chain
SEQ ID NO: 138

DIVLTQSPATLSLSPGERATLSCRASESVDSSGLSFMHWYQQKPGQPPRLLLYRASNLGSGIPARFSGSGSGTDFTLTISSLEPEDFAVYYCQQINTDPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC hu179-33 antibody heavy chain
SEQ ID NO: 139

EVQLVQSGAEVKKPGSSVKVSCKASGYTFSNYLIEWVRQAPGQGLEWIGVIDPGYGDTNYNENFKGRATLTADKSTSTAYIELSSLRSEDTAVYYCAREDNTGTAFDYWGQGTTVTVSSASTKGPSVFPLAPSSKSTSGGTAALGCLVKDYFPEPVTVSWNSGALTSGVMTFPAVLQSSGLYSLSSVVTVPSSSLGTQTYICNVNHKPSNTKVDKKVEPKSCDKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK hu179-33 antibody light chain
SEQ ID NO: 140
SIVMTQTPLSLSVTPGQPASISCKASQSVSSDVTWYLQKPGQSPQLLIYYVSEH

YTGVPDRFSGSGYGTDFTLKISRVEAEDVGVYYCQQHHRFPLTFGQGTKLEIK

RTVAAPSVFIFPPSDEQLKSGTASVVCLLNNFYPREAKVQWKVDNALQSGNSQESV

TEQDSKDSTYSLSSTLTLSKADYEKHKVYACEVTHQGLSSPVTKSFNRGEC hu199-36 antibody heavy chain
SEQ ID NO: 141
EVQLVQSGAEVKKPGASVKVSCKASGYTFTTYWMHWVKQAPGQGLEWMG

MIDPSDSETTLIQKFKDKVTLTVDKSTSTAYMELSSLRSEDTAVYYCARTLDG

YYDYWGQGTTVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLYITREPEVTCVVVDVSHED

PEVKFNWYVDGVEVHNAKTKPREEQYNSTYRVYSVLTVLHQDWLNGKEYKCKVS

NKALPAPIEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHEALHNHY

TQKSLSLSPGK hu199-36 antibody light chain:
SEQ ID NO: 142
DIQMTQSPSSLSASVGDRVTITCRASENIYSYLAWYQQKPGKSPQLLVYFAKT

LAEGVPSRFSGSVSGTQFTLTISSLQPEDFATYYCQHHYGTPWTFGGGTKVEIK

RTVAAPSVFIFPPSDEQLKSGTASVVCLLNNFYPREAKVQWKVDNALQSGNSQESV

TEQDSKDSTYSLSSTLTLSKADYEKHKVYACEVTHQGLSSPVTKSFNRGEC
Note:
The underlined part represents CDR, and the italicized part represents constant region.

AMG157 was used as a positive control for the present disclosure, and its sequence is as shown in SEQ ID NO: 143 and SEQ ID NO: 144.

Heavy chain sequence of AMG157
SEQ ID NO: 143
QMQLVESGGGVVQPGRSLRLSCAASGFTFRTYGMHWVRQAPGKGLEWVAV

IWYDGSNKHYADSVKGRFTITRDNSKNTLNLQMNSLRAEDTAVYYCARAP

QWELYHEAEDIWGQGTMVTVSSASTKGPSVFPLAPCSRSTSESTAALGCL

VKDYFPEPVTVSWNSGALTSGVHTFPAVLQSSGLYSLSSVVTVPSSNFGT

QTYTCNVDHKPSNTKVDKTVERKCCVECPPCPAPPVAGPSVFLFPPKPKD

TLMISRTPEVTCVVVDVSHEDPEVQFNWYVDGVEVHNAKTKPREEQFNST

FRVVSVLTVVHQDWLNGKEYKCKVSNKGLPAPIEKTISKTKGQPREPQVY

TLPPSREEMTKNQVSLTCLVKGFYPSDIAVEWESNGQPENNYKTTPPMLD

SDGSFFLYSKLTVDKSRWQQGNVFSCSVMHEALHNHYTQKSLSLSPGK

Light chain sequence of AMG157
SEQ ID NO: 144
SYVLTQPPSVSVAPGQTARITCGGNNLGSKSVHWYQQKPGQAPVLYYYDD

SDRPSWIPERESGSNSGNTATLTISRGEACDEADYYCQYWDSSSDHYYFG

GGTKLTVLGQPKAAPSVTLFPPSSEELQANKATLVCLISDFYPGAVTVAW

KADSSPVKAGVETTTPSKQSNNKYAASSYLSLTPEQWKSHRSTSCQVTHE

GSTVEKTVAPTECS

In addition, when testing the antibody activity, the present disclosure also used human TSLP receptor and human IL7Rα to construct cell lines, and their sequences are as follows:

Full-length amino acid sequence of human TSLP receptor:
SEQ ID NO: 145
MGRLVLLWGAAVFLLGGWMALGQGGAAEGVQIQIIYFNLETVQVTWNAS

KYSRTNLTFHYRFHGDEAYDQCTNYLLQEGHTSGCLLQAEQRDDILYFS

IRHGTHPVFTASRWMVYYLKPSSPKHVRFSWHQDAVTVTCSDLSYGDLL

YEVQYRSPFDTEWQSKQENTCNVTIEGLDAEKCYSFWVRVKAMEDVYGP

DTYPSDWSEVTCWQRGEIRDACAETPTPPKPKLSKFILISSLAILLMVS

LLLLSLWKLWRVKKFLIPSVPDPKSIFPGLFEIHQGNFQEWITDTQNVA

HLHKMAGAEQESGPEEPLVVQLAKTEAESPRMLDPQTEEKEASGGSLQL

PHQPLQGGDVVTIGGFTFVMNDRQLAKTEAESPRMLDPQTEEKEASGGS

LQLPHQPLQGGDVVTIGGFTFVMNLSYVAL
Note:
The underlined part refers to the signal
peptide Full-length amino acid sequence of human IL7Rα
(Uniprot ID: P16871)
SEQ ID NO: 146
MTILGTTFGMVFSLLQVVSGESGYAQNGDLEDAELDDYSFSCYSQLEVN

GSQHSLTCAFEDPDVNTTNLEFEICGALVEVKCLNFRKLQEIYFIETKK

FLLIGKSNICKVGEKSLTCKKIDLTTIVKPEAPFDLSVIYREGANDFVV

TFNTSHLQKKYVKVLMHDVAYRQEKDENKWTHVNLSSTKLTLLQRKLQP

AAMYEIKVRSIPDHYFKGFWSEWSPSYYFRTPEINNSSGEMDPILLTIS

ILSFFSVALLVILACVLWKKRIKPIVWPSLPDHKKTLEHLCKKPRKNLN

VSFNPESFLDCQIHRVDDIQARDEVEGFLQDTFPQQLEESEKQRLGGDV

QSPNCPSEDVVITPESFGRDSSLTCLAGNVSACDAPILSSSRSLDCRES

GKNGPHVYQDLLLSLGTTNSTLPPPFSLQSGILTLNPVAQGQPILTSLG

SNQEEAYVTMSSPYQNQ
Note:
The underlined part refers to the signal
peptide

The antibodies of the present disclosure can be cloned, expressed and purified using conventional gene cloning and recombinant expression methods.

TEST EXAMPLES

Biological Evaluation of In Vitro Activity

Test Example 1: ELSA Detection of the Binding of Anti-TSLP Antibodies to Human TSLP Human TSLP-his (SEQ ID NO: 1) was diluted to 1 μg/ml with pH 7.4 PBS (Shanghai BasalMedia, B320) buffer, added at 100 μg/well to 96-well microtiter plates (Corning, CLS3590-100EA) and incubated overnight at 4° C. After discarding the liquid, 200 l/well of blocking solution with 5% skimmed milk (Bright Dairy skimmed milk powder) diluted in PBS was added and incubated in a 37° C. incubator for 2 hours for blocking. After blocking was over, the blocking solution was discarded, and the plates were washed with PBST buffer (PBS containing 0.1% tween-20, pH 7.4) for 3 times. The antibodies to be tested and the positive antibody AMG157 at different concentrations diluted with the sample diluent were added at 100 μl/well and incubated in a 37° C. incubator for 1 hour. After incubation was over, the plates were washed with PBST for 3 times. HRP-labeled goat anti-mouse secondary antibody (Jackson Immuno Research, 115-035-003) diluted with sample diluent was added at 100 l/well and incubated at 37° C. for 1 hour. After washing the plate with PBST for 6 times, 50 μl/well TMB chromogenic substrate (KPL, 52-00-03) was added and incubated at room temperature for 10-15 min, and 50 μl/well 1 M $H_2SO_4$ was added to stop the reaction. The absorption value was read by using a NOVOStar microplate reader at 450 nm. The EC50 value of the TSLP antibodies binding to TSLP was calculated and the results are shown in the following table.

TABLE 35

Results of binding activity of antibodies to human TSLP

| Antibody | EC50 (nM) |
|---|---|
| Ch3 | 0.4929 |
| hu3-01 | 0.8494 |
| hu3-02 | 0.6285 |
| hu3-03 | 0.5545 |
| hu3-04 | 0.4353 |
| hu3-05 | 0.5168 |
| hu3-06 | 0.594 |
| hu3-07 | 0.3853 |
| hu3-08 | 0.4687 |
| hu3-09 | 0.4941 |
| hu3-10 | 0.3879 |
| hu3-12 | 0.1519 |
| hu3-13 | 0.1477 |
| Ch119 | 0.851 |
| hu119-01 | 0.107 |
| hu119-02 | 0.1938 |
| hu119-03 | 0.1593 |
| hu119-04 | 0.1881 |
| hu119-05 | 0.1445 |
| hu119-06 | 0.2206 |
| hu119-07 | 0.2132 |
| hu119-08 | 0.2015 |
| hu119-09 | 0.1492 |
| hu119-10 | 0.2329 |
| hu119-11 | 0.174 |
| hu119-12 | 0.2034 |
| hu119-13 | 0.3438 |
| hu119-14 | 0.345 |
| hu119-15 | 0.3497 |
| hu119-16 | 0.366 |
| hu119-17 | 0.3515 |
| hu119-18 | 0.3455 |
| hu119-19 | 0.3533 |
| hu119-20 | 0.3412 |
| hu119-21 | 0.3987 |
| hu119-22 | 0.351 |
| hu119-23 | 0.3404 |
| hu119-24 | 0.3446 |
| hu119-25 | 0.3575 |
| hu119-26 | 0.3782 |
| hu119-27 | 0.3347 |
| hu119-28 | 0.2648 |
| hu119-29 | 0.2729 |
| hu119-28 | 0.2648 |
| hu119-29 | 0.2729 |
| Ch 179 | 0.2023 |
| hu179-01 | 0.1248 |
| hu179-02 | 0.1697 |
| hu179-03 | 0.138 |
| hu179-04 | 0.1886 |
| hu179-05 | 0.1416 |
| hu179-06 | 0.2188 |
| hu179-07 | 0.4478 |
| hu179-08 | 1.01615 |
| hu179-09 | 0.1573 |
| hu179-10 | 0.19 |
| hu179-11 | 0.1369 |
| hu179-12 | 0.1437 |
| hu179-13 | 0.2011 |
| hu179-14 | 0.2053 |
| hu179-15 | 0.2035 |
| hu179-16 | 0.2287 |
| hu179-17 | 0.218 |
| hu179-18 | 0.2458 |
| hu179-19 | 0.1616 |
| hu179-20 | 0.7077 |
| hu179-21 | 0.9784 |
| hu179-22 | 0.7519 |
| hu179-23 | 0.997 |
| hu179-24 | 0.6358 |
| hu179-25 | 0.1313 |
| hu179-26 | 0.2006 |
| hu179-27 | 0.1799 |
| hu179-28 | 0.0906 |
| hu179-29 | 0.2041 |
| hu179-30 | 0.246 |

TABLE 35-continued

Results of binding activity of antibodies to human TSLP

| Antibody | EC50 (nM) |
|---|---|
| hu179-31 | 0.2012 |
| hu179-32 | 0.145 |
| Ch 199 | 0.5157 |
| AMG157 | 0.7219 |

The results showed that the antibodies in the present disclosure have very good binding activity with human TSLP.

Test Example 2: Biacore Detection of the Affinity of Anti-TSLP Humanized Antibodies With Different Species of TSLP The affinity of the humanized TSLP antibodies to be tested with human and cyno TSLP was detected by a Biacore T200 (GE) instrument.

The molecules to be tested were affinity captured by Protein A biosensor chips (Cat. #29127556, GE). Then the antigens (huTSLP-his, cynoTSLP-his, prepared in Example 1) were allowed to flow across the chip surface, and the reaction signal was detected in real time by using the Biacore T200 instrument to obtain the binding and dissociation curves. After the dissociation of each experimental cycle was completed, the biosensor chips were washed and regenerated with glycine-hydrochloric acid regeneration solution (pH 1.5, Cat. #BR-1003-54, GE). The data was fit with a (1:1) Langmuir model by using BIAevaluation version 4.1, GE software to obtain the affinity value, as shown in the following table.

TABLE 36

Affinity of anti-TSLP antibodies with TSLP of different species

| Antibody | affinity to huTSLP KD (M) | affinity to Cyno TSLP KD (M) |
|---|---|---|
| AMG157 | 8.12E−12 | 9.22E−12 |
| hu179-33 | 9.03E−13 | 3.04E−11 |
| hu3-13 | 1.0E−12 | 3.40E−10 |
| hu119-30 | 5.0E−12 | 1.95E−09 |
| hu199-36 | 10.5E−12 | 1.72E−11 |

The results showed that the anti-TSLP antibodies in the present disclosure have relatively high affinity to human TSLP, and can also bind to cyno TSLP.

Test Example 3: ELSA-Based Experiment of Anti-TSLP Antibodies Blocking the Binding of TSLP to TSLP Receptor The TSLP receptor has two subunits, TSLPR and IL7R, of which TSLPR is a specific receptor for TSLP, and IL7R is a common receptor for TSLP and IL7. TSLP binds first to TSLPR and then to IL7R. This test example was used to identify whether the TSLP antibodies can block the binding of TSLP to the extracellular domain of recombinant expressed TSLPR receptor protein.

The ELISA plates were coated with human-TSLPR-Fc-ECD (2 μg/ml, SEQ ID NO: 5) and incubated overnight at 4° C. After discarding the liquid, 200 l/well blocking solution with 5% skimmed milk diluted in PBS was added and incubated in a 37° C. incubator for 2 hours for blocking. After blocking was over, the blocking solution was discarded and the plates were washed with PBST buffer (PBS containing 0.05% tween-20, pH7.4) for 3 times. Biotin-labeled huTSLP-Fc antigen was prepared at 3 nM, and the antibodies to be tested was serially diluted starting from 200 nM. The antigen and antibody were 1:1 mixed, then placed at 37° C. for 15 min, added at 100 μl per well to the microtiter plates and placed at 37° C. for 1 h. The plates were washed with PBST for 3 times. Streptavidin-Peroxidase Polymer diluted to 1:4000 with the sample diluent was added at 100 μl/well and incubated at 37° C. for 1 hour. After washing the plates with PBST for 5 times, 100 μl/well TMB chromogenic substrate (KPL, 52-00-03) was added and incubated at room temperature for 3-10 min, and 100 μl/well 1M $H_2SO_4$ was added to stop the reaction. The absorption value was read by using a NOVOStar microplate reader at 450 nm. The IC50 value of the TSLP antibodies blocking the binding of TSLP to TSLPR was calculated and the results are shown in Table 37 and FIG. 1.

TABLE 37

Results of blocking activity of antibodies

| Antibody | hu179-33 | hu119-30 | hu3-13 | hu199-36 |
|---|---|---|---|---|
| IC50 (nM) | 0.5038 | 0.5192 | 0.4975 | 0.5693 |

The results showed that all the antibodies of the present disclosure can strongly inhibit the binding of TSLP to its receptor TSLPR.

Test Example 5: FACS-Based Experiment of TSLP Antibody Blocking the Binding of TSLP to TSLP Receptor This test example was used to identify whether the anti-TSLP antibodies can respectively block the binding of TSLP to TSLPR/IL7R receptors on the surface of CHOK1 cell line.

The detailed method was: CHOK1-TSLPR/IL7R was cultured with DME/F12 containing 10% FBS, 1 mg/ml G418 and 10 μg/ml puromycin. CHOK1-TSLPR/IL7R cells in good condition were centrifuged (1000 rpm, 5 min), washed once with 2% FBS in PBS. The cells were counted and adjusted to a cell concentration of $1 \times 10^6$/ml. 50 μl of cells were added to round-bottomed 96-well plates. The antibodies to be tested were diluted with PBS solution containing 2% BSA, with an initial concentration of 20 nM and 8 gradients at a ratio of 1:4. Biotin-labeled TSLP-Fc antigen was prepared at 2 nM. The antigen and antibody were 1:1 mixed and placed at 37° C. for 15 min. The mixture was added at 50 μl per well to the 96-well plates where the cells have been plated, and incubated at 4° C. for 1 hour. After incubation was over, the plates were centrifuged at 4° C. (800 g, 5 min) and the supernatant was discarded. The plates were washed twice with 200 μl of pre-cooled PBS by centrifugation. 1:1000 diluted PE-SA secondary antibody was added and incubated at 4° C. in the dark for 40 min. Then the plates were centrifuged at 4° C. (800 g, 5 min) and the supernatant was discarded. 200 μl of pre-cooled PBS was added to blow up the cells, which were washed by centrifugation at 4° C. for three times. 100 μl PBS was added and the plate was loaded onto the machine for plate reading. The IC50 value of TSLP antibodies blocking the binding of TSLP to TSLPR/IL7R was calculated according to the value of the fluorescence signals. The results are as shown in Table 38.

TABLE 38

Results of antibodies blocking cell surface TSLPR

| Antibody | AMG157 | hu179-33 | hu119-30 | hu3-13 | hu199-36 |
|---|---|---|---|---|---|
| IC50 (nM) | 0.2068 | 0.1867 | 0.1368 | 0.1325 | 0.2270 |

The results showed that the antibodies of the present disclosure can all relatively strongly block the binding of TSLP to cell surface TSLPR/IL7R.

Test Example 6: Anti-TSLP Antibodies Inhibited TSLP-Induced Chemokine Production TSLP can induce the naive myeloid dendritic cells (mDCs) to be matured and to secrete the chemokine thymus activation regulatory chemokine (TARC) and osteoprotegerin (OPG), thereby further mediating the innate and adaptive immune inflammatory response. This test example was used to verify that the obtained antibodies can block TSLP-induced chemokine production by mDCs, thereby blocking the occurrence of innate and adaptive inflammation response.

Figure 4A:
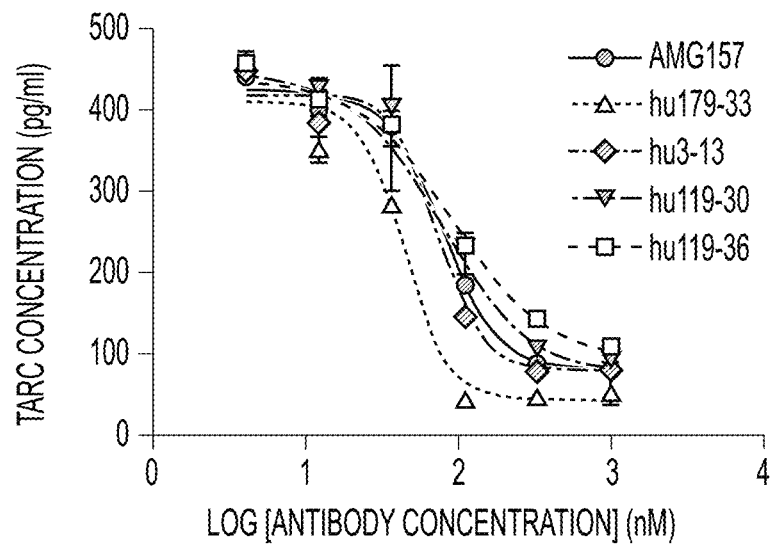
FIG. 4A shows the antibody activity of inhibiting the TSLP-induced production of the chemokine TARC.
Figure 4B:
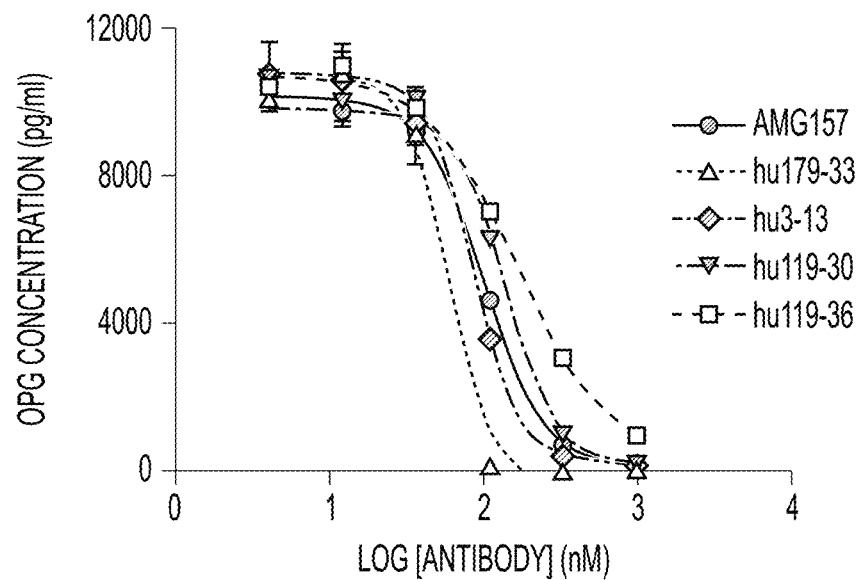
FIG. 4B shows the antibody activity of inhibiting the TSLP-induced production of the chemokine OPG.
Figure 5A:
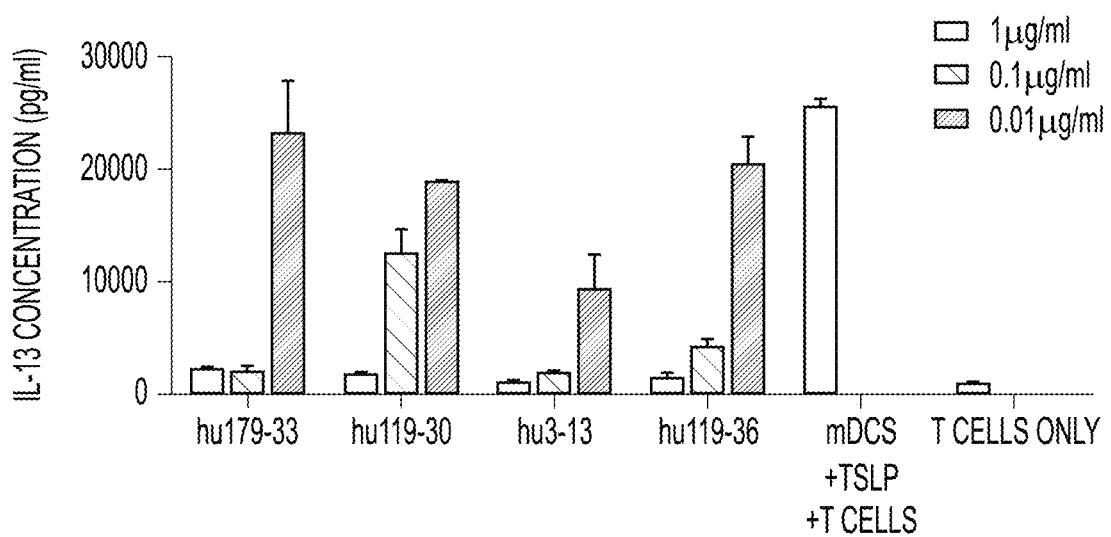
FIG. 5A shows the antibody activity of inhibiting the production of the Th2 cytokine IL-13.
Figure 5B:
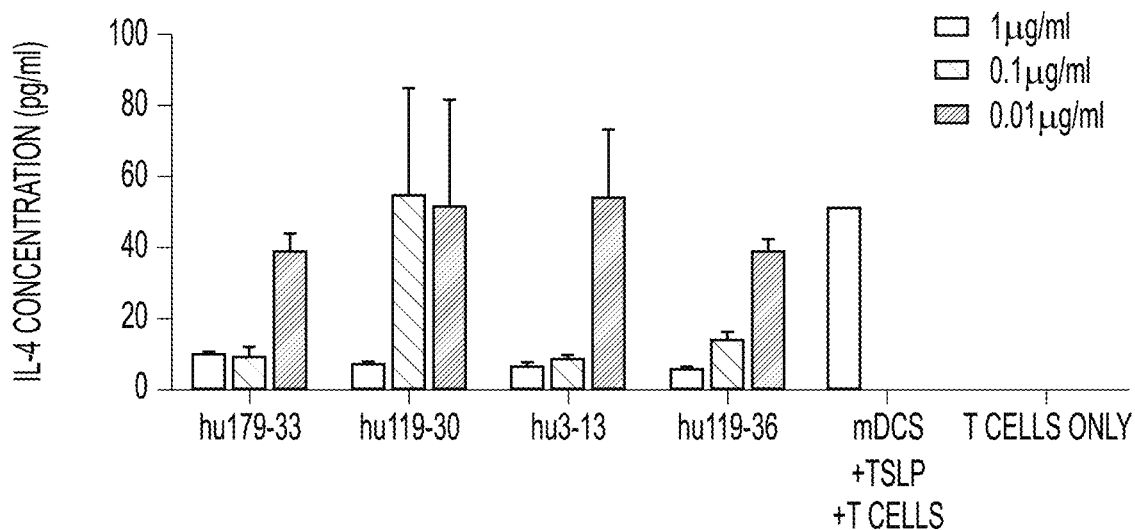
FIG. 5B shows the antibody activity of inhibiting the production of the Th2 cytokine IL-4.
Figure 5C:
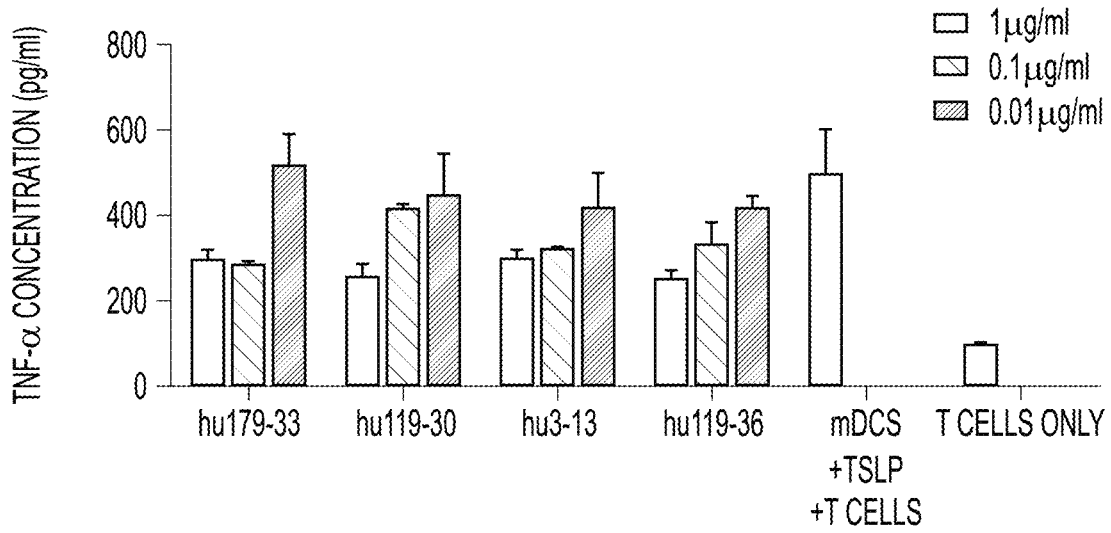
FIG. 5C shows the antibody activity of inhibiting the production of the Th2 cytokine TNF-α.
Figure 5D:
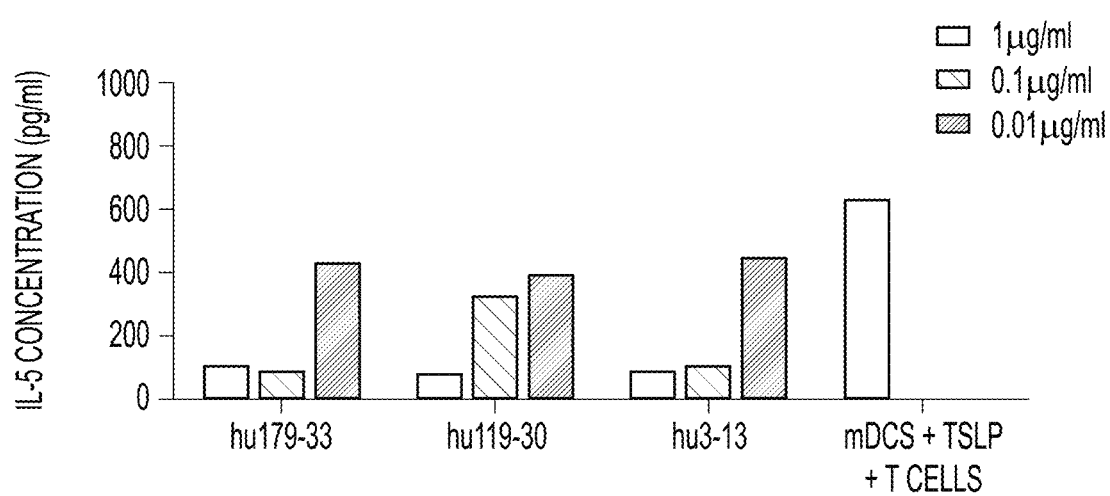
FIG. 5D shows the antibody activity of inhibiting the production of the Th2 cytokine IL-5.

Naive myeloid mDCs were separated and purified from human peripheral blood mononuclear cells (PBMCs) by using magnetic bead sorting method (CD1c (BDCA-1)+ Dendritic Cell Isolation Kit, Miltenyi Biotec). The obtained mDCs were seeded in 96-well cell culture plates. Serially diluted antibody samples and human TSLP (huTSLP-his, final concentration of 50 ng/ml) were pre-incubated for about 45 minutes (37° C.) and then respectively added to each cell culture well containing mDCs to stimulate mDCs in vitro. The plates were placed in an incubator to culture for 48 hours. The cell culture supernatant was collected and diluted properly, and then the chemokine content therein was detected by using ELISA method. TARC was detected by using human CCL17/TARC Quantikine ELISA Kit from R&D Company; OPG content was detected by using human CCL22/MDC Quantikine ELISA Kit (R&D), and the results are shown in FIG. 4A-FIG. 4B.

The results showed that all the antibodies in the present disclosure can significantly inhibit TSLP-induced TARC and OPG chemokine production, indicating that the antibodies in the present disclosure can block the occurrence of innate and adaptive inflammatory response.

Test Example 7. Anti-TSLP Antibodies Blocked the Proliferation of BaF3-TLSPR/IL7R Cells Induced by Native TSLP BaF3-hTSLPR/hIL7R cells can proliferate under the stimulation of native TSLP. Binding of antibodies to native TSLP reduces the stimulatory effect of TSLP on BaF3-hTSLPR/hIL7R cells.

NHLF cells (BeNa Culture Collection BNCC340764) and HLF1 cells (BeNa Culture Collection BNCC337730) were cultured until the cells grew to 80%, and the supernatant was discarded. Human lung fibroblasts, NHLF (BeNa Culture Collection BNCC340764) and HLF1 (BeNa Culture Collection BNCC337730), were stimulated with 10 ng/ml human IL1-β (Sino Biological GMP-10139-HNAE), 20 ng/ml IL13 (R&D 213-ILB-005), 20 ng/ml TNF-α (PEPRO-TECH 300-01A) for 72 hours to induce the production of native TSLP. After stimulation was over, the cell supernatant was collected and centrifuged at 4500 rpm for 5 min to remove cell debris. The supernatant was collected, concentrated for about 10 times by concentration columns, and filtered for later use.

BaF3-hTSLPR/hIL17R cells were cultured in RPMI1640 with 10% FBS (10 ng/mL mIL3, R&D 213-ILB-005), adjusted to a density of $1\times10^4$ cells/ml and cultured in a 37° C., 5% $CO_2$ incubator to Logarithmic growth phase. The cells were collected, centrifuged at 800 rpm/min for 5 min, and the supernatant was discarded; the cells were washed with PBS for three times to remove the cytokines that stimulate their proliferation in the culture medium. The cells were resuspended in RPMI1640 medium with 4% FBS, seeded into 96-well plates at 4000 cells/50 μl/well and cultured in an incubator for 2 h. The antibodies to be tested was serially diluted by using native TSLP at 10-fold ratio, with an initial antibody concentration of 100 nM, resulting in 3 dilution gradients, 100 nM, 10 nM and 1 nM. 50 l/well of the diluted antibody/antigen mixture was added to the cells with the final antibody concentration of 50 nM, 5 nM, 0.5 nM. The plates were incubated in a 37° C., 5% $CO_2$ incubator for 72 h. Then 30 μL CellTiter-Glo (Promega) was added to each well and incubated in the dark at room temperature for 10 min, and detected by using the Luminescence program with Cytation5 cell imager. The results are shown in the following table.

TABLE 39

Results of anti-TSLP antibodies inhibiting the proliferation of BaF3-TLSPR/IL7R cells

| Antibody | AMG157 | hu179-33 | hu3-13 | hu119-30 |
|---|---|---|---|---|
| IC50 (nM) | 3.379 | 0.02279 | 0.2888 | 1.533 |

The results showed that all the antibodies obtained in the present disclosure can significantly inhibit the activity of native TSLP to stimulate the proliferation of BaF3, especially hu179-33, the activity of which was more than 100 times of that of AMG157.

Test Example 8: Experiment of Anti-TSLP Antibodies Inhibiting TSLP-Induced Proliferation of BaF3 Cells Overexpressing TSLPR/IL7R TSLP can bind to TSLPR/IL7R on the surface of BaF3, thereby promoting the proliferation of BaF3. This test example was used to identify whether the antibodies of the present disclosure can block the activity of TSLP to induce the proliferation of BaF3.

Figure 3:
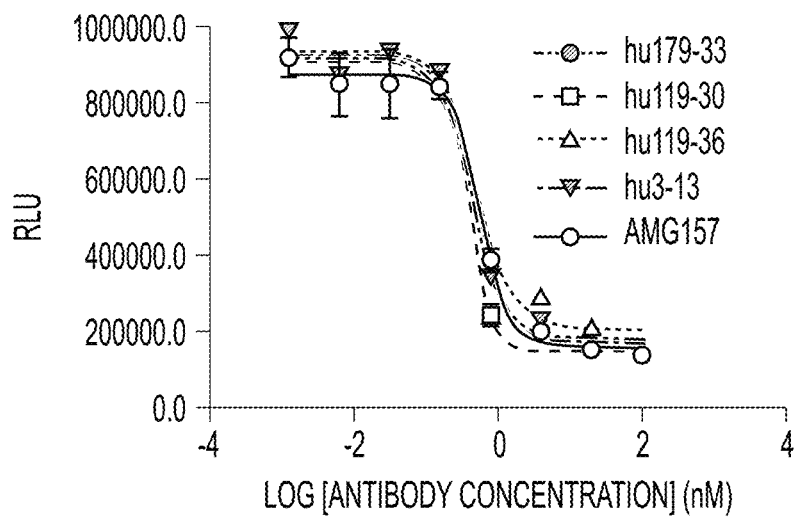
FIG. 3: The antibody inhibits TSLP-induced proliferation activity of BaF3 cells.

Specifically, BaF3 cells overexpressing TSLPR/IL7R were cultured in RPMI1640 with 10% FBS and 2 ng/mL rhIL3 (MultiSciences, Catalog No. 96-AF-300-03-20), cultured in a 37° C., 5% $CO_2$ incubator, with the cell density not exceeding $1\times10^6$ cells/ml. When detecting the antibodies, cells in logarithmic growth phase were washed with PBS for three times and centrifuged at 800 rpm for 5 min. The cell density was adjusted to 8000 cells/well/90 μl with RPMI1640 (2% FBS, recombinant human TSLP-Fc: 40 ng/ml). 10 μl of serially diluted antibody to be tested was added to the 96-well plates and cultured for 2 days. 30 μl cell titer was added and mixed for detection. IC50 was calculated according to the reading. The results are shown in Table 40 and FIG. 3.

TABLE 40

Inhibition of the proliferation activity of BaF3 cells by antibodies

| Antibody | AMG157 | hu179-33 | hu119-30 | hu3-13 | hu199-36 |
|---|---|---|---|---|---|
| IC50 (nM) | 0.5730 | 0.4092 | 0.4305 | 0.4436 | 0.4760 |

The results showed that all the antibodies of the present disclosure have relatively strong ability to inhibit TSLP-mediated proliferation of BaF3 cells.

Test Example 9: Humanized Anti-TSLP Antibodies Blocked TSLP-Induced Differentiation of Native CD4+ T Cells into Th2 Cells TSLP can induce the maturation of primary myeloid mDC cells. Mature mDC cells highly express OX40 ligand, which can bind to OX40 on the surface of native CD4+ T cells, thereby differentiating the native CD4+ T into Th2 cells, which produce factors related to immune response such as IL4/IL5/IL13, etc., leading to Th2 inflammatory response in the body. This test example was used to detect whether the antibodies obtained in the present disclosure can block TSLP-induced differentiation of Th2 cells.

Naive myeloid DCs were separated and purified from human peripheral blood mononuclear cells (PBMCs) by using magnetic bead sorting method (CD1c (BDCA-1)+ Dendritic Cell Isolation Kit, Miltenyi Biotec). The obtained mDCs were seeded in 96-well cell culture plates. Serially diluted antibody samples and recombinant expressed human TSLP (huTSLP-his, final concentration 50 ng/ml) were pre-incubated (37° C.) for about 45 minutes and then respectively added to each cell culture well containing mDCs and cultured at 37° C. for 24 hours. The mature mDCs after stimulation were collected and washed with PBS twice. CD4+ CD45RA+ native T cells were extracted from PBMCs by magnetic bead separation method (Myltenyi, Biotec). The native T cells obtained by separation and the mature mDCs were mixed and seeded in 96-well cell culture plates at a ratio of 5:1, and co-cultured for 6 days. The cells were collected and seeded in 96-well plates pre-coated with anti-CD3 (10 μg/ml), and anti-CD28 (1 μg/mL) was added to stimulate the differentiated T cells again. The cells were cultured for 24 hours and finally the cell culture supernatant was collected. Th2-related cytokines secreted by cells in the supernatant were detected by ELISA. IL-4 and IL-5 cytokines were detected by ELISA kits from R&D, and TNF-α and IL-13 were detected by ELISA kits from NeoBioscience. The results are shown in FIG. 5A-FIG. 5D.

The results showed that the antibodies obtained in the present disclosure can significantly inhibit the production of Th2 cytokines IL4, IL5, IL13 and TNF-α, indicating that the antibodies obtained in the present disclosure can block TSLP-induced differentiation of Th2 cells.

What is claimed is:

1. An anti-thymic stromal lymphopoietin (anti-TSLP) antibody comprising a heavy chain variable region and a light chain variable region, wherein:
   (i) the heavy chain variable region comprises HCDR1, HCDR2 and HCDR3 as shown in SEQ ID NO: 26, SEQ ID NO: 94 and SEQ ID NO: 28, respectively; and,
   (ii) the light chain variable region comprises LCDR1, LCDR2 and LCDR3 as shown in SEQ ID NO: 29, SEQ ID NO: 113 and SEQ ID NO: 31, respectively.

2. The anti-TSLP antibody according to claim 1, wherein the anti-TSLP antibody is a murine antibody, a chimeric antibody, or a humanized antibody.

3. The anti-TSLP antibody according to claim 1, wherein the amino acid sequence of the heavy chain variable region comprises the sequence of SEQ ID NO: 97, and the amino acid sequence of the light chain variable region comprises the sequence of SEQ ID NO: 119.

4. The anti-TSLP antibody according to claim 3, wherein the antibody further comprises an antibody heavy chain constant region and a light chain constant region; wherein the heavy chain constant region is selected from the group consisting of human IgG1, IgG2, IgG3 and IgG4 constant regions; and wherein the light chain constant region is selected from the group consisting of human antibody κ (kappa), human antibody λ (lambda) chain constant regions.

5. The anti-TSLP antibody according to claim 4, wherein the antibody comprises a heavy chain constant region as shown in SEQ ID NO: 133, and comprises a light chain constant region as shown in SEQ ID NO: 134.

6. An anti-TSLP antibody comprising:
   (i) a heavy chain variable region comprising the amino acid sequence of SEQ ID NO: 97;
   (ii) a light chain variable region comprising the amino acid sequence of SEQ ID NO: 119;
   iii) a human IgG1 heavy chain constant region; and,
   (iv) a light chain constant region that is selected from the group consisting of a human κ (kappa) light chain constant region, λ (lambda) light chain constant region.

7. The anti-TSLP antibody according to claim 6, wherein the antibody comprises a heavy chain constant region as shown in SEQ ID NO: 133, and a light chain constant region as shown in SEQ ID NO: 134.

8. A pharmaceutical composition containing a therapeutically effective amount of the anti-TSLP antibody according claim 1 and one or more pharmaceutically acceptable carriers, diluents, buffers, or excipients.

9. An anti-thymic stromal lymphopoietin (anti-TSLP) antibody comprising: a heavy chain comprising the amino acid as shown in SEQ ID NO: 139, and a light chain comprising the amino acid sequence as shown in SEQ ID NO: 140.

* * * * *